US012146150B2

(12) United States Patent
Sah et al.

(10) Patent No.: US 12,146,150 B2
(45) Date of Patent: Nov. 19, 2024

(54) RESCUE OF CENTRAL AND PERIPHERAL NEUROLOGICAL PHENOTYPE OF FRIEDREICH'S ATAXIA BY INTRAVENOUS DELIVERY

(71) Applicants: VOYAGER THERAPEUTICS, INC., Cambridge, MA (US); INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ DE STRASBOURG, Strasbourg (FR)

(72) Inventors: Dinah Wen-Yee Sah, Hopkinton, MA (US); Martin Goulet, Weston, MA (US); Holger Patzke, Belmont, MA (US); Yanqun Shu, Winchester, MA (US); Jinzhao Hou, Lexington, MA (US); Hélène Puccio, Illkirch (FR)

(73) Assignees: VOYAGER THERAPEUTICS, INC., Cambridge, MA (US); INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ DE STRASBOURG, Strasbourg (FR)

(*) Notice: Subject to any disclaimer, the term of this patent is extended or adjusted under 35 U.S.C. 154(b) by 63 days.

(21) Appl. No.: 17/931,725

(22) Filed: Sep. 13, 2022

(65) Prior Publication Data
US 2023/0044444 A1 Feb. 9, 2023

Related U.S. Application Data

(63) Continuation of application No. 16/651,617, filed as application No. PCT/US2018/053312 on Sep. 28, 2018, now abandoned.

(60) Provisional application No. 62/663,835, filed on Apr. 27, 2018, provisional application No. 62/565,840, filed on Sep. 29, 2017.

(51) Int. Cl.
| | |
|---|---|
| C12N 15/86 | (2006.01) |
| A61K 48/00 | (2006.01) |
| A61P 25/00 | (2006.01) |
| C07K 14/47 | (2006.01) |
| C12N 7/00 | (2006.01) |

(52) U.S. Cl.
CPC ............ *C12N 15/86* (2013.01); *A61K 48/005* (2013.01); *A61P 25/00* (2018.01); *C07K 14/47* (2013.01); *C12N 7/00* (2013.01); *C12N 2750/14123* (2013.01); *C12N 2750/14143* (2013.01)

(58) Field of Classification Search
CPC ......... C12N 15/86; C12N 7/00; A61K 48/005
See application file for complete search history.

(56) References Cited

U.S. PATENT DOCUMENTS

| | | | |
|---|---|---|---|
| 5,064,764 | A | 11/1991 | Besnainon |
| 5,474,935 | A | 12/1995 | Chatterjee |
| 5,587,308 | A | 12/1996 | Carter |
| 5,652,224 | A | 7/1997 | Wilson |
| 5,658,785 | A | 8/1997 | Johnson |
| 5,688,676 | A | 11/1997 | Zhou |
| 5,691,176 | A | 11/1997 | Lebkowski |
| 5,693,531 | A | 12/1997 | Chiorini |
| 5,741,683 | A | 4/1998 | Zhou |
| 5,756,283 | A | 5/1998 | Wilson |
| 5,856,152 | A | 1/1999 | Wilson |
| 5,858,351 | A | 1/1999 | Podsakoff |
| 5,858,775 | A | 1/1999 | Johnson |
| 5,866,552 | A | 2/1999 | Wilson |
| 5,866,696 | A | 2/1999 | Carter |
| 5,871,982 | A | 2/1999 | Wilson |
| 5,952,221 | A | 9/1999 | Kurtzman |
| 5,962,313 | A | 10/1999 | Podsakoff |
| 5,989,540 | A | 11/1999 | Carter |
| 6,083,716 | A | 7/2000 | Wilson |
| 6,143,548 | A | 11/2000 | ORiordan |
| 6,143,567 | A | 11/2000 | Van Agthoven |
| 6,146,874 | A | 11/2000 | Zolotukhin |
| 6,156,303 | A | 12/2000 | Russell |
| 6,174,527 | B1 | 1/2001 | Wilson |
| 6,180,613 | B1 | 1/2001 | Kaplitt |
| 6,194,191 | B1 | 2/2001 | Zhang |
| 6,200,560 | B1 | 3/2001 | Couto |
| 6,204,059 | B1 | 3/2001 | Samulski |
| 6,211,163 | B1 | 4/2001 | Podsakoff |
| 6,251,677 | B1 | 6/2001 | Wilson |

(Continued)

FOREIGN PATENT DOCUMENTS

| | | |
|---|---|---|
| EP | 1015619 A1 | 7/2000 |
| EP | 1046711 | 10/2000 |

(Continued)

OTHER PUBLICATIONS

Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. 2015 Oct. 26 (10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.

(Continued)

*Primary Examiner* — Tekchand Saidha
(74) *Attorney, Agent, or Firm* — K&L Gates LLP

(57) ABSTRACT

Described herein are compositions and methods for treating Friedreich's Ataxia (FA) using adeno-associated virus (AAV) to deliver therapeutics agents.

20 Claims, 21 Drawing Sheets

Specification includes a Sequence Listing.

(56) References Cited

U.S. PATENT DOCUMENTS

| | | |
|---|---|---|
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,579,181 B2 | 8/2009 | ORiordan |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Rom |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,102,943 B2 | 8/2015 | Shinmura |
| 9,115,373 B2 | 8/2015 | Hermens |
| 9,163,260 B2 | 10/2015 | Wilson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,493,788 B2 | 11/2016 | Gao |
| 9,506,083 B2 | 11/2016 | Arbetman |
| 9,528,126 B2 | 12/2016 | Qu |

(56) References Cited

U.S. PATENT DOCUMENTS

| | | |
|---|---|---|
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,670,507 B2 | 6/2017 | Xiao |
| 9,677,088 B2 | 6/2017 | Nakai |
| 9,677,089 B2 | 6/2017 | Gao |
| 9,695,220 B2 | 7/2017 | Vandenberghe |
| 9,719,070 B2 | 8/2017 | Vandenberghe |
| 9,725,485 B2 | 8/2017 | Srivastava |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,825 B2 | 10/2017 | Chatterjee |
| 9,790,472 B2 | 10/2017 | Gao |
| 9,803,218 B2 | 10/2017 | Chatterjee |
| 10,337,027 B2 | 7/2019 | Puccio et al. |
| 11,512,327 B2 | 11/2022 | Sah et al. |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0261218 A1 | 11/2005 | Esau |
| 2006/0003451 A1 | 1/2006 | Gao |
| 2006/0204479 A1 | 9/2006 | Wilson |
| 2007/0004042 A1 | 1/2007 | Gao |
| 2008/0008684 A1 | 1/2008 | Wilson |
| 2008/0050343 A1 | 2/2008 | Wilson |
| 2008/0050345 A1 | 2/2008 | Wilson |
| 2008/0075737 A1 | 3/2008 | Gao |
| 2009/0215871 A1 | 8/2009 | Wilson |
| 2009/0275107 A1 | 11/2009 | Lock |
| 2009/0317417 A1 | 12/2009 | Vandenberghe |
| 2010/0247490 A1 | 9/2010 | Roy |
| 2010/0278791 A1 | 11/2010 | Wilson |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2012/0046349 A1 | 2/2012 | Bell |
| 2012/0058102 A1 | 3/2012 | Wilson |
| 2012/0093853 A1 | 4/2012 | Wilson |
| 2012/0137379 A1 | 5/2012 | Gao |
| 2012/0244131 A1 | 9/2012 | Delacote |
| 2012/0258046 A1 | 10/2012 | Mutzke |
| 2013/0023033 A1 | 1/2013 | Wilson |
| 2013/0045186 A1 | 2/2013 | Gao |
| 2013/0101558 A1 | 4/2013 | Gao |
| 2013/0109658 A1 | 5/2013 | Testi et al. |
| 2013/0195801 A1 | 8/2013 | Gao |
| 2013/0196932 A1 | 8/2013 | Testi |
| 2013/0296532 A1 | 11/2013 | Hermens |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0221462 A1 | 8/2014 | Puccio |
| 2014/0296486 A1 | 10/2014 | Gao |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0159173 A1 | 6/2015 | Vandenberghe |
| 2015/0238610 A1 | 8/2015 | Sista |
| 2015/0307898 A2 | 10/2015 | Hermens |
| 2015/0313969 A1 | 11/2015 | Puccio et al. |
| 2015/0315610 A1 | 11/2015 | Nishie |
| 2015/0374803 A1 | 12/2015 | Wolfe |
| 2016/0032319 A1 | 2/2016 | Wright |
| 2016/0108373 A1 | 4/2016 | Bennett |
| 2016/0153992 A1 | 6/2016 | Buening |
| 2016/0166709 A1 | 6/2016 | Davidson |
| 2016/0271192 A1 | 9/2016 | Roy |
| 2016/0273058 A1 | 9/2016 | Akashika |
| 2016/0289275 A1 | 10/2016 | Chiorini |
| 2016/0296694 A1 | 10/2016 | Bankiewicz |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0361439 A1 | 12/2016 | Agbandje-McKenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0028082 A1 | 2/2017 | Wilson |
| 2017/0044504 A1 | 2/2017 | Schaffer |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088858 A1 | 3/2017 | Gao |
| 2017/0096646 A1 | 4/2017 | Roy |
| 2017/0105927 A1 | 4/2017 | Thorne |
| 2017/0112946 A1 | 4/2017 | Ikeda |
| 2017/0121734 A1 | 5/2017 | Cairns |
| 2017/0128528 A1 | 5/2017 | Samulski |
| 2017/0128594 A1 | 5/2017 | Wright |
| 2017/0130208 A1 | 5/2017 | Potter |
| 2017/0130245 A1 | 5/2017 | Kotin |
| 2017/0145414 A1 | 5/2017 | Collard |
| 2017/0145440 A1 | 5/2017 | Hermens |
| 2017/0151348 A1 | 6/2017 | Kaspar |
| 2017/0151416 A1 | 6/2017 | Kutikov |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |

(56) References Cited

U.S. PATENT DOCUMENTS

| | | |
|---|---|---|
| 2017/0166925 A1 | 6/2017 | Gao |
| 2017/0166926 A1 | 6/2017 | Deverman |
| 2017/0166927 A1 | 6/2017 | Gao |
| 2017/0191039 A1 | 7/2017 | Gao |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0240921 A1 | 8/2017 | Gao |
| 2017/0274024 A1 | 9/2017 | McCown |
| 2017/0275337 A1 | 9/2017 | Srivastava |
| 2017/0298323 A1 | 10/2017 | Vandenberghe |
| 2021/0395776 A1 | 12/2021 | Patzke et al. |
| 2023/0304032 A1 | 9/2023 | Sah et al. |

FOREIGN PATENT DOCUMENTS

| | | |
|---|---|---|
| EP | 1078096 A1 | 2/2001 |
| EP | 1164195 | 12/2001 |
| EP | 1183380 A1 | 3/2002 |
| EP | 1218035 | 7/2002 |
| EP | 1240345 | 9/2002 |
| EP | 1279740 | 1/2003 |
| EP | 1453547 | 9/2004 |
| EP | 1696036 | 8/2006 |
| EP | 1847614 | 10/2007 |
| EP | 1849872 | 10/2007 |
| EP | 1857552 | 11/2007 |
| EP | 1944043 | 7/2008 |
| EP | 2007795 | 12/2008 |
| EP | 2198016 | 6/2010 |
| EP | 2220241 | 8/2010 |
| EP | 2220242 | 8/2010 |
| EP | 2292779 | 3/2011 |
| EP | 2325298 | 5/2011 |
| EP | 2359866 | 8/2011 |
| EP | 2383346 | 11/2011 |
| EP | 2524037 | 11/2012 |
| EP | 2531604 | 12/2012 |
| EP | 2660325 | 11/2013 |
| EP | 2737071 | 6/2014 |
| EP | 2814958 | 12/2014 |
| EP | 2871239 | 5/2015 |
| EP | 2879719 | 6/2015 |
| EP | 2598525 B1 | 8/2015 |
| EP | 2933336 | 10/2015 |
| EP | 3058959 | 8/2016 |
| EP | 3067417 | 9/2016 |
| EP | 2176283 | 11/2016 |
| EP | 3108000 | 12/2016 |
| EP | 3117005 | 1/2017 |
| EP | 3132043 B1 | 2/2017 |
| EP | 3134431 | 3/2017 |
| EP | 3168298 | 5/2017 |
| EP | 3221453 | 9/2017 |
| EP | 3390429 | 10/2018 |
| EP | 3429605 A2 | 1/2019 |
| WO | 1993009239 | 5/1993 |
| WO | 1995034670 | 12/1995 |
| WO | 1996017947 | 6/1996 |
| WO | 1996023810 | 8/1996 |
| WO | 1996030540 | 10/1996 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003087382 | 10/2003 |
| WO | 2003087383 | 10/2003 |
| WO | 2004044003 | 5/2004 |
| WO | 2004083441 | 9/2004 |
| WO | 2004108922 | 12/2004 |
| WO | 2004111248 | 12/2004 |
| WO | 2005005610 | 1/2005 |
| WO | 2005012537 | 2/2005 |
| WO | 2005111220 | 11/2005 |
| WO | 2006102072 | 9/2006 |
| WO | 2007130519 | 11/2007 |
| WO | 2007148971 | 7/2009 |
| WO | 2009134681 | 11/2009 |
| WO | 2011038187 | 3/2011 |
| WO | 2011054976 | 5/2011 |
| WO | 2011122950 | 10/2011 |
| WO | 2011133890 A2 | 10/2011 |
| WO | 2010109053 | 11/2011 |
| WO | 2012057363 | 5/2012 |
| WO | 2012114090 | 8/2012 |
| WO | 2012144446 | 10/2012 |
| WO | 2013078199 | 5/2013 |
| WO | 2013164793 | 11/2013 |
| WO | 2013170078 | 11/2013 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015018503 | 2/2015 |
| WO | 2014186746 | 3/2015 |
| WO | 2015031686 | 4/2015 |
| WO | 2015044292 | 4/2015 |
| WO | 2015060722 | 4/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015127128 | 11/2015 |
| WO | 2015196179 | 12/2015 |
| WO | 2016019364 | 2/2016 |
| WO | 2016054554 | 4/2016 |
| WO | 2016054557 | 4/2016 |
| WO | 2016065001 | 4/2016 |
| WO | 2016081811 | 5/2016 |
| WO | 2016081927 | 5/2016 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130591 | 8/2016 |
| WO | 2016137949 | 9/2016 |
| WO | 2016150964 A1 | 9/2016 |
| WO | 2016154055 | 9/2016 |
| WO | 2016154344 | 9/2016 |
| WO | 2016164609 | 10/2016 |
| WO | 2016168728 | 10/2016 |
| WO | 2016172008 | 10/2016 |
| WO | 2016172155 | 10/2016 |
| WO | 2016172659 A1 | 10/2016 |

(56) References Cited

FOREIGN PATENT DOCUMENTS

| WO | 2016179496 | 11/2016 |
| --- | --- | --- |
| WO | 2016183297 | 11/2016 |
| WO | 2016191418 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017143100 | 8/2017 |
| WO | 2017165859 | 9/2017 |
| WO | 2018152333 A1 | 8/2018 |
| WO | 2018156654 A1 | 8/2018 |
| WO | 2019006043 A1 | 1/2019 |
| WO | 2019006182 A1 | 1/2019 |
| WO | 2019028306 A2 | 2/2019 |
| WO | 2019046069 A1 | 3/2019 |

OTHER PUBLICATIONS

Pacouret S, et al. AAV-ID: A Rapid and Robust Assay for Batch-to-Batch Consistency Evaluation of AAV Preparations. Mol Ther. Apr. 17, 2017. Epub ahead of print.

Penaud-Budloo M, et al. Accurate identification and quantification of DNA species by next-generation sequencing in adeno-associated viral vectors produced in insect cells. Hum Gene Ther Methods. May 2, 2017. Epub ahead of print.

Ruffing M, et al. Assembly of viruslike particles by recombinant structural proteins of adeno-associated virus type 2 in insect cells. J Virol. Dec. 1992;66(12):6922-30.

Samulski RJ, et al. Helper-free stocks of recombinant adeno-associated viruses: normal integration does not require viral gene expression. J Virol. Sep. 1989;63(9):3822-8.

Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.

Urabe M, et al. Scalable generation of high-titer recombinant adeno-associated virus type 5 in insect cells. J Virol. Feb. 2006;80(4):1874-85.

Van Der Loo JCM, et al. Progress and challenges in viral vector manufacturing. Hum Mol Genet. Apr. 2016;25(R1): R42-52.

Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.

Zhao KN, et al. BPV1 E2 protein enhances packaging of full-length plasmid DNA in BPV1 pseudovirions. Virology. Jul. 5, 2000;272(2):382-93.

Pierson EE, et al. Resolving adeno-associated viral particle diversity with charge detection mass spectrometry. Anal Chem. Jul. 2016;88(13):6718-25.

Rashnonejad A, et al. Large-Scale Production of Adeno-Associated Viral Vector Serotype-9 Carrying the Human Survival Motor Neuron Gene. Mol Biotechnol. Jan. 2016;58(1):30-6.

Ling C, et al. Strategies to generate high-titer, high-potency recombinant AAV3 serotype vectors. Mol Ther Methods Clin Dev. May 2016;3:16029.

Afione S, et al. Identification and Mutagenesis of the Adeno-Associated Virus 5 Sialic Acid Binding Region.J Virol. Feb. 2015, 89(3):1660-72.

Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.

Halder S, et al. Structure of neurotropic adeno-associated virus AAVrh.8. J Struct Biol. Oct. 2015; 192(1):21-36.

Huang LY, et al. Characterization of the adeno-associated virus 1 and 6 sialic acid binding site. J Virol. May 2016;90 (11):5219-30.

Mao Y, et al. Single point mutation in adeno-associated viral vectors—DJ capsid leads to improvement for gene delivery in vivo. BMC Biotechnol. Jan. 2016;16:1.

Marsic D et al. Altering Tropism of rAAV by Directed Evolution. Methods of Mol Biol. 2016;1382:151-73.

Tu My, et al. Role of capsid proteins in parvoviruses infection. Virol J. Aug. 2015, 4;12:114.

Zeng C, et al. Probing the Link between Genomic Cargo, Contact Mechanics and Nanoindentation in Recombinant Adeno-Associated Virus 2. J Phys Chem B. Mar. 2017;121(8):1843-1853.

Zinn E, et al. In Silico Reconstruction of the Viral Evolutionary Lineage Yields a Potent Gene Therapy Vector. Cell Rep. Aug. 2015, 12(6):1056-68.

Grimm D, et al. E Pluribus Unum: 50 years of research, millions of viruses and one goal—tailored acceleration of AAV evolution. Mol Ther. Dec. 2015;23(12):1819-1831.

Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.

Ling C, et al. Development of Optimized AAV Serotype Vectors for High-Efficiency Transduction at Further Reduced Doses. Hum Gene Ther Methods. Aug. 2016;27(4): 143-9.

Pillay S, et al. An essential receptor for adeno-associated virus infection. Nature. Feb. 2016; 530(7588):108-12.

Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.

Shen S, et al. Functional Analysis of the Putative Integrin Recognition Motif on Adeno-associated virus 9. J Biol Chem. Jan. 2015, 290(3):1496-504.

Steines B, et al. CFTR gene transfer with AAV improves early cystic fibrosis pig phenotypes. JCI Insight. Sep. 2016;1(14):e88728.

Bensky MJ, et al. Targeted gene delivery to the enteric nervous system using AAV: a comparison across serotypes and capsid mutants.Mol Ther. Mar. 2015;23(3):488-500.

Castle MJ, et al. Controlling AAV Tropism in the Nervous System with Natural and Engineered Capsids. Methods Mol Biol. 2016;1382:133-49.

Choudhury SR, et al. Widespread CNS gene transfer and silencing after systemic delivery of novel AAV-AS vectors. Mol Ther. Apr. 2016;24(4):726-35.

Davis AS, et al. Rational design and engineering of a modified adeno-associated virus (AAV1)-based vector system for enhanced retrograde gene delivery. Neurosurgery. Feb. 2015;76(2):216-25.

Deverman BE et al. Cre-dependent selection yields AAV variants for widespread gene transfer to the adult brain. Nat Biotechnol. Feb. 2016;34(2):204-9.

Powell SK et al. Characterization of a novel adeno-associated viral vector with preferential oligodendrocyte tropism. Gene Ther. Sep. 15, 2016.

Tervo et al. A Designer AAV Variant Permits Efficient Retrograde Access to Projection Neurons. Neuron. Oct. 19, 2016;92(2):372-382.

Choudhury et al. In Vivo Selection Yields AAV-B1 Capsid for Central Nervous System and Muscle Gene Therapy. Mol Ther. Aug. 2016;24(7):1247-57.

(56) References Cited

OTHER PUBLICATIONS

Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines in Vitro and in Murine Hepatocytes in Vivo. J Virol. Jan. 2015, 89(2):952-61.
Xie J, et al. Short DNA Hairpins Compromise Recombinant Adeno-Associated Virus Genome Homogeneity. Mol Ther. Jun. 7, 2017;25(6):1363-1374.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015; 19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016; 12(1):e1005399.
Kailasan S, et al. Structure of an Enteric Pathogen, Bovine Parvovirus.J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Tadokoro T, et al. Subpial Adeno-associated Virus 9 (AAV9) Vector Delivery in Adult Mice. J Vis Exp. Jul. 13, 2017; (125). doi: 10.3791/55770.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc. 13861.
Gombash SE, et al. Systemic gene delivery transduces the enteric nervous system of guinea pigs and cynomolgus macaques. Gene Ther. Aug. 3, 2017. doi: 10.1038/gt.2017.72.
Giles AR, et al. Mapping an adeno-associated virus 9-specific neutralizing epitope to develop next-generation gene delivery vectors. J Virol. Aug. 8, 2018 Epub ahead of print.
Piguet F, et al. Rapid and complete reversal of sensory ataxia by gene therapy in a novel model of Friedreich ataxia. Mol Ther May 10, 2018 Epub ahead of print.
Wang D, et al. A Rationally Engineered Capsid Variant of AAV9 for Systemic CNS-Directed and Peripheral Tissue—Detargeted Gene Delivery in Neonates. Mol Ther Methods Clin Dev. Mar. 16, 2018;9:234-246.
Gerard, et al. An AAV9 coding for frataxin clearly improved the symptoms and prolonged the life of Friedreich ataxia mouse models. Mol Ther Methods Clin Dev. Oct. 8, 2014;1:14044.
Matsuzaki Y, et al. Intravenous administration of the adeno-associated virus-PHP.B capsid fails to upregulate transduction efficiency in the marmoset brain Neurosci Lett. Feb. 5, 2018;665:182-188.
Hosaka K, et al. Localized Intra-Arterial Gene Delivery Using AAV. Methods Mol Biol. 2019; 1937:259-265.
Huang Q, et al. Delivering genes across the blood-brain barrier: LY6A, a novel cellular receptor for AAV-PHP.B capsids. bioRxiv. Feb. 1, 2019.
Gessler DJ, et al. Intravenous Infusion of AAV for Widespread Gene Delivery to the Nervous System. Methods Mol Biol. 2019; 1950:143-163.
Matsuzaki Y, Tanaka M, Hakoda S, Masuda T, Miyata R, Konno A, Hirai H. Neurotropic Properties of AAV-PHP.B Are Shared among Diverse Inbred Strains of Mice .Mol Ther. Feb. 28, 2019. [Epub ahead of print].

(56) References Cited

OTHER PUBLICATIONS

Passini et al., Widespread gene delivery and structure-specific patterns of expression in the brain after intraventricular injections of neonatal mice with an adeno-associated virus vector. J Virol. Dec. 2001;75(24):12382-92.
Puccio et al., Mouse models for Friedreich ataxia exhibit cardiomyopathy, sensory nerve defect and Fe—S enzyme deficiency followed by intramitochondrial iron deposits. Nat Genet. Feb. 2001;27(2):181-6.
Gong Y et al., Intrathecal Adeno-Associated Viral Vector-Mediated Gene Delivery for Adrenomyeloneuropathy. Hum Gene Ther. May 2019;30(5):544-555. Epub Dec. 18, 2018.
Blair et al., The current state of biomarker research for Friedreich's ataxia: a report from the 2018 FARA biomarker meeting. Future Sci OA. Jun. 28, 2019;5(6):FSO398.
FXN cDNA ORF clone, Macaca mulatta (Rhesus monkey, Clone ID: OMb03022, GenScript, Apr. 24, 2016 (Apr. 24, 2016), pp. 1-3. Retrieved from the Internet: <www.genscript.com/gene/macaca-mulatta/699469/fxn.html> on Jan. 3, 2019 (Jan 3, 2019). entire document.
International Search Report received in corresponding PCT application No. PCT/US2018/053312 dated Sep. 28, 2018.
Extended European Search Report issued in European Patent Application No. 18860559.6, mailed Jun. 10, 2021, 4 pages.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neurosocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016; 136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate in Vivo Non-Invasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64. 16.
Summerford C, et al. Aavr: a multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.
Stahl Ph, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28 (4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. Nov. 22, 2014. 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90 (21):9878-9888.
Wang LL, et al. Comparative study of liver gene transfer with AAV vectors based on endogenous and engineered AAV capsids. Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Ai J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.

(56) References Cited

OTHER PUBLICATIONS

Clement N, et al. Manufacturing of recombinant adeno-associated viral vectors for clinical trials. Mol Ther Methods Clin Dev. Mar. 2016;3:16002.
D'costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24 (2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology. May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1): R2-6. doi: 10.1093/hmg/ddr141. Epub Apr. 29, 2011.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999; 73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.

Ding C, et al., Biochemical Characterization of Junonia Coenia Densovirus Nonstructural Protein NS-1. J. Virol., 76 (1):338-345 2002.
Adachi K, et al. Drawing a high-resolution functional map of adeno-associated virus capsid by massively parallel sequencing. Nat Commun. 2014;5:3075. doi: 10.1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. Siam J. Appl. Math. 48-5 (1988), pp. 1073-1082.
Devereux J A comprehensive set of sequence analysis programs for the VAX. Nucleic Acids Res. Jan. 11, 1984;12(1 Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge SM Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Chandler RJ, et al. Systemic AAV9 gene therapy improves the lifespan of mice with Niemann-Pick disease, type C1. Hum Mol Genet. Jan. 2017;26(1):52-64.
Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Neurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: a Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Gurda BL, et al. Evaluation of AAV-mediated gene therapy for central nervous system disease in canine mucopolysaccharidosis VII. Mol Ther. Feb. 2016;24(2):206-16.

(56) References Cited

OTHER PUBLICATIONS

Ahmed SS, et al. rAAV gene therapy in a Canavan's disease mouse model reveals immune impairments and an extended pathology beyond the central nervous system. Mol Ther. Jun. 2016;24(6):1030-41.
Dashkoff J, et al. Tailored transgene expression to specific cell types in the central nervous system after peripheral injection with AAV9. Mol Ther Methods Clin Dev. Dec. 2016;3:16081.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenoceptor or associated G alpha proteins to modulate skeletal muscle mass and muscle fiber size. Sci Rep. Mar. 2016;6:23042.
Greig JA, et al. Intramuscular administration of AAV overcomes pre-existing neutralizing antibodies in rhesus macaques. Vaccine. Dec. 2016;34(50):6323-6329.
Ai J, et al. Adeno-associated virus serotype rh. 10 displays strong muscle tropism following intraperitoneal delivery. Sci Rep. Jan. 2017;7:40336.
Baum BJ, et al. Advances in salivary gland gene therapy—oral and systemic implications. Expert Opinion on Biological Therapy. 2015;15(10):1443-54.
Hai B, et al. Long-term transduction of miniature pig parotid glands using serotype 2 adeno-associated viral vectors. J Gene Med. Jun. 2009;11(6):506-14.
Maniatis T. et al., Molecular Cloning. CSH Laboratory, NY, N.Y. (1982).
Merten OW, et al. Viral vectors for gene therapy and gene modification approaches. Biochem Eng J. Apr. 2016;108:98-115.
'Muzyczka N, et al. AAV's Golden Jubilee. Mol Ther. May 2015;23(5):807-8.
Philiport, et al. Liposomes as tools in Basic Research and Industry. CRC Press, Ann Arbor, Mich. (1995).
Kailasan S, et al. Parvovirus Family Conundrum: What makes a killer? Annu Rev Virol. Nov. 2015;2(1):425-50.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Myers EW, et al. Optimal alignments in linear space. Comput Appl Biosci. Mar. 1988;4(1):11-7.
Smith DW, et al. Biocomputing: Informatics and Genome Projects. Academic Press, New York, 1993.
Kozak M. Interpreting cDNA sequences: some insights from studies on translation. Mamm Genome. Aug. 1996;7 (8):563-74.
Kozak M. Point mutations define a sequence flanking the AUG initiator codon that modulates translation by eukaryotic ribosomes. Cell. Jan. 31, 1986;44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Heim R, et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8 (342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
O'reilly DR, et al. Baculovirus expression vectors: a laboratory manual. Oxford University Press, 1994.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and neonate rats. Gene Ther. Apr. 2015, 22(4):316-24.
Merkel SF et al. Trafficking of AAV Vectors Across a Model of the Blood-Brain Barrier; a Comparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016; 1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates. Mol Ther. Aug. 2015, 23(8):1298-307.
Ojala DS, et al. Adeno-associated virus vectors and neurological gene therapy. Neuroscientist. Feb. 2015;21 (1):84-98.
Katz ML, et al. AAV gene transfer delays disease onset in a TPP1-deficient canine model of the late infantile form of Batten Disease. Sci Transl Med. Nov. 2015;7(313):313ra180.
Kothari P, et al. Iodine-124 Labeled Adeno-Associated Virus: A Promising Tool for Tracking Gene Therapy. Journal of Nuclear Medicine. May 2015, 56 (supplement 3), 494-494.

(56) References Cited

OTHER PUBLICATIONS

Landegger LD, et al. A synthetic AAV vector enables safe and efficient gene transfer to the mammalian inner ear. Nat Biotechnol. Mar. 2017;35(3):280-284.

Mason JB, et al. Delivery and evaluation of recombinant adeno-associated viral vectors in the equine distal extremity for the treatment of laminitis. Equine Vet J. Jan. 2017;49(1):79-86.

Jeong D, et al. Matricellular Protein CCN5 Reverses Established Cardiac Fibrosis. J Am Coll Cardiol. Apr. 5, 2016;67 (13):1556-68.

Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.

Ibrahim S, et al. Stable liver specific expression of human IDOL in humanized mice raises plasma cholesterol. Cardiovasc Res. May 2016; 110(1):23-9.

Li Sy, et al. Efficient and targeted transduction of nonhuman primate liver with systemically delivered optimized AAV3E vectors. Mol Ther. Dec. 2015;23(12):1867-76.

Heller KN, et al. Human alpha 7 integrin gene (ITGA7) delivered by adeno-associated virus extends survival of severely affected dystrophin/utrophin deficient mice. Oct. 2015;26(10):647-56.

Mendell JR, et al. Follistatin Gene Therapy for Sporadic Inclusion Body Myositis Improves Functional Outcomes. Mol Ther. Apr. 2017;25(4):870-879.

Schnepp BC, et al. Recombinant adeno-associated virus vector genomes take the form of long-lived transcriptionally competent episomes in human muscle. Hum Gene Ther. Jan. 2016;27(1):32-42.

Murlidharan G et al. Glymphatic Fluid Transport Controls Paravascular Clearance of AAV Vectors from the Brain. UCI Insight. Sep. 8, 2016;1(14).

Neuberger Ewi, et al. Establishment of two quantitative nested qPCR assays targeting the human EPO transgene. Gene Ther. Apr. 2016;23(4):330-9.

Lentz TB, et al. Insight into the Mechanism of Inhibition of Adeno-Associated Virus by the Mre11/Rad50/Nbs1 Complex. J Virol. Jan. 2015, 89(1):181-94.

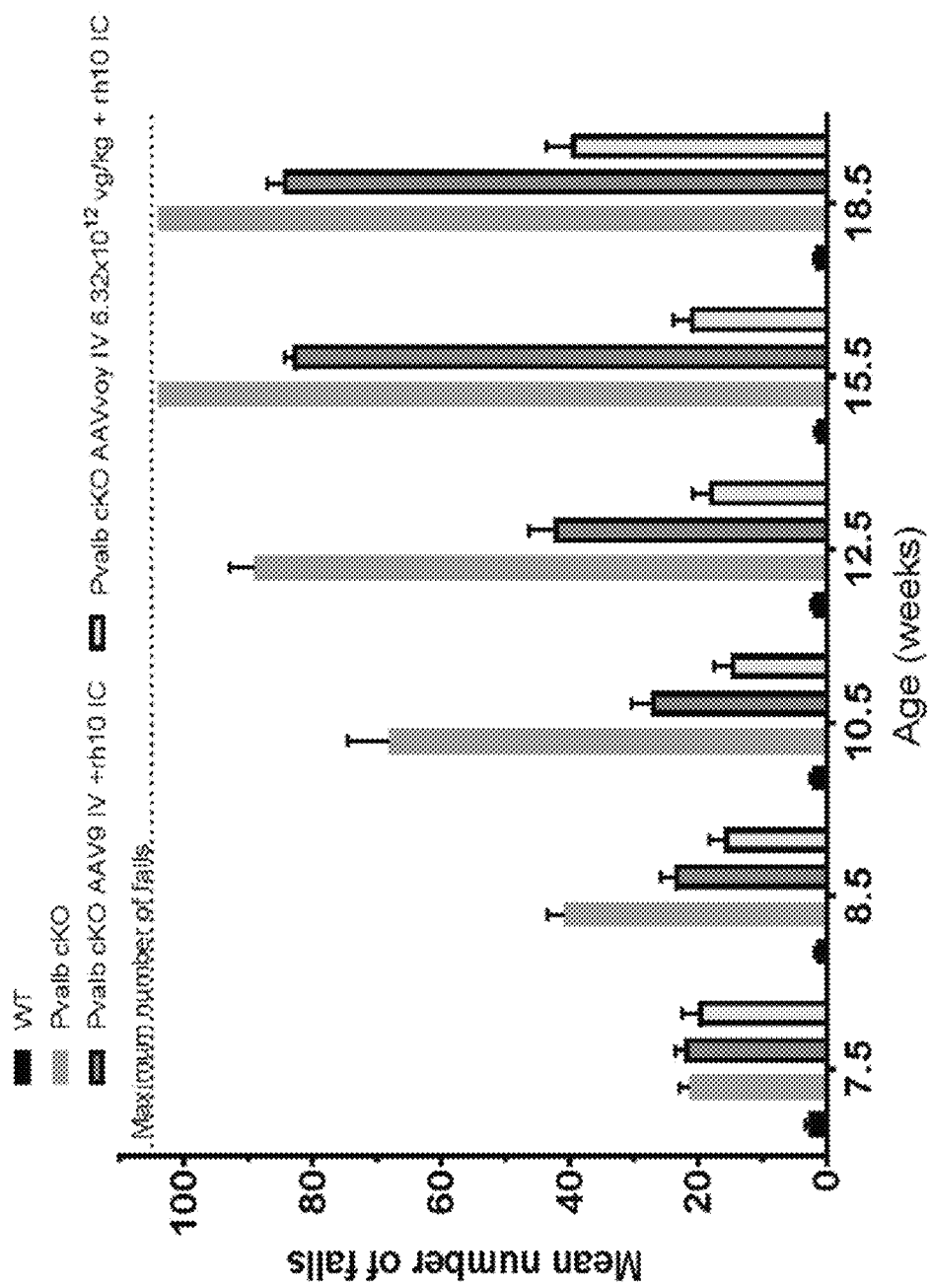

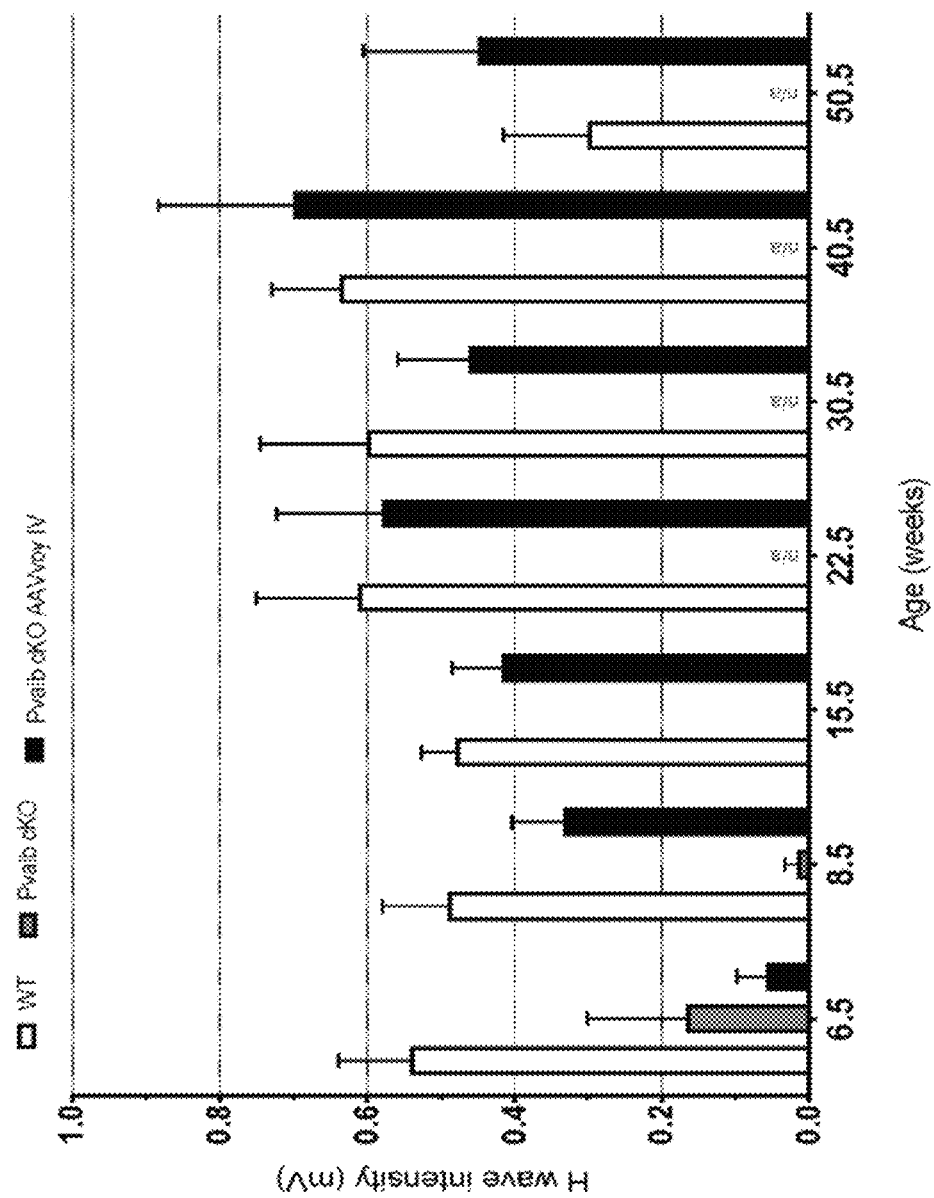

RESCUE OF CENTRAL AND PERIPHERAL NEUROLOGICAL PHENOTYPE OF FRIEDREICH'S ATAXIA BY INTRAVENOUS DELIVERY

CROSS REFERENCE TO RELATED APPLICATIONS

This application is a continuation of U.S. application Ser. No. 16/651,617, filed Mar. 27, 2020, which is a U.S. National Phase Application under 35 U.S.C. § 371 of International Application No. PCT/US2018/053312, filed Sep. 28, 2018, which claims the benefit of U.S. Provisional Patent Application No. 62/565,840, filed Sep. 29, 2017 and U.S. Provisional Patent Application No. 62/663,835, filed Apr. 27, 2018, entitled Rescue of Central and Peripheral Neurological Phenotype of Friedreich's Ataxia by Intravenous Delivery; the contents of each of which are herein incorporated by reference in their entirety.

REFERENCE TO THE SEQUENCE LISTING

The present application is being filed along with a Sequence Listing in electronic format as an XML file. The Sequence Listing is provided as an XML file entitled V2071-1054USCON1_SL, created on Aug. 29, 2022, which is 34,723 bytes in size. The Sequence Listing is incorporated by reference herein in its entirety.

FIELD OF THE INVENTION

Presented herein are compositions, methods and processes for treating Friedreich's Ataxia using adeno-associated virus (AAV) to deliver therapeutics agents.

BACKGROUND OF THE INVENTION

Use of adeno-associated virus (AAV) to deliver therapeutic agents (i.e., transgenes) to the central nervous system offers a means to achieve a widespread distribution of delivered genes in the CNS and PNS. Tissue of the CNS and PNS are highly heterogeneous and consists of different cell types including different types of neurons (e.g. excitatory and inhibitory neurons) and glial cells (e.g., oligodendrocytes, astrocytes and microglia). The characterization of different AAV capsid serotypes reveals that different AAV serotypes have different efficiency of transduction to different CNS/PNS tissues (e.g., cervical spinal cord and hippocampus) and cells (e.g., neurons or glial cells).

Studies, such as those referenced herein examining the targeting of specific tissues and cell types of the CNS/PNS by AAV capsids address one part of the problem of effective clinical treatment of CNS/PNS disorders by AAV delivery of therapeutic transgenes. The appropriate expression of the therapeutic transgene encoding the delivered payload, both temporally and spatially within the desired cell type, is critical to achieving the desired ameliorative effect. The properties of regulatory elements that drive expression of exogenous payloads from AAV genomes have not been well characterized.

On this background there remains, however, much work to be done to optimize delivery of therapeutic agents to the central nervous system. Better understanding and optimizing delivery parameters for viral particle distribution as described herein will lead to safer and more effective gene therapy. AAVs have emerged as one of the most widely studied and utilized viral particles for gene transfer to mammalian cells. See, e.g., Tratschin et al., Mol. Cell Biol., 5(11):3251-3260 (1985) and Grimm et al., Hum. Gene Ther., 10(15):2445-2450 (1999).

SUMMARY OF THE INVENTION

Provided herein is an adeno-associated virus (AAV) particle comprising a capsid and a viral genome, wherein said capsid delivers the AAV particle to a nervous system, and wherein said viral genome comprises a polynucleotide sequence encoding Frataxin and one or more microRNA binding sites.

In some embodiments, the capsid of the AAV particle is AAVvoy.

In some embodiments, the amino acid sequence of the capsid is at least 95% identical to SEQ ID NO: 2.

In some embodiments, the amino acid sequence of the capsid is at least 99% identical to SEQ ID NO: 2.

In some embodiments, the amino acid sequence of the capsid comprises SEQ ID NO: 2. In some embodiments, the amino acid sequence of the capsid is SEQ ID NO: 2.

In some embodiments, a nucleic acid sequence encoding the amino acid sequence of SEQ ID NO: 2 is at least 95% identical to SEQ ID NO: 3.

In some embodiments, a nucleic acid sequence encoding the amino acid sequence of SEQ ID NO: 2 is at least 99% identical to SEQ ID NO: 3.

In some embodiments, a nucleic acid sequence encoding the amino acid sequence of SEQ ID NO: 2 comprises SEQ ID NO: 3.

In certain aspects, presented herein is an AAV particle comprising a capsid and a viral genome, wherein said capsid delivers the AAV particle to a nervous system, wherein said viral genome comprises a polynucleotide sequence encoding Frataxin and one or more microRNA binding sites, and wherein the nucleic acid sequence of the viral genome comprises SEQ ID NO: 1.

In some embodiments, the Frataxin sequence is derived from a species selected from the group consisting of *Homo sapiens, Macaca mulatta*, and *Macaca fascicularis*.

In some embodiments, the Frataxin sequence is derived from a *Macaca fascicularis* Frataxin sequence.

In some embodiments, the Frataxin sequence is derived from a *Macaca mulatta* Frataxin sequence.

In some embodiments, the amino acid sequence of Frataxin comprises SEQ ID NO: 10. In some embodiments, the amino acid sequence of Frataxin comprises SEQ ID NO: 11. In some embodiments, the amino acid sequence of Frataxin comprises SEQ ID NO: 12.

In some embodiments, the Frataxin sequence is derived from a *Homo sapiens* Frataxin sequence.

In some embodiments, the amino acid sequence of Frataxin comprises SEQ ID NO: 4. In some embodiments, the amino acid sequence of Frataxin comprises SEQ ID NO: 5. In some embodiments, the amino acid sequence of Frataxin comprises SEQ ID NO: 6.

In some embodiments, the microRNA is miRNA-122.

In some embodiments, the viral genome comprises one, two, or three copies of miRNA-122 binding sites.

In some embodiments, the miRNA-122 binding site or sites in the viral genome are located 3' to the polynucleotide sequence encoding Frataxin.

Provided herein is a method for treating, ameliorating, and/or preventing a disorder in a subject stemming from a loss or partial loss of frataxin protein in the subject, wherein the method comprises: administering to the subject a therapeutically effective amount of a composition comprising an AAV particle comprising a capsid and a viral genome, wherein said capsid delivers the viral genome to a nervous system, and wherein said viral genome comprises a polynucleotide sequence encoding Frataxin and one or more microRNA binding sites, as described herein.

In some embodiments, the AAV particle is administered by intravenous (IV) administration. In some embodiments, the AAV particle is administered by intracerebral (IC) administration.

In some embodiments, the AAV particle is administered by intravenous (IV) administration and intracerebral (IC) administration.

In some embodiments, the AAV particle transduces nervous system structures following intravenous administration, wherein the nervous system structures are one or more regions selected from the group consisting of cerebellum and/or dorsal root ganglia (DRG).

In some embodiments, a pharmaceutical composition comprises the AAV particle.

In some embodiments, the composition is administered by intravenous (IV) administration at a dose selected from the group consisting of $2.00\times10^{12}$ vg/kg, $6.32\times10^{12}$ vg/kg, and $2.00\times10^{13}$ vg/kg.

In some embodiments, the subject is treated for the central neurological phenotype of Friedreich's Ataxia (FA).

In some embodiments, the subject is treated for the peripheral neurological phenotype of Friedreich's Ataxia (FA).

In some embodiments, the subject is treated after the onset of symptoms.

In some embodiments, the effect of treatment lasts longer than 6 months.

In some embodiments, the effect of treatment lasts longer than 10 months.

Provided herein is a pharmaceutical composition comprising an AAV particle described herein, comprising a capsid and a viral genome, wherein said capsid delivers the viral genome to a nervous system, and wherein said viral genome comprises a polynucleotide sequence encoding Frataxin and one or more microRNA binding sites.

BRIEF DESCRIPTION OF THE DRAWINGS

The foregoing and other objects, features and advantages will be apparent from the following description of particular embodiments presented herein, as illustrated in the accompanying drawings. The drawings are not necessarily to scale, emphasis instead being placed upon illustrating the principles of various embodiments described herein.

FIG. 2A shows behavioral analysis through the notched-bar test in Pvalb cKO mice treated either with AAVvoy-cFXN-HA IV (AAVvoy IV)+AAVrh10-hFXN-HA IC (rh10 IC) or with AAV9-hFXN-HA IV (AAV9 IV)+AAVrh10-hFXN-HA IC (rh10 IC), compared with Pvalb cKO mice and wild-type (WT) mice.

FIG. 10A shows long-term electromyographic (H wave intensity) measurements in Pvalb cKO mice treated post-symptomatically with intravenous AAVvoy-cFXN-HA (AAVvoy IV) at $2.00\times10^{13}$ VG/kg, compared with Pvalb cKO mice and wild-type (WT) mice until the animals reached 50.5 weeks of age.

DETAILED DESCRIPTION OF THE INVENTION

Figure 1:
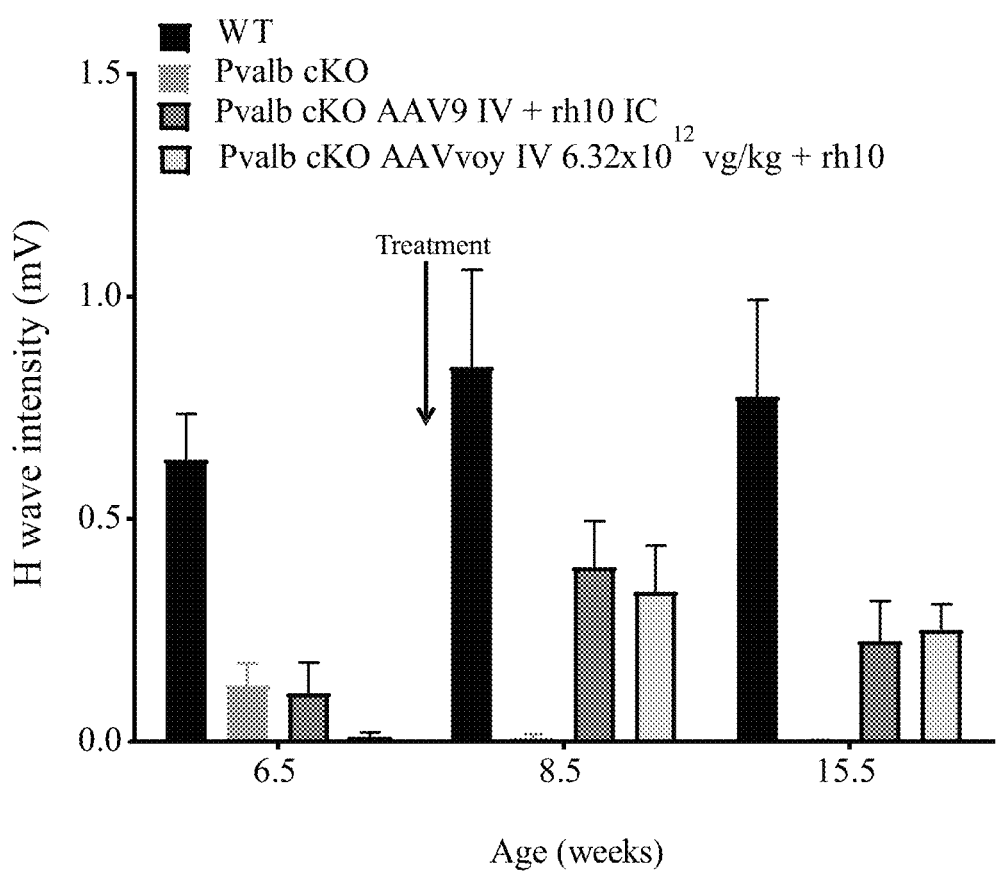
FIG. 1 shows electromyographic (H wave intensity) measurements in Pvalb cKO animals treated either with AAVvoy-cFXN-HA IV (AAVvoy IV)+AAVrh10-hFXN-HA IC (rh10 IC) or with AAV9-hFXN-HA IV (AAV9 IV)+AAVrh10-hFXN-HA IC (rh10 IC), compared with Pvalb cKO mice and wild-type (WT) mice.

The details of one or more embodiments are set forth in the accompanying description below. Although any materials and methods similar or equivalent to those described herein can be used in the practice or testing of the aspects presented herein, the preferred materials and methods are now described. Other features, objects and advantages of the subject matter presented will be apparent from the description. In the description, the singular forms also include the plural unless the context clearly dictates otherwise. Unless defined otherwise, all technical and scientific terms used herein have the same meaning as commonly understood by one of ordinary skill in the art to which this material belongs. In the case of conflict, the present description will control.

I. COMPOSITIONS

Adeno-Associated Viruses (AAVs) and AAV Particles

Viruses of the Parvoviridae family are small non-enveloped icosahedral capsid viruses characterized by a single stranded DNA genome. Parvoviridae family viruses consist of two subfamilies: Parvovirinae, which infect vertebrates, and Densovirinae, which infect invertebrates. Due to its relatively simple structure, easily manipulated using standard molecular biology techniques, this virus family is useful as a biological tool. The genome of the virus may be modified to contain a minimum of components for the assembly of a functional recombinant virus, or viral particle, which is loaded with or engineered to express or deliver a desired payload, which may be delivered to a target cell, tissue, organ, or organism.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

The Parvoviridae family comprises the Dependovirus genus which includes adeno-associated viruses (AAV) capable of replication in vertebrate hosts including, but not limited to, human, primate, bovine, canine, equine, and ovine species.

The AAV viral genome is a linear, single-stranded DNA (ssDNA) molecule approximately 5,000 nucleotides (nt) in length. The AAV viral genome can comprise a payload region and at least one inverted terminal repeat (ITR) or ITR region. ITRs traditionally flank the coding nucleotide sequences for the non-structural proteins (encoded by Rep genes) and the structural proteins (encoded by capsid genes or Cap genes). While not wishing to be bound by theory, an AAV viral genome typically comprises two ITR sequences. The AAV vector genome comprises a characteristic T-shaped hairpin structure defined by the self-complementary terminal 145 nt of the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In one embodiment, AAV particles presented herein are recombinant AAV viral vectors which are replication defective, lacking sequences encoding functional Rep and Cap proteins within their viral genome. These defective AAV particles may lack most or all parental coding sequences and essentially carry only one or two AAV ITR sequences and the nucleic acid of interest for delivery to a cell, a tissue, an organ or an organism.

In one embodiment, the viral genome of the AAV particles presented herein comprise at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

Generally, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV particles presented herein may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV viral genomes (e.g., ssAAVs), presented herein are self-complementary AAV (scAAVs) viral genomes. scAAV vector genomes contain DNA strands which anneal together to form double stranded DNA. By skipping second strand synthesis, scAAVs allow for rapid expression in the cell.

In one embodiment, a AAV particle presented herein is an scAAV.

In one embodiment, a AAV particle presented herein is an ssAAV.

Methods for producing and/or modifying AAV particles are disclosed in the art such as pseudotyped AAV particles (PCT Patent Publication Nos. WO200028004; WO200123001; WO2004112727; WO 2005005610 and WO 2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In some embodiments the capsids of the AAV particles are engineered according to the methods described in US Publication Number US 20130195801, the contents of which are incorporated herein by reference in their entirety.

In one embodiment, the AAV particles comprising a polypeptide payload region may be introduced into mammalian cells.

AAV Serotypes

AAV particles presented herein may comprise or be derived from any natural or recombinant AAV serotype. In certain embodiments, the AAV serotype is one that is useful for systemic, e.g., intravenous, delivery of AAV particles to the central and peripheral nervous systems. In a particular embodiment, the AAV serotype is AAVvoy (SEQ ID NO: 2, below). In particular embodiments, a polynucleotide encoding AAVvoy comprises the polynucleotide sequence of SEQ ID NO: 3, below.

```
                                                SEQ ID NO: 2
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

TLAVPFKAQAQTGWVQNQGILPGMVWQDRDVYLQGPIWAKIPHTDGNFH

PSPLMGGFGMKHPPPQILIKNTPVPADPPTAFNKDKLNSFITQYSTGQV

SVEIEWELQKENSKRWNPEIQYTSNYYKSNNVEFAVNTEGVYSEPRPIG

TRYLTRNL.
                                                SEQ ID NO: 3
ATGGCTGCCGATGGTTATCTTCCAGATTGGCTCGAGGACAACCTTAGTG

AAGGAATTCGCGAGTGGTGGGCTTTGAAACCTGGAGCCCCTCAACCCAA

GGCAAATCAACAACATCAAGACAACGCTCGAGGTCTTGTGCTTCCGGGT

TACAAATACCTTGGACCCGGCAACGGACTCGACAAGGGGGAGCCGGTCA

ACGCAGCAGACGCGGCGGCCCTCGAGCACGACAAGGCCTACGACCAGCA

GCTCAAGGCCGGAGACAACCCGTACCTCAAGTACAACCACGCCGACGCC

GAGTTCCAGGAGCGGCTCAAAGAAGATACGTCTTTTGGGGGCAACCTCG

GGCGAGCAGTCTTCCAGGCCAAAAAGAGGCTTCTTGAACCTCTTGGTCT

GGTTGAGGAAGCGGCTAAGACGGCTCCTGGAAAGAAGAGGCCTGTAGAG

CAGTCTCCTCAGGAACCGGACTCCTCCGCGGGTATTGGCAAATCGGGTG

CACAGCCCGCTAAAAAGAGACTCAATTTCGGTCAGACTGGCGACACAGA

GTCAGTCCCAGACCCTCAACCAATCGGAGAACCTCCCGCAGCCCCCTCA

GGTGTGGGATCTCTTACAATGGCTTCAGGTGGTGGCGCACCAGTGGCAG

ACAATAACGAAGGTGCCGATGGAGTGGGTAGTTCCTCGGGAAATTGGCA

TTGCGATTCCCAATGGCTGGGGGACAGAGTCATCACCACCAGCACCCGA

ACCTGGGCCCTGCCCACCTACAACAATCACCTCTACAAGCAAATCTCCA

ACAGCACATCTGGAGGATCTTCAAATGACAACGCCTACTTCGGCTACAG

CACCCCCTGGGGGTATTTTGACTTCAACAGATTCCACTGCCACTTCTCA

CCACGTGACTGGCAGCGACTCATCAACAACAACTGGGGATTCCGGCCTA

AGCGACTCAACTTCAAGCTCTTCAACATTCAGGTCAAAGAGGTTACGGA

CAACAATGGAGTCAAGACCATCGCCAATAACCTTACCAGCACGGTCCAG

GTCTTCACGGACTCAGACTATCAGCTCCCGTACGTGCTCGGGTCGGCTC

ACGAGGGCTGCCTCCCGCCGTTCCCAGCGGACGTTTTCATGATTCCTCA

GTACGGGTATCTGACGCTTAATGATGGAAGCCAGGCCGTGGGTCGTTCG

TCCTTTTACTGCCTGGAATATTTCCCGTCGCAAATGCTAAGAACGGGTA

ACAACTTCCAGTTCAGCTACGAGTTTGAGAACGTACCTTTCCATAGCAG

CTACGCTCACAGCCAAAGCCTGGACCGACTAATGAATCCACTCATCGAC

CAATACTTGTACTATCTCTCAAAGACTATTAACGGTTCTGGACAGAATC

AACAAACGCTAAAATTCAGTGTGGCCGGACCCAGCAACATGGCTGTCCA

GGGAAGAAACTACATACCTGGACCCAGCTACCGACAACAACGTGTCTCA

ACCACTGTGACTCAAAACAACAACAGCGAATTTGCTTGGCCTGGAGCTT

CTTCTTGGGCTCTCAATGGACGTAATAGCTTGATGAATCCTGGACCTGC

TATGGCCAGCCACAAAGAAGGAGAGGACCGTTTCTTTCCTTTGTCTGGA

TCTTTAATTTTTGGCAAACAAGGAACTGGAAGAGACAACGTGGATGCGG

ACAAAGTCATGATAACCAACGAAGAAGAAATTAAAACTACTAACCCGGT

AGCAACGGAGTCCTATGGACAAGTGGCCACAAACCACCAGAGTGCCCAA

ACTTTGGCGGTGCCTTTTAAGGCACAGGCGCAGACCGGCTGGGTTCAAA
```

-continued

```
ACCAAGGAATACTTCCGGGTATGGTTTGGCAGGACAGAGATGTGTACCT

GCAAGGACCCATTTGGGCCAAAATTCCTCACACGGACGGCAACTTTCAC

CCTTCTCCGCTGATGGGAGGGTTTGGAATGAAGCACCCGCCTCCTCAGA

TCCTCATCAAAAACACACCTGTACCTGCGGATCCTCCAACGGCCTTCAA

CAAGGACAAGCTGAACTCTTTCATCACCCAGTATTCTACTGGCCAAGTC

AGCGTGGAGATCGAGTGGGAGCTGCAGAAGGAAAACAGCAAGCGCTGGA

ACCCGGAGATCCAGTACACTTCCAACTATTACAAGTCTAATAATGTTGA

ATTTGCTGTTAATACTGAAGGTGTATATAGTGAACCCCGCCCCATTGGC

ACCAGATACCTGACTCGTAATCTGTAA..
```

Payloads: Nucleic Acids Encoding Frataxin (FXN)

The AAV particles of the present disclosure comprise at least one frataxin payload region. As used herein, "payload" or "payload region" refers to one or more polynucleotides or polynucleotide regions encoded by or within a viral genome or an expression product of such polynucleotide or polynucleotide region, e.g., a human or a primate frataxin protein.

The payload region may be constructed in such a way as to reflect a region similar to or mirroring the natural organization of an mRNA.

The payload region may comprise a combination of coding and non-coding nucleic acid sequences.

In one embodiment, the AAV particle comprises a viral genome with a payload region comprising nucleic acid sequences encoding more than one polypeptide of interest. In such an embodiment, a viral genome encoding more than one polypeptide may be replicated and packaged into a viral particle. A target cell transduced with a viral particle comprising more than one polypeptide may express each of the polypeptides in a single cell.

As a non-limiting example, the payload region may encode a human or a primate frataxin protein, or fragment or variant thereof. In some embodiments, the AAV particles are useful in the field of medicine for the treatment, prophylaxis, palliation or amelioration of Friedreich's ataxia, or any disease stemming from a loss or partial loss of frataxin protein or loss of frataxin function.

In one embodiment, the payload region of the AAV particle comprises one or more nucleic acid sequences encoding frataxin (FXN).

In one embodiment, the payload region of the AAV particle comprises a nucleic acid sequence encoding an amino acid sequence, or fragment thereof, described in Table 1.

In one embodiment, the payload region of the AAV particle comprises a nucleic acid, or fragment thereof, described in Table 1.

TABLE 1

Representative Frataxin Sequences

| SEQ ID NO | ID | Sequence | | | | Reference (GenBank Accession No.) |
|---|---|---|---|---|---|---|
| 4 | FXN SEQ-001 | MWTLGRRAVA GLRTDIDATC SGTLGHPGSL EDYDVSFGSG SGPKRYDWTG SSLAYSGKDA | GLLASPSPAQ TPRRASSNQR DETTYERLAE VLTVKLGGDL KNWVYSHDGV | AQTLTRVPRP GLNQIWNVKK ETLDSLAEFF GTYVINKQTP SLHELLAAEL | AELAPLCGRR QSVYLMNLRK EDLADKPYTF NKQIWLSSPS TKALKTKLDL | NP_000135.2 |
| 5 | FXN SEQ-002 | MWTLGRRAVA GLRTDIDATC SGTLGHPGSL EDYDVSFGSG RYVVDLSVMT | GLLASPSPAQ TPRRASSNQR DETTYERLAE VLTVKLGGDL GLGKTGCTPT | AQTLTRVPRP GLNQIWNVKK ETLDSLAEFF GTYVINKQTP TACPSMSCWP | AELAPLCGRR QSVYLMNLRK EDLADKPYTF NKQIWLSSPS QSSLKP | NP_852090.1 |
| 6 | FXN SEQ-003 | MWTLGRRAVA GLRTDIDATC SGTLGHPGSL EDYDVSFGSG RLTWLLWLFH | GLLASPSPAQ TPRRASSNQR DETTYERLAE VLTVKLGGDL P | AQTLTRVPRP GLNQIWNVKK ETLDSLAEFF GTYVINKQTP | AELAPLCGRR QSVYLMNLRK EDLADKPYTF NKQIWLSSPS | NP_001155178.1 |
| 7 | FXN SEQ-004 | agtctccctt ttgcacaaag tagtgctaag agctgctccc ccagggtcg ggcggcagac cgcagtagcc gcccagaccc ccccactctg tgcgacctgc ggcctcaacc atttgatgaa aggctctcta gaaacgctgg cagacaagcc tgggagtggt ggaacctatg tctggctatc ctggactggg tccctccatg | gggtcagggg caggctctcc ctgggaagtt ccacagaaga ccgcagcacc ccggagcagc ggcctcctgg tcacccgggt cggccgccgt acgccccgcc agatttggaa tttgaggaaa gatgagacca actctttagc atacacgttt gtcttaactg tgatcaacaa ttctccatcc aaaaactggg agctgctggc | tcctggttgc atttttgtta cttcctgagg gtgcctgcgg cagcgctgga atgtggactc cgtcacccag cccgcggccg ggctgcgca gcgcaagttc tgtcaaaaag tctggaactt cctatgaaag agagttttt gaggactatg tcaaactggg gcagacgcca agtggaccta tgtactccca cgcagagctc | actccgtgct aatgcacgaa tctaacctct ccagtggcca gggcggagcg tcgggcgccg cccagcccag gcagagttgg ccgacatcga gaaccaacgt cagagtgtct tgggccaccc actagcagag gaagaccttg atgtctcctt tggagatcta aacaagcaaa agcgttatga cgacggcgtg actaaagcct | NM_000144.4 |
```

TABLE 1-continued

Representative Frataxin Sequences

| SEQ ID NO | ID | Sequence | Reference (GenBank Accession No.) |
|---|---|---|---|

```
taaaaaccaa actggacttg tcttccttgg cctattccgg
aaaagatgct tgatgcccag ccccgtttta aggacattaa
aagctatcag gccaagaccc cagcttcatt atgcagctga
ggtctgtttt ttgttgttgt tgttgtttat ttttttttatt
cctgcttttg aggacagttg ggctatgtgt cacagctctg
tagaaagaat gtgttgcctc ctaccttgcc cccaagttct
gattttttaat ttctatggaa gattttttgg attgtcggat
ttcctccctc acatgatacc ccttatcttt tataatgtct
tatgcctata cctgaatata acaaccttta aaaaagcaaa
ataataagaa ggaaaaattc caggagggaa aatgaattgt
cttcactctt cattctttga aggatttact gcaagaagta
catgaagagc agctggtcaa cctgctcact gttctatctc
caaatgagac acattaaagg gtagcctaca aatgttttca
ggcttctttc aaagtgtaag cacttctgag ctctttagca
ttgaagtgtc gaaagcaact cacacgggaa gatcatttct
tatttgtgct ctgtgactgc caaggtgtgg cctgcactgg
gttgtccagg gagacctagt gctgtttctc ccacatattc
acatacgtgt ctgtgtgtat atatattttt tcaatttaaa
ggttagtatg gaatcagctg ctacaagaat gcaaaaaatc
ttccaaagac aagaaaagag gaaaaaaagc cgttttcatg
agctgagtga tgtagcgtaa caaacaaaat catggagctg
aggaggtgcc ttgtaaacat gaaggggcag ataaaggaag
gagatactca tgttgataaa gagagccctg gtcctagaca
tagttcagcc acaaagtagt tgtcccttg tggacaagtt
tcccaaattc cctggacctc tgcttcccca tctgttaaat
gagagaatag agtatggttg attcccagca ttcagtggtc
ctgtcaagca acctaacagg ctagttctaa ttccctattg
ggtagatgag gggatgacaa agaacagttt ttaagctata
taggaaacat tgttattggt gttgccctat cgtgatttca
gttgaattca tgtgaaaata atagccatcc ttggcctggc
gcggtggctc acacctgtaa tcccagcact tttggaggcc
aaggtgggtg gatcacctga ggtcaggagt tcaagaccag
cctggccaac atgatgaaac cccgtctcta ctaaaaatac
aaaaaattag ccgggcatga tggcaggtgc ctgtaatccc
agctacttgg gaggctgaag cggaagaatc gcttgaaccc
agaggtggag gttgcagtga gccgagatcg tgccattgca
ctgtaacctg ggtgactgag caaaactctg tctcaaaata
ataataacaa tataataata ataatagcca tcctttattg
taccettact gggttaatcg tattatacca cattacctca
ttttaatttt tactgacctg cactttatac aaagcaacaa
gcctccagga cattaaaatt catgcaaagt tatgctcatg
ttatattatt ttcttactta aagaaggatt tattagtggc
tgggcatggt ggcgtgcacc tgtaatccca ggtactcagg
aggctgagac gggagaattg cttgacccca ggcggaggag
gttacagtga gtcgagatcg tacctgagcg acagagcgag
actccgtctc aaaaaaaaaa aaaaggaggg tttattaatg
agaagtttgt attaatatgt agcaaaggct tttccaatgg
gtgaataaaa acacattcca ttaagtcaag ctgggagcag
tggcatatac ctatagtccc agctgcacag gaggctgaga
caggaggatt gcttgaagcc aggaattgga gatcagcctg
ggcaacacag caagatccta tctcttaaaa aaagaaaaaa
aaacctatta ataataaaac agtataaaca aaagctaaat
aggtaaaata tttttcctga aataaaatta tttttgagt
ctgatggaaa tgtttaagtg cagtaggcca gtgccagtga
gaaaataaat aacatcatac atgtttgtat gtgtttgcat
cttgcttcta ctgaaagttt cagtgcaccc cacttactta
gaactcggtg acatgatgta ctcctttatc tgggacacag
cacaaaagag gtatgcagtg gggctgctct gacatgaaag
tggaagttaa ggaatctggg ctcttatggg gtccttgtgg
gccagcccttt caggcctatt ttactttcat tttacatata
gctctaattg gtttgattat ctcgttccca aggcagtggg
agatccccat ttaaggaaag aaaaggggcc tggcacagtg
gctcatgcct gtaatcccag cactttggga ggctgaggca
agtgtatcac ctgaggtcag gagttcaaga ccagcctggc
caacatggca aaatcccgtc tctactaaaa atattaaaaa
attggctggg cgtggtggtt cgtgcctata atttcagcta
ctcaggaggc tgaggcagga gaatcgctgt aacctggggg
gtggaggttg cagtgagacg agatcatgcc acttcactcc
agcctggcca acagagccat actccgtctc aaataaataa
ataaataaat aaagggactt caaacacatg aacagcagcc
aggggaagaa tcaaaatcat attctgtcaa gcaaactgga
aaagtaccac tgtgtgtacc aatagcctcc ccaccacaga
ccctgggagc atcgcctcat ttatggtgtg gtccagtcat
ccatgtgaag gatgagtttc caggaaaagg ttattaaata
```

TABLE 1-continued

Representative Frataxin Sequences

| SEQ ID NO | ID | Sequence | Reference (GenBank Accession No.) |
|---|---|---|---|
| | | ttcactgtaa catactggag gaggtgagga attgcataat | |
| | | acaatcttag aaaactttt tttcccctt ctatttttg | |
| | | agacaggatc tcactttggc actcaggctg gaggacagtg | |
| | | gtacaatcaa agctcatggc agcctcgacc tccctgggct | |
| | | tgggcaatcc tcccacaggt gtgcacctcc atagctggct | |
| | | aatttgtgta tttttgtag agatggggtt tcaccatgtt | |
| | | gcccaggctg gtctctaaca cttaggctca agtgatccac | |
| | | ctgcctcgtc ctcccaagat gctgggatta caggtgtgtg | |
| | | ccacaggtgt tcatcagaaa gcttttcta ttatttac | |
| | | cttcttgagt gggtagaacc tcagccacat agaaaataaa | |
| | | atgttctggc atgacttatt tagctctctg gaattacaaa | |
| | | gaaggaatga ggtgtgtaaa agagaacctg ggtttttgaa | |
| | | tcacaaattt agaatttaat cgaaactctg cctcttactt | |
| | | gtttgtagac actgacagtg gcctcatgtt tttttttt | |
| | | ttaatctata aaatggagat atctaacatg ttgagcctgg | |
| | | gcccacaggc aaagcacaat cctgatgtga gaagtactca | |
| | | gttcatgaca actgttgttc tcacatgcat agcataattt | |
| | | catattcaca ttggaggact ctcccaaaa tatggatgac | |
| | | gttccctact caaccttgaa cttaatcaaa atactcagtt | |
| | | tacttaactt cgtattagat tctgattccc tggaaccatt | |
| | | tatcgtgtgc cttaccatgc ttatatttta cttgatcttt | |
| | | tgcatacctt ctaaaactat tttagccaat ttaaaatttg | |
| | | acagtttgca ttaaattata ggtttacaat atgctttatc | |
| | | cagctatacc tgccccaaat tctgacagat gcttttgcca | |
| | | cctctaaagg aagacccatg ttcatagtga tggagtttgt | |
| | | gtggactaac catgcaaggt tgccaaggaa aaatcgcttt | |
| | | acgcttccaa ggtacacact aagatgaaag taatttagt | |
| | | ccgtgtccag ttggattctt ggcacatagt tatcttctgc | |
| | | tagaacaaac taaaacagct acatgccagc aagggagaaa | |
| | | ggggaaggag gggcaaagtt ttgaaatttc atgtaaattt | |
| | | atgctgttca aaacgacgag ttcatgactt tgtgtataga | |
| | | gtaagaaatg ccttttctt tttgagacag agtcttgctc | |
| | | tgtcacccag gctggagtgc agtggcacga tctgggctca | |
| | | ctacaacctc cgcctcctgg gttcaagcaa ttctctgcct | |
| | | cagcctcccg agtagctggg attacaggtg cctgccacca | |
| | | cacccggcta atttttgtat ttttagtaga gacggggttt | |
| | | caccatcatg gccaggctgg tcttgaactc ctgacctagt | |
| | | aatccacctg cctccgcctc ccaaagtgct gggattacag | |
| | | gcgtgagcca ctgcacccag ccagaaatgc cttctaatct | |
| | | ttggtttatc ttaattagcc aggacacttg gagtgcatcc | |
| | | cgaagtacct gatcagtggc ccctttggaa tgtgtaaaac | |
| | | tcagctcact tatatccctg catccgctac agagacagaa | |
| | | tccaagctca tatgttccat cttctctggc tgtatagttt | |
| | | aaggaatgga aggcaccaga acagatttat tgaaatgttt | |
| | | attagctgaa gatttattta gacagttgag gaaaacatca | |
| | | gcacccagca gtaaaattgg ctctcaaaga ttttcttctc | |
| | | ctgtggaaag tcagacctct gaggccccat ccaggtagaa | |
| | | gtactagtgc aagaagggcc tctgctgtcc acttgtgttt | |
| | | ctgtgatctg tgggaacatt gttaacgcca catcttgacc | |
| | | tcaaattgtt tagctcctgg ccagacacgg tggctcacac | |
| | | ctgtaatccc agcactttga gaggctgagg caggtggatc | |
| | | acctgaggtt aggagttcga ggccagcctg gtcaacatgg | |
| | | taaaacccg cctctactaa aaatacaaaa attagctgac | |
| | | cgtagtggcg cacgcctgtt atcccagcta ctcgggaggc | |
| | | tgaggcagga gaattgcttg aacctgggtg gtggaggttg | |
| | | cagtgagccg agattacacc actgcactcc agcctgggtg | |
| | | acaagaggga aactccatta aaaaaatgta attcccgtgt | |
| | | ctgccatctt aagtgtaaag gtggctaaat tatatagaaa | |
| | | aataagacaa tatcatttcc caattacatt cctttcctac | |
| | | cgcactctat gatgctagct gagattttc caaagaaaa | |
| | | tggcttaaat aaaaccctaa gagaaagaaa aactttaaat | |
| | | ccctccaaag ctcaaaagta atagaaacag atgagtttgg | |
| | | agtcaggatt tctctgtaag attgcctagg ctgtgtactg | |
| | | cacatctcca ggtgccactg ttgacagaga ttataactac | |
| | | aatgtgaagt gaatggtgcc actgacagtt atgcaaaccg | |
| | | tccagagcat agccacctga tcctgctggg attcctcttg | |
| | | ccagtccatc agcagttccc cttgaaagtt tcaccaaaca | |
| | | tcccttaaat ctgccctctc ctgcccgtcc ccagtggagg | |
| | | tcctcatcat ttttcacctg cattttgca ggagctttct | |
| | | tatatccacc ttcctccttt tctctcagcc catcatctag | |
| | | ctacacagtc tccagggtaa gctttcagaa aggcaatctc | |
| | | ttgtctgtaa aacctaagca ggaccaaggc caagtttctt | |
| | | agcctgaaaa atgtgctttt ctgactgaac tgttcaggca | |
| | | ctgactctac atataattat gcttttctac cccctcacac | |

TABLE 1-continued

Representative Frataxin Sequences

| SEQ ID NO | ID | Sequence | Reference (GenBank Accession No.) |
|---|---|---|---|
| | | tcaacactt gactccagca atcccaaatc cccagatccc<br>taagtgtgct gtgctatttt cacgtggctc tcagacttgg<br>ccagtgctgt ttccatttg gtctttattc cccacatctc<br>tgcctggggg gtagattcta ccctgaaaaa tgttcttggc<br>acagccttgc aaactcctcc tccactcagc ctctgcctgg<br>atgcccttga ttgttccatg tcctcagcat accatgtttg<br>tctttcccag cactgaccta ccatgtgtca cccctgcttg<br>gctgtacctt ccatgaggct aggactatgt gtctcctttg<br>ttgactgctg ttgccctagc atcttgcaca gttccttgca<br>cacaattaga gctctataaa tgtcaaataa atgtgttata<br>attatatgtt taagatagtt gttcaaataa actctaaata<br>accccaac | |
| 8 | FXN SEQ-005 | agtctcccctt gggtcagggg tcctggttgc actccgtgct<br>ttgcacaaag caggctctcc attttttgtta aatgcacgaa<br>tagtgctaag ctgggaagtt cttcctgagg tctaacctct<br>agctgctccc ccacagaaga gtgcctgcgg ccagtggcca<br>ccaggggtcg ccgcagcacc cagcgctgga gggcggagcg<br>ggcggcagac ccggagcagc atgtggactc tcgggcgcag<br>cgcagtagcc ggcctcctgg cgtcacccag cccagcccag<br>gcccagaccc tcacccgggt cccgcggccg gcagagttgg<br>ccccactctg cggccgccgt ggcctgcgca ccgacatcga<br>tgcgacctgc acgccccgcc gcgcaagttc gaaccaacgt<br>ggcctcaacc agattttggaa tgtcaaaaag cagagtgtct<br>atttgatgaa ttgaggaaa tctggaactt tgggccacc<br>aggctctcta gatgagacca cctatgaaag actagcagag<br>gaaacgctgg actctttagc agagttttt gaagaccttg<br>cagacaagcc atacacgttt gaggactatg atgtctcctt<br>tgggagtggt gtcttaactg tcaaactggg tggagatcta<br>ggaacctatg tgatcaacaa gcagacgcca aacaagcaaa<br>tctggctatc ttctccatcc aggtatgtag tggacctaag<br>cgttatgact ggactgggaa aaactgggtg tactcccacg<br>acggcgtgtc cctccatgag ctgctggccg cagagctcac<br>taaagcctta aaaccaaac tggacttgtc ttccttggcc<br>tattccggaa aagatgcttg atgcccagcc ccgttttaag<br>gacattaaaa gctatcaggc caagacccca gcttcattat<br>gcagctgagg tctgtttttt gttgttgttg ttgtttattt<br>tttttattcc tgcttttgag gacagttggg ctatgtgtca<br>cagctctgta gaaagaatgt gttgcctcct accttgcccc<br>caagttctga tttttaattt ctatggaaga ttttttggat<br>tgtcggattt cctccctcac atgatacccc ttatcttta<br>taatgtctta tgcctatacc tgaatataac aacctttaaa<br>aaagcaaaat aataagaagg aaaaattcca ggagggaaaa<br>tgaattgtct tcactcttca ttcttgaag gatttactgc<br>aagaagtaca tgaagagcag ctggtcaacc tgctcactgt<br>tctatctcca aatgagacac attaaagggt agcctacaaa<br>tgttttcagg cttctttcaa agtgtaagca cttctgagct<br>ctttagcatt gaagtgtcga aagcaactca cacgggaaga<br>tcatttctta tttgtgctct gtgactgcca aggtgtggcc<br>tgcactgggt tgtccaggga gacctagtgc tgtttctccc<br>acatattcac atacgtgtct gtgtgtatat atatttttc<br>aatttaaagg ttagtatgga atcagctgct acaagaatgc<br>aaaaaatctt ccaaagacaa gaaaagagga aaaaaagccg<br>ttttcatgag ctgagtgatg tagcgtaaca aacaaaatca<br>tggagctgag gaggtgcctt gtaaacatga aggggcagat<br>aaaggaagga gatactcatg ttgataaaga gagccctggt<br>cctagacata gttcagccac aaagtagttg tccctttgtg<br>gacaagtttc ccaaattccc tggacctctg cttccccatc<br>tgttaaatga gagaatagag tatggttgat tcccagcatt<br>cagtggtcct gtcaagcaac ctaacaggct agttctaatt<br>ccctattggg tagatgaggg gatgacaaag aacagttttt<br>aagctatata ggaaacattg ttattggtgt tgccctatcg<br>tgatttcagt tgaattcatg tgaaaataat agccatcctt<br>ggcctggcgc ggtggctcac acctgtaatc ccagcacttt<br>tggaggccaa ggtgggtgga tcacctgagg tcaggagttc<br>aagaccagcc tggccaacat gatgaaaccc cgtctctact<br>aaaaatacaa aaaattagcc gggcatgatg gcaggtgcct<br>gtaatcccag ctactggga ggctgaagcg gaagaatcgc<br>ttgaacccag aggtggaggt tgcagtgagc cgagatcgtg<br>ccattgcact gtaacctggg tgactgagca aaactctgtc<br>tcaaaataat aataacaata taataataat aatagccatc<br>ctttattgta cccttactgg gttaatcgta ttataccaca<br>ttacctcatt ttaatttta ctgacctgca cttatacaa<br>agcaacaagc ctccaggaca ttaaaattca tgcaaagtta | NM_181425.2 |

TABLE 1-continued

Representative Frataxin Sequences

| SEQ ID NO | ID | Sequence | Reference (GenBank Accession No.) |
|---|---|---|---|

```
tgctcatgtt atattatttt cttacttaaa gaaggattta
ttagtggctg ggcatggtgg cgtgcacctg taatcccagg
tactcaggag gctgagacgg gagaattgct tgaccccagg
cggaggaggt tacagtgagt cgagatcgta cctgagcgac
agagcgagac tccgtctcaa aaaaaaaaaa aaggagggtt
tattaatgag aagtttgtat taatatgtag caaaggcttt
tccaatgggt gaataaaaac acattccatt aagtcaagct
gggagcagtg gcatatacct atagtcccag ctgcacagga
ggctgagaca ggaggattgc ttgaagccag gaattggaga
tcagcctggg caacacagca agatcctatc tcttaaaaaa
agaaaaaaaa acctattaat aataaaacag tataaacaaa
agctaaatag gtaaaatatt ttttctgaaa taaaattatt
ttttgagtct gatggaaatg tttaagtgca gtaggccagt
gccagtgaga aaataaataa catcatacat gtttgtatgt
gtttgcatct tgcttctact gaaagtttca gtgcaccca
cttacttaga actcggtgac atgatgtact cctttatctg
ggacacagca caaaagaggt atgcagtggg gctgctctga
catgaaagtg gaagttaagg aatctgggct cttatggggt
ccttgtgggc cagcccttca ggcctatttt actttcattt
tacatatagc tctaattggt ttgattatct cgttcccaag
gcagtgggag atcccccattt aaggaaagaa aaggggcctg
gcacagtggc tcatgcctgt aatcccagca ctttgggagg
ctgaggcaag tgtatcacct gaggtcagga gttcaagacc
agcctggcca acatggcaaa atcccgtctc tactaaaaat
attaaaaaat tggctgggcg tggtggttcg tgcctataat
ttcagctact caggaggctg aggcaggaga atcgctgtaa
cctgggggt ggaggttgca gtgagacgag atcatgccac
ttcactccag cctggccaac agagccatac tccgtctcaa
ataaataaat aaataaataa agggacttca aacacatgaa
cagcagccag gggaagaatc aaaatcatat tctgtcaagc
aaactggaaa agtaccactg tgtgtaccaa tagcctcccc
accacagacc ctgggagcat cgcctcattt atggtgtggt
ccagtcatcc atgtgaagga tgagtttcca ggaaaaggtt
attaaatatt cactgtaaca tactggagga ggtgaggaat
tgcataatac aatcttagaa aactttttt tcccctttct
attttttgag acaggatctc actttggcac tcaggctgga
ggacagtggt acaatcaaag ctcatggcag cctcgacctc
cctgggcttg gcaatcctc ccacaggtgt gcacctccat
agctggctaa tttgtgtatt ttttgtagag atggggtttc
accatgttgc ccaggctggt ctctaacact taggctcaag
tgatccacct gcctcgtcct cccaagatgc tgggattaca
ggtgtgtgcc acaggtgttc atcagaaagc ttttctatt
attttaacct tcttgagtgg gtagaacctc agcccacatag
aaaataaaat gttctggcat gacttattta gctctctgga
attacaaaga aggaatgagg tgtgtaaaag agaacctggg
tttttgaatc acaaatttag aattaatcg aaactctgcc
tcttacttgt ttgtagacac tgacagtggc ctcatgtttt
ttttttttt aatctataaa atggagatat ctaacatgtt
gagcctgggc ccacaggcaa agcacaatcc tgatgtgaga
agtactcagt tcatgacaac tgttgttctc acatgcatag
cataatttca tattcacatt ggaggacttc tcccaaaata
tggatgacgt tccctactca accttgaact taatcaaaat
actcagttta cttaacttcg tattagattc tgattccctg
gaaccattta tcgtgtgcct taccatgctt atattttact
tgatctttg catacccttct aaaactattt tagccaattt
aaaatttgac agtttgcatt aaattatagg tttacaatat
gctttatcca gctatacctg ccccaaattc tgacagatgc
ttttgccacc tctaaaggaa gacccatgtt catagtgatg
gagtttgtgt ggactaacca tgcaaggttg ccaaggaaaa
atcgctttac gcttccaagg tacacactaa gatgaaagta
attttagtcc gtgtccagtt ggattcttgg cacatagtta
tcttctgcta gaacaaacta aaacagctac atgccagcaa
gggagaaagg ggaaggaggg gcaaagtttt gaaatttcat
gtaaatttat gctgttcaaa acgacgagtt catgactttg
tgtatagagt aagaaatgcc ttttcttttt tgagacagag
tcttgctctg tcacccaggc tggagtgcag tggcacgatc
tgggctcact acaacctccg cctcctgggt tcaagcaatt
ctctgcctca gcctcccgag tagctgggat tacaggtgcc
tgccaccaca cccggctaat ttttgtattt ttagtagaga
cggggtttca ccatcatggc caggctggtc ttgaactcct
gacctagtaa tccacctgcc tccgcctccc aaagtgctgg
gattacaggc gtgagccact gcacccagcc agaaatgcct
tctaatcttt ggtttatctt aattagccag gacacttgga
gtgcatcccg aagtacctga tcagtggccc ctttggaatg
```

TABLE 1-continued

Representative Frataxin Sequences

| SEQ ID NO | ID | Sequence | Reference (GenBank Accession No.) |
|---|---|---|---|
| | | tgtaaaactc agctcactta tatccctgca tccgctacag<br>agacagaatc caagctcata tgttccatct tctctggctg<br>tatagtttaa ggaatggaag gcaccagaac agatttattg<br>aaatgtttat tagctgaaga tttatttaga cagttgagga<br>aaacatcagc acccagcagt aaaattggct ctcaaagatt<br>ttcttctcct gtggaaagtc agacctctga ggccccatcc<br>aggtagaagt actagtgcaa gaagggcctc tgctgtccac<br>ttgtgtttct gtgatctgtg ggaacattgt taacgccaca<br>tcttgacctc aaattgttta gctcctggcc agacacggtg<br>gctcacacct gtaatcccag cactttgaga ggctgaggca<br>ggtggatcac ctgaggttag gagttcgagg ccagcctggt<br>caacatggta aaaccccgcc tctactaaaa atacaaaaat<br>tagctggccg tagtggcgca cgcctgttat cccagctact<br>cgggaggctg aggcaggaga attgcttgaa cctgggtggt<br>ggaggttgca gtgagccgag attacaccac tgcactccag<br>cctgggtgac aagagggaaa ctccattaaa aaaatgtaat<br>tcccgtgtct gccatcttaa gtgtaaaggt ggctaaatta<br>tatagaaaaa taagacaata tcatttccca attacattcc<br>tttcctaccg cactctatga tgctagctga gattttttcca<br>aaagaaaatg gcttaaataa aaccctaaga gaaagaaaaa<br>ctttaaatcc ctccaaagct caaaagtaat agaaacagat<br>gagtttggag tcaggatttc tctgtaagat tgcctaggct<br>gtgtactgca catctccagg tgccactgtt gacagagatt<br>ataactacaa tgtgaagtga atggtgccac tgacagttat<br>gcaaaccgtc cagagcatag ccacctgatc ctgctgggat<br>tcctcttgcc agtccatcag cagttcccct tgaaagtttc<br>accaaacatc ccttaaatct gccctctcct gcccgtcccc<br>agtggaggtc ctcatcattt ttcacctgca tttttgcagg<br>agctttctta tatccacctt cctccttttc tctcagccca<br>tcatctagct acacagtctc cagggtaagc tttcagaaag<br>gcaatctctt gtctgtaaaa cctaagcagg accaaggcca<br>agtttcttag cctgaaaaat gtgcttttct gactgaactg<br>ttcaggcact gactctacat ataattatgc ttttctaccc<br>cctcacactc aacactttga ctccagcaat cccaaatccc<br>cagatcccta agtgtgctgt gctatttttca cgtggctctc<br>agacttggcc agtgctgttt ccatttttggt ctttattccc<br>cacatctctg cctgggggggt agattctacc ctgaaaaatg<br>ttcttggcac agccttgcaa actcctcctc cactcagcct<br>ctgcctggat gcccttgatt gttccatgtc ctcagcatac<br>catgttttgtc tttcccagca ctgacctacc atgtgtcacc<br>cctgcttggc tgtaccttcc atgaggctag gactatgtgt<br>ctcctttgtt gactgctgtt gccctagcat cttgcacagt<br>tccttgcaca caattagagc tctataaatg tcaaataaat<br>gtgttataat tatatgttta agatagttgt tcaaataaac<br>tctaaataac cccaac | |
| 9 | FXN SEQ-006 | agtctcccctt gggtcagggg tcctggttgc actccgtgct<br>ttgcacaaag caggctctcc attttttgtta aatgcacgaa<br>tagtgctaag ctgggaagtt cttcctgagg tctaacctct<br>agctgctccc ccacagaaga gtgcctgcgg ccagtggcca<br>ccagggggtcg ccgcagcacc cagcgctgga gggcggagcg<br>ggcggcagac ccggagcagc atgtggactc tcgggcgccc<br>cgcagtagcc ggcctcctgg cgtcacccag cccagcccag<br>gcccagaccc tcacccgggt cccgcggccg gcagagttgg<br>ccccactctg cggccgccgt ggcctgcgca ccgacatcga<br>tgcgacctgc acgccccgcc gcgcaagttc gaaccaacgt<br>ggcctcaacc agatttggaa tgtcaaaaag cagagtgtct<br>atttgatgaa tttgaggaaa tctggaactt gggccaccc<br>aggctctcta gatgagacca cctatgaaag actagcagag<br>gaaacgctgg actctttagc agagttttttt gaagaccttg<br>cagacaagcc atacacgttt gaggactatg atgtctcctt<br>tgggagtggt gtcttaactg tcaaactggg tggagatcta<br>ggaacctatg tgatcaacaa gcagacgcca aacaagcaaa<br>tctggctatc ttctccatcc aggttaacgt ggctcctgtg<br>gctgttccat ccctgaggaa aagtgaggac catgctctcc<br>aaaacaggcca tgtgctggac tacctctgtt tctgtctcct<br>gggattccaa tcagcaagtg agcaacgaag caacccagac<br>agtgtggttc ataggatggc tgggtaagtg gctgtttgtt<br>ttttccttac tgtggatatg tatcagtgaa ggaatctgta<br>gaacattctt gatgggaaca tttagtcata tcaagtcaat<br>aaattaatgt ttaggctggg | NM_001161706.1 |

TABLE 1-continued

Representative Frataxin Sequences

| SEQ ID NO | ID | Sequence | Reference (GenBank Accession No.) |
|---|---|---|---|
| 10 | FXN SEQ-007 | MWTFGRRAVAGLLASPSPAQAQTLTRAPRLAELAQLCSRRGLR TGINATCTTHHTSSNLRGLNQIRNVKRQSVYLMNLRKSGTLGH PGSLDDTTYERLAEETLDSLAEFFEDLADKPYTFEDYDVSFGS GVLTVKLGGDLGTYVINKQTPNKQIWLSSPSSGPKRYDWTGKN WVYSHDGVSLHELLGAELTKALKTKLDLSSLAYSGKDA | A0A2K5VX49 |
| 11 | FXN SEQ-008 | MWTFGRRAVAGLLASPSPAQAQTLTRAPRLAELAQLCSRRGLR TGINATRTTHHTSSNLRGLNQIRNVKRQSVYLMNLRKSGTLGH PGSLDDTTYERLAEETLDSLAEFFEDLADKPYTFEDYDVSFGS GVLTVKLGGDLGTYVINKQTPNKQIWLSSPSSGPKRYDRTGKN WVYSHDGVSLHELLGAELTKALKTKLDLSSLAYSGKDA | NP_001271967.1 |
| 12 | FXN SEQ-009 | MWTFGRRAVAGLLASPSPAQAQTLTRAPRLAELAQLCSRRGLR TGINATCTTHHTSSNLRGLNQIRNVKRQSVYLMNLRKSGTLGH PGSLDDTTYERLAEETLDSLAEFFEDLADKPYTFEDYDVSFGS GVLTVKLGGDLGTYVINKQTPNKQIWLSSPSSGPKRYDWTGKN WVYSHDGVSLHELLGAELTKALKTKLDLSSLAYSGKDA | NP_001247670.1 |

In some embodiments, the payload region may encode a frataxin protein derived from a species selected from the group consisting of, but not limited to, *Homo sapiens*, *Macaca mulatta*, and *Macaca fascicularis*.

In some embodiments, the payload region may encode a Frataxin sequence derived from a *Macaca fascicularis* Frataxin sequence.

In some embodiments, the payload region may encode a Frataxin sequence derived from a *Macaca mulatta* Frataxin sequence.

In some embodiments, the amino acid sequence of Frataxin comprises SEQ ID NO: 10. In some embodiments, the amino acid sequence of Frataxin comprises SEQ ID NO: 11. In some embodiments, the amino acid sequence of Frataxin comprises SEQ ID NO: 12.

In some embodiments, the Frataxin sequence is derived from a *Homo sapiens* Frataxin sequence.

In some embodiments, the amino acid sequence of Frataxin comprises SEQ ID NO: 4. In some embodiments, the amino acid sequence of Frataxin comprises SEQ ID NO: 5. In some embodiments, the amino acid sequence of Frataxin comprises SEQ ID NO: 6.

Sequence tags or amino acids, such as hemagglutinin (HA) of influenza virus or one or more lysines, can be added to the peptide sequences of the invention, e.g., at the N-terminal or C-terminal ends. Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble or linked to a solid support.

Viral Genome Component: Inverted Terminal Repeats (ITRs)

The AAV particles presented herein comprise a viral genome with at least one ITR region and a payload region. In one embodiment, the payload region of the AAV particle comprises one or more nucleic acid sequences encoding FXN, for example human FXN. In one embodiment, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes presented herein may be comprised of naturally occurring polynucleotide sequences or recombinantly derived polynucleotide sequences.

The ITRs may be derived from the same serotype as the capsid or a derivative thereof. The ITR may be of a different serotype than the capsid. In one embodiment, the AAV particle has more than one ITR. In a non-limiting example, the AAV particle has a viral genome comprising two ITRs. In one embodiment, the ITRs are of the same serotype as one another. In another embodiment, the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. Non-limiting examples of ITR length are 102, 105, 130, 140, 141, 142, 145 nucleotides in length, and those having at least 95% identity thereto.

In one embodiment, the ITR to ITR sequence of the viral genome is provided as SEQ ID NO: 1.

SEQ ID NO: 1
CCTGCAGGCAGCTGCGCGCTCGCTCGCTCACTGAGGCCGCCCGGGCAAA

GCCCGGGCGTCGGGCGACCTTTGGTCGCCCGGCCTCAGTGAGCGAGCGA

GCGCGCAGAGAGGGAGTGGCCAACTCCATCACTAGGGGTTCCTTGTAGT

TAATGATTAACCCGCCATGCTACTTATCTACGTAGCCATGCGTCGACAT

AACGCGTCGTTACATAACTTACGGTAAATGGCCCGCCTGGCTGACCGCC

CAACGACCCCCGCCCATTGACGTCAATAATGACGTATGTTCCCATAGTA

ACGCCAATAGGGACTTTCCATTGACGTCAATGGGTGGAGTATTTACGGT

AAACTGCCCACTTGGCAGTACATCAAGTGTATCATATGCCAAGTACGCC

CCCTATTGACGTCAATGACGGTAAATGGCCCGCCTGGCATTATGCCCAG

-continued
```
TACATGACCTTATGGGACTTTCCTACTTGGCAGTACATCTACGTATTAG

TCATCGCTATTACCATGGTGATGCGGTTTTGGCAGTACATCAATGGGCG

TGGATAGCGGTTTGACTCACGGGGATTTCCAAGTCTCCACCCCATTGAC

GTCAATGGGAGTTTGTTTTGGCACCAAAATCAACGGGACTTTCCAAAAT

GTCGTAACAACTCCGCCCCATTGACGCAAATGGGCGGTAGGCGTGTACG

GTGGGAGGTCTATATAAGCAGAGCTCGGGAGCAAGCTTCGTTTAGTGAA

CCGTCAGATCGCCTGGAGACGCCATCCACGCTGTTTTGACCTCCATAGA

AGACACCGGGACCGATCCAGCCTCCGCGGATTCGAATCCCGGCCGGGAA

CGGTGCATTGGAACGCGGATTCCCCGTGCCAAGAGTGACGTAAGTACCG

CCTATAGAGTCTATAGGCCCACAAAAAATGCTTTCTTCTTTTAATATAC

TTTTTTGTTTATCTTATTTCTAATACTTTCCCTAATCTCTTTCTTTCAG

GGCAATAATGATACAATGTATCATGCCTCTTTGCACCATTCTAAAGAAT

AACAGTGATAATTTCTGGGTTAAGGCAATAGCAATATTTCTGCATATAA

ATATTTCTGCATATAAATTGTAACTGATGTAAGAGGTTTCATATTGCTA

ATAGCAGCTACAATCCAGCTACCATTCTGCTTTTATTTTATGGTTGGGA

TAAGGCTGGATTATTCTGAGTCCAAGCTAGGCCCTTTTGCTAATCATGT

TCATACCTCTTATCTTCCTCCCACAGCTCCTGGGCAACGTGCTGGTCTG

TGTGCTGGCCCATCACTTTGGCAAAGAATTGGGATTCGAACCGGTATGT

GGACTTTCGGGCGCCGCGCAGTTGCCGGCCTCCTGGCGTCCCCGAGCCC

GGCCCAGGCCCAGACCCTCACCCGGGCCCCGCGGCTGGCAGAGTTGGCC

CAGCTCTGCAGCCGCCGGGGCTGCGCACCGGCATCAATGCGACCTGCA

CAACCCACCACACCAGTTCGAACCTCCGTGGCCTCAACCAGATTCGGAA

TGTCAAAAGGCAGAGTGTCTACTTGATGAATTTGAGGAAATCGGGAACT

TTGGGCCACCCAGGCTCTCTAGATGACACCACCTATGAAAGACTAGCAG

AGGAAACGCTGGACTCTTTAGCAGAGTTTTTTGAAGACCTTGCAGACAA

GCCATACACCTTTGAGGACTATGATGTTTCCTTTGGGAGTGGTGTCTTA

ACTGTTAAACTGGGTGGAGATCTAGGAACCTACGTGATCAACAAGCAGA

CGCCAAACAAGCAAATCTGGTTATCTTCTCCATCCAGTGGACCCAAGCG

TTATGACTGGACTGGGAAAACTGGGTGTATTCCCACGACGGCGTTTCC

CTCCATGAGCTGCTGGGCGCAGAGCTCACTAAAGCCTTAAAAACCAAAC

TGGACTTGTCTTCCTTGGCCTATTCCGGAAAAGACGCTTATCCTTATGA

CGTGCCTGACTATGCCTGATGACTCGAGCCATTGACTAGTACAAACACC

ATTGTCACACTCCACACAAACACCATTGTCACACTCCACACAAACACCA

TTGTCACACTCCACTGCAGTCAGGTCTATCCTGAGGATGGGTGGCATCC

CTGTGACCCCTCCCCAGTGCCTCTCCTGGCCCTGGAAGTTGCCACTCCA

GTGCCCACCAGCCTTGTCCTAATAAAATTAAGTTGCATCATTTTGTCTG

ACTAGGTGTCCTTCTATAATATTATGGGTGGAGGGGGGTGGTATGGAG

CAAGGGGCAAGTTGGGAAGACAACCTGTAGGGCCTGCGGGGTCTATTGG

GAACCAAGCTGGAGTGCAGTGGCACAATCTTGGCTCACTGCAATCTCCG

CCTCCTGGGTTCAAGCGATTCTCCTGCCTCAGCCTCCCGAGTTGTTGGG

ATTCCAGGCATGCATGACCAGGCTCAGCTAATTTTTGTTTTTTGGTAG
```
-continued
```
AGACGGGGTTTCACCCATATTGGCCAGGCTGGTCTCCAACTCCTAATCTC

AGGTGATCTACCCACCTTGGCCTCCCAAATTGCTGGGATTACAGGCGTG

AACCACTGCTCCCTTCCCTGTCCTTGGCCTAGGTATCGATGCTACGTAG

ATAAGTAGCATGGCGGGTTAATCATTAACTACAGAGGAACCCCTAGTGA

TGGAGTTGGCCACTCCCTCTCTGCGCGCTCGCTCGCTCACTGAGGCCGG

GCGACCAAAGGTCGCCCGACGCCCGGGCTTTGCCCGGGCGGCCTCAGTG

AGCGAGCGAGCGCGCAGCTGCCTGCAGG . .
```

Viral Genome Component: Promoters

In one embodiment, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the FXN polypeptides described herein in a target cell may require a specific promoter, including but not limited to, a promoter that is species specific, inducible, tissue-specific, or cell cycle-specific (Parr et al., *Nat. Med.* 3:1145-9 (1997); the contents of which are herein incorporated by reference in their entirety).

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, nervous system promoters which can be used to restrict expression to neurons or subtypes of neurons, astrocytes, or oligodendrocytes.

In one embodiment, the promoter is a frataxin (FXN) promoter.

In one embodiment, the promoter is a chicken β-actin (CBA) promoter.

In one embodiment, the promoter is a cytomegalovirus (CMV) promoter.

In one embodiment, the promoter is an engineered promoter.

In one embodiment, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter and (9) GFAP promoter.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles described herein to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of adenosines and uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

Any UTR from any gene known in the art may be incorporated into the viral genome of the AAV particle. These UTRs, or portions thereof, may be placed in the same orientation as in the gene from which they were selected or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTR which is not a variant of a wild type UTR.

In one embodiment, the viral genome of the AAV particle comprises UTRs which have been selected from a family of transcripts whose proteins share a common function, structure, feature or property.

Viral Genome Component: miRNA

In one embodiment, the viral genome may include at least one miRNA binding site. microRNAs (or miRNAs or miRs) are 19-25 nucleotide noncoding RNAs that bind to the sites of nucleic acid targets and down-regulate gene expression either by reducing nucleic acid molecule stability or by inhibiting translation. In one embodiment, the 3' UTR of the viral genome may be engineered to include at least one miRNA binding site.

In one embodiment, the viral genome comprises at least one sequence encoding a miRNA target site to reduce the expression of the transgene in a specific tissue. MiRNAs and their targeted tissues are well known in the art. As a non-limiting example, a miR-122 miRNA target site (miR-122TS), or tandem copies of the same, may be encoded in the viral genome to reduce the expression of the viral genome in the liver where miR-122 is abundantly expressed.

Viral Genome Component: Polyadenylation Sequence

In one embodiment, the viral genome of the AAV described herein comprises at least one polyadenylation sequence. The viral genome of the AAV particle may comprise a polyadenylation sequence between the 3' end of the payload coding sequence and the 5' end of the 3'ITR.

In one embodiment, the polyadenylation sequence or "polyA sequence" may range from absent to about 500 nucleotides in length.

Viral Genome Component: Introns

In one embodiment, the vector genome comprises at least one element to enhance the transgene target specificity and expression (See e.g., Powell et al. *Viral Expression Cassette Elements to Enhance Transgene Target Specificity and Expression in Gene Therapy,* 2015; the contents of which are herein incorporated by reference in its entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length.

Viral Genome Component: Stutter Sequences

In one embodiment, the viral genome comprises at least one element to improve packaging efficiency and expression, such as a stuffer or filler sequence. Non-limiting examples of stuffer sequences include albumin and/or alpha-1 antitrypsin. Any known viral, mammalian, or plant sequence may be manipulated for use as a stuffer sequence.

In one embodiment, the stuffer or filler sequence may be from about 100-3500 nucleotides in length.

Genome Size

In one embodiment, the AAV particle which comprises a payload described herein may be single stranded or double stranded vector genome. The size of the vector genome may be small, medium, large or the maximum size. Additionally, the vector genome may comprise a promoter and a polyA tail.

AAV Production

Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953690, 7,022,519, 7,238,26, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353 and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.,* 219:37-44 (1996); Zhao et al., *Vir.* 272:382-93 (2000); the contents of each of which are herein incorporated by reference in their entirety. In one embodiment, the AAV particles are made using the methods described in WO2015191508, the contents of which are herein incorporated by reference in their entirety.

Viral replication cells commonly used for production of recombinant AAV viral vectors include but are not limited to HEK293 cells, COS cells, HeLa cells, KB cells, and other mammalian cell lines as described in U.S. Pat. Nos. 6,156, 303, 5,387,484, 5,741,683, 5,691,176, and 5, 688,676; U.S. patent publication No. 2002/0081721, and International Patent Publication Nos. WO 00/47757, WO 00/24916, and WO 96/17947, the contents of each of which are herein incorporated by reference in their entireties.

In some embodiments, the viral genome of the AAV particle optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes as described in International application No. WO 96/23810; Heim et al., Current Biology 2:178-182 (1996); Heim et al., Proc. Natl. Acad. Sci. USA (1995); or Heim et al., Science 373:663-664 (1995); WO 96/30540, the contents of each of which are incorporated herein by reference in their entireties, are used.

II. FORMULATION AND DELIVERY

Pharmaceutical Compositions

The AAV particles presented herein may be prepared as pharmaceutical compositions. It will be understood that such compositions necessarily comprise one or more active ingredients and, most often, a pharmaceutically acceptable excipient.

Relative amounts of the active ingredient (e.g. AAV particle), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, compositions are administered to humans, human patients or subjects.

Formulations

Formulations presented herein can include, without limitation, saline, liposomes, lipid nanoparticles, polymers, peptides, proteins, cells transfected with viral vectors (e.g., for transfer or transplantation into a subject) and combinations thereof.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general, such preparatory methods include the step of associating the active ingredient with an excipient and/or one or more other accessory ingredients. As used herein, the phrase "active ingredient" generally refers either to an AAV particle carrying a payload region encoding the polypeptides described herein or to the end product encoded by a viral genome of an AAV particle as described herein.

Formulations of the AAV particles and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In one embodiment, the AAV particles described herein may be formulated in PBS with 0.001% of pluronic acid (F-68) at a pH of about 7.0.

In one embodiment, the AAV particles described herein may be formulated in 180 mM sodium chloride and 10 mM sodium phosphate with 0.001% pluronic acid.

AAV particles described herein may be formulated for CNS delivery. In some embodiments, the AAV particles may be formulated for intracerebral ("IC") delivery. In some embodiments, the AAV particles may be formulated for intravenous ("IV") delivery.

Excipients and Diluents

The AAV particles described herein can be formulated using one or more excipients or diluents to (1) increase stability; (2) increase cell transfection or transduction; (3) permit the sustained or delayed release of the payload; (4) alter the biodistribution (e.g., target the viral particle to specific tissues or cell types); (5) increase the translation of encoded protein; (6) alter the release profile of encoded protein and/or (7) allow for regulatable expression of the FXN payload.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, AAV particle formulations may comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients which may be used in the formulations described herein may be approved by the US Food and Drug Administration (FDA).

Pharmaceutical composition formulations of AAV particles disclosed herein may include cations or anions. In one embodiment, the formulations include metal cations such as, but not limited to, $Zn^{2+}$, $Ca^{2+}$, $Cu^{2+}$, $Mn^{2+}$, $Mg+$ and combinations thereof. As a non-limiting example, formulations may include polymers and complexes with a metal cation (See e.g., U.S. Pat. Nos. 6,265,389 and 6,555,525, each of which is herein incorporated by reference in its entirety).

Formulations described herein may also include one or more pharmaceutically acceptable salts. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977); the content of each of which is incorporated herein by reference in their entirety.

The term "pharmaceutically acceptable solvate," as used herein, means a compound described herein wherein molecules of a suitable solvent are incorporated in the crystal lattice. A suitable solvent is physiologically tolerable at the dosage administered. Solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

III. ADMINISTRATION AND DOSING

Administration

In one embodiment, the AAV particle may be administered to a subject (e.g., to the CNS/PNS of a subject) in a therapeutically effective amount to reduce the symptoms of neurological disease of a subject.

The AAV particles described herein may be administered by any delivery route which results in a therapeutically effective outcome. In one embodiment, the AAV particles are administered systemically, for example, intravenously. In another embodiment, the AAV particles are administered directly into the CNS, for example, intracerebrally. In a specific embodiment, the AAV particles are co-administered intravenously and directly into the CNS, for example, intracerebrally.

In one embodiment, the AAV particles described herein may be delivered by retro-orbital delivery.

In one embodiment, the AAV particles described herein may be delivered by intracerebral administration to the striatum. In another embodiment, the AAV particles described herein may be delivered by intracerebral administration to the white matter. As a non-limiting example, intracerebral administration may include delivery to the striatum and/or the white matter. Intracerebral administration may be unilateral or bilateral.

Each route of administration may be used at more than one site. As an example, intracerebral delivery may be at one site, two sites, three sites or more than three sites per subject.

In one embodiment, the AAV particles described herein may be delivered to a subject via a single route administration. In one embodiment, the AAV particles described herein may be administered via a single dose intravenous delivery. As a non-limiting example, the single dose intravenous delivery may be a one-time treatment. In the context of neurological disease, the single dose intravenous delivery can produce durable relief for subjects with a neurological disease and/or related symptoms.

In one embodiment, the AAV particles described herein may be administered via a single dose intravenous delivery to the DRG proprioceptive neurons. As a non-limiting example, the single dose intravenous delivery may be a one-time treatment. In the context of neurological disease, the single dose intravenous delivery can produce durable relief for subjects with a neurological disease and/or related symptoms.

In one embodiment, the AAV particle may be administered to the CNS/PNS in a therapeutically effective amount to improve function and/or survival for a subject with a neurological disease. As a non-limiting example, the vector may be administered intravenously.

The AAV particle may be administered in a "therapeutically effective" amount, i.e., an amount that is sufficient to alleviate and/or prevent at least one symptom associated with the disease, or provide improvement in the condition of the subject.

Delivery, Dose and Regimen

Compositions comprising AAV particles as described herein are typically formulated in unit dosage form for ease of administration and uniformity of dosage.

In one embodiment, the AAV particle may be delivered in a multi-dose regimen. The multi-dose regimen may be 2, 3, 4, 5, 6, 7, 8, 9, 10 or more than 10 doses.

In one embodiment, delivery of the compositions described herein to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions described herein to cells may comprise a total concentration per subject between about $1 \times 10^6$ VG and about $1 \times 10^{16}$ VG.

In one embodiment, the delivery comprises a composition concentration of $1.00 \times 10^{10}$ VG/kg. In one embodiment, the delivery comprises a composition concentration of $2.00 \times 10^{12}$ VG/kg. In one embodiment, the delivery comprises a composition concentration of $6.32 \times 10^{12}$ VG/kg. In one embodiment, the delivery comprises a composition concentration of $7.0 \times 10^{12}$ VG/kg. In one embodiment, the delivery comprises a composition concentration of $2.00 \times 10^{13}$ VG/kg.

In some embodiments, the AAV particle described herein may be administered to a subject using a single dose, one-time treatment. The dose of the one-time treatment may be administered by any methods known in the art and/or described herein. As used herein, a "one-time treatment" refers to a composition which is only administered one time. If needed, a booster dose may be administered to the subject to ensure the appropriate efficacy is reached.

Delivery to Cells

The present disclosure provides a method of delivering to a cell or tissue any of the above-described AAV particles, comprising contacting the cell or tissue with said AAV particle or contacting the cell or tissue with a formulation comprising said AAV particle, or contacting the cell or tissue with any of the described compositions, including pharmaceutical compositions. The method of delivering the AAV particle to a cell or tissue can be accomplished in vitro, ex vivo, or in vivo.

Delivery to Subjects

The present disclosure additionally provides a method of delivering to a subject, including a mammalian subject, any of the above-described AAV particles comprising administering to the subject said AAV particle, or administering to the subject a formulation comprising said AAV particle, or administering to the subject any of the described compositions, including pharmaceutical compositions.

Measurement of Expression

Expression of payloads from viral genomes may be determined using various methods known in the art such as, but not limited to immunochemistry (e.g., IHC), in situ hybridization (ISH), enzyme-linked immunosorbent assay (ELISA), affinity ELISA, ELISPOT, flow cytometry, immunocytology, surface plasmon resonance analysis, kinetic exclusion assay, liquid chromatography-mass spectrometry (LCMS), high-performance liquid chromatography (HPLC), BCA assay, immunoelectrophoresis, Western blot, SDS-PAGE, protein immunoprecipitation, and/or PCR.

IV. METHODS AND USES

In one aspect, the AAV particles presented herein and/or compositions comprising such AAV particles, can be used in methods for treating, ameliorating, and/or preventing a neurological disease in a subject stemming from a loss or partial loss of frataxin protein in the subject. In certain embodiments, the neurological disease is Friedreich's Ataxia (FA).

For example, presented herein is a method for treating FA in a mammalian subject, including a human subject, comprising administering to the subject an AAV particle or pharmaceutical compositions described herein.

The present disclosure provides a method for administering to a subject in need thereof, including a human subject, a therapeutically effective amount of the AAV particles described herein to prevent, slow, stop or reverse FA disease progression. As a non-limiting example, disease progression may be measured by tests or diagnostic tool(s) known to those skilled in the art. As another non-limiting example, disease progression may be measured by change in the pathological features of the brain, CSF, PNS or other tissues of the subject. As another non-limiting example, disease progression may be measured by changes in biomarkers in the brain, CSF, PNS or other tissues of the subject.

Friedreich's Ataxia (FA) is an autosomal recessive inherited disease that causes progressive damage to the nervous system. See, Parkinson et al., *Journal of Neurochemistry*, 2013, 126 (Suppl. 1), 103-117, the contents of which are herein incorporated by reference in their entirety. Onset usually occurs at puberty, and always by age 25. See, Campuzano, et al., Science, 271.5254 (Mar. 8, 1996): 1423, the contents of which are herein incorporated by reference in their entirety. FA results from the degeneration of nervous tissue in the cerebellum and the DRGs due to reduced expression of the mitochondrial protein frataxin (FXN) in sensory neurons that are essential (through connections with the cerebellum) for directing muscle movement of the arms and legs. See, Koeppen, Arnulf; *J Neurol Sci.*, 2011, April 15; 303(1-2): 1-12, the contents of which are herein incorporated by reference in their entirety. Initial symptoms include poor coordination such as gait disturbance, poor balance, leg weakness, decreased walking, impaired coordination, dysarthria, nystagmus, impaired sensation, kyphoscoliosis, and foot deformities. See, Parkinson et al., *Journal of Neurochemistry*, 2013, 126 (Suppl. 1), 103-117. The disease generally progresses until a wheelchair is required for mobility. Mortality often involves cardiac failure as a result of cardiac hypertrophy, see Tsou et al., *J Neurol Sci.* 2011 Aug. 15; 307(1-2):46-9. Incidence of FA among the Caucasian populations is between about 1 in 20,000 and about 1 in 50,000, with a deduced carrier frequency of about 1 in 120 in European populations. See, Nageshwaran and Festenstein, *Frontiers in Neurology, Vol.* 6, Art. 262 (2015); Campuzano, et al., Science, 271.5254

(Mar. 8, 1996): 1423, the contents of each of which are herein incorporated by reference in their entirety.

The expansion of an intronic GAA triplet repeat in the FXN gene is the genetic cause of reduced expression of frataxin resulting in FA. See, Parkinson et al., *Journal of Neurochemistry,* 2013, 126 (Suppl. 1), 103-117. Over time the deficiency causes the aforementioned symptoms, as well as frequent fatigue due to effects on cellular metabolism.

Delivery of AAV particles described herein may be used to treat subjects suffering from Friedreich's Ataxia. In some cases, methods presented herein may be used to treat subjects suspected of developing Friedreich's Ataxia. Delivery of AAV particles described herein may result in increased frataxin protein. Further, this increase in frataxin protein may or may not be associated with improvements in mobility.

In one embodiment, delivery of AAV particles described herein, comprising frataxin polynucleotides, may be used to treat subjects suffering from Friedreich's Ataxia.

In one embodiment, the AAV particles described herein, comprising frataxin polynucleotides, may be delivered to the dentate nucleus of the cerebellum, brainstem nuclei and/or Clarke's column of the spinal cord. Such delivery can be via systemic administration, direct administration to the CNS or particular regions of the CNS, or co-administration systemically and directly into the CNS, or particular region of the CNS. Delivery to one or more of these regions may treat and/or reduce the effects of Friedreich's Ataxia in a subject.

In one embodiment, the AAV particles described herein, comprising frataxin polynucleotides, may be delivered to the proprioceptive neurons of the dorsal root ganglia. Such delivery can be via systemic administration, direct administration to the CNS or particular regions of the CNS, or co-administation systemically and directly into the CNS or particular region of the CNS. Delivery to one or more of these regions may treat and/or reduce the effects of Friedreich's Ataxia in a subject.

In one embodiment, the AAV particles described herein, comprising frataxin polynucleotides, may be delivered to the proprioceptive neurons of the dorsal root ganglia. Such delivery can be via systemic administration, direct administration to the PNS or particular regions of the PNS, or co-administration systemically and directly into the PNS or particular region of the PNS. Delivery to one or more of these regions may treat and/or reduce the effects of Friedreich's Ataxia in a subject.

In one embodiment, the AAV particles described herein, comprising frataxin polynucleotides, may be delivered by intravenous administration to the central nervous system, peripheral nervous system, and/or peripheral organs for the treatment of Friedreich's Ataxia in a subject.

Also provided herein are methods for introducing the AAV particles described herein into cells, the method comprising introducing into said cells any of the vectors in an amount sufficient for an increase in the production of FXN mRNA and protein to occur. In some aspects, the cells may be neurons such as but not limited to, (proprioceptive) sensory neurons and dorsal root ganglia neurons.

In one embodiment, the AAV particles described herein may be delivered into specific types of targeted cells, including, but not limited to, (proprioceptive) sensory neurons and dorsal root ganglia neurons.

In one embodiment, the AAV particles described herein may be delivered to neurons in the cerebellum.

In some embodiments, the AAV particles may be used to increase FXN protein in DRG neurons. In some embodiments, the AAV particles described herein may be used to increase FXN protein in sensory neurons.

In some embodiments, a composition is administered as a solo therapeutic or as combination therapeutic for the treatment of FA.

V. DEFINITIONS

At various places in the present specification, substituents of compounds of the present disclosure are disclosed in groups or in ranges. It is specifically intended that the present disclosure include each and every individual sub-combination of the members of such groups and ranges.

Unless stated otherwise, the following terms and phrases have the meanings described below. The definitions are not meant to be limiting in nature and serve to provide a clearer understanding of certain aspects of the subject matter presented herein.

About: As used herein, the term "about" means +/−10% of the recited value.

Adeno-associated virus: The term "adeno-associated virus" or "AAV" as used herein refers to members of the dependovirus genus comprising any particle, sequence, gene, protein, or component derived therefrom.

AAV Particle: As used herein, an "AAV particle" is a virus which comprises a capsid and a viral genome with at least one payload region and at least one ITR region. AAV particles of the present disclosure may be produced recombinantly and may be based on adeno-associated virus (AAV) parent or reference sequences. AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Activity: As used herein, the term "activity" refers to the condition in which things are happening or being done. Compositions described herein may have activity and this activity may involve one or more biological events.

Administering: As used herein, the term "administering" refers to providing an agent, for example an AAV particle described herein, or composition, for example, a composition comprising an AAV particle described herein to a subject.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, an AAV particle described herein may be considered biologically active if even a portion of the encoded payload is biologically active or mimics an activity considered biologically relevant.

Capsid: As used herein, the term "capsid" refers to the protein shell of a virus particle.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in this context herein, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Conditionally active: As used herein, the term "conditionally active" refers to a mutant or variant of a wild-type polypeptide, wherein the mutant or variant is more or less active at physiological conditions than the parent polypeptide. Further, the conditionally active polypeptide may have increased or decreased activity at aberrant conditions as compared to the parent polypeptide. A conditionally active polypeptide may be reversibly or irreversibly inactivated at normal physiological conditions or aberrant conditions.

Control Elements: As used herein, "control elements", "regulatory control elements" or "regulatory sequences" refers to promoter regions, polyadenylation signals, transcription termination sequences, upstream regulatory domains, origins of replication, enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Delivery: As used herein, "delivery" refers to the act or manner of delivering an AAV particle, a compound, substance, entity, moiety, cargo or payload.

Delivery Agent: As used herein, "delivery agent" refers to any substance which facilitates, at least in part, the in vivo delivery of an AAV particle to targeted cells.

Dosing regimen: As used herein, a "dosing regimen" is a schedule of administration or physician determined regimen of treatment, prophylaxis, or palliative care.

Encapsulate: As used herein, the term "encapsulate" means to enclose, surround or encase.

Engineered: As used herein, embodiments described herein are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being used.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Formulation: As used herein, a "formulation" includes at least one AAV particle and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference in their entirety. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference in its entirety. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that a substance is substantially separated from the environment in which it was formed or detected. Partial separation can include, for example, a composition enriched in the substance or AAV particles of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Neurotropic: As used herein, "neurotropic" is defined as having selective, preferential or greater affinity and/or tropism for a neural cell than a non-neural cell.

Particle: As used herein, a "particle" is a virus comprised of at least two components, a protein capsid and a polynucleotide sequence enclosed within the capsid.

Payload: As used herein, "payload" or "payload region" refers to one or more polynucleotides or polynucleotide regions encoded by or within a viral genome or an expression product of such polynucleotide or polynucleotide region, e.g., a transgene or a polynucleotide encoding a polypeptide.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Purified: As used herein, "purify," "purified," "purification" means to make substantially pure or clear from unwanted components, material defilement, admixture or imperfection. "Purified" refers to the state of being pure. "Purification" refers to the process of making pure.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

Self-complementary viral particle: As used herein, a "self-complementary viral particle" is a particle comprised of at least two components, a protein capsid and a polynucleotide sequence encoding a self-complementary genome enclosed within the capsid.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition described herein may be administered, e.g., for experimental, diagnostic, prophylactic, and/or therapeutic purposes. Typical subjects include animals (e.g., mammals such as mice, rats, rabbits, non-human primates, and humans) and/or plants.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered that is sufficient, when administered to a subject suffering from or susceptible to disease, disorder, and/or condition, to treat, improve symptoms of, diagnose, prevent, and/or delay the onset of the disease, disorder, and/or condition.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Vector: As used herein, a "vector" is any molecule or moiety which transports, transduces or otherwise acts as a carrier of a heterologous molecule. Vectors described herein may be produced recombinantly and may be based on and/or may comprise an adeno-associated virus (AAV) parent or reference sequence. Such parent or reference AAV sequences may serve as an original, second, third or subsequent sequence for engineering vectors. In non-limiting examples, such parent or reference AAV sequences may comprise any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral genome: As used herein, a "viral genome" or "vector genome" is a polynucleotide comprising at least one inverted terminal repeat (ITR) and at least one encoded payload. A viral genome encodes at least one copy of the payload.

VI. EXAMPLES

Example 1. Production and Purification of AAV Particles

AAV particles described herein may be produced using methods known in the art, such as, for example, triple transfection or baculovirus mediated virus production. Any suitable permissive or packaging cell known in the art may be employed to produce the vectors. Mammalian cells are often preferred. Also preferred are trans-complementing packaging cell lines that provide functions deleted from a replication-defective helper virus, e.g., 293 cells or other E1a trans-complementing cells.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes.

Recombinant AAV virus particles are, in some cases, produced and purified from culture supernatants according to the procedure as described in US20160032254, the contents of which are incorporated by reference. Production may also involve methods known in the art including those using 293T cells, sf9 insect cells, triple transfection or any suitable production method.

In some cases, 293 cells are transfected with CaPO4 with plasmids required for production of AAV, i.e., AAV2 rep, an adenoviral helper construct and an ITR flanked transgene cassette. The AAV2 rep plasmid also contains the cap sequence of the particular virus being studied. Twenty-four hours after transfection, which occurs in serum containing DMEM, the medium is replaced with fresh medium with or without serum. Three (3) days after transfection, a sample is taken from the culture medium of the 293 adherent cells. Subsequently cells are scraped and transferred into a receptacle. After centrifugation to remove cellular pellet, a second sample is taken from the supernatant after scraping. Next, cell lysis is achieved by three consecutive freeze-thaw cycles (−80C to 37C). Cellular debris is removed and sample 3 is taken from the medium. The samples are quantified for AAV particles by DNase resistant genome titration by Taqman® PCR. The total production yield from such a transfection is equal to the particle concentration from sample 3.

AAV particle titers are measured according to genome copy number (genome particles per milliliter). Genome particle concentrations are based on Taqman® PCR of the vector DNA as previously reported (Clark et al. (1999) Hum. Gene Ther., 10:1031-1039; Veldwijk et al. (2002) Mol. Ther., 6:272-278).

Example 2. Correction of Peripheral Sensory Phenotype in Pvalb cKO Mice Following Intravenous Treatment with AAVvoy-cFXN-HA Vector Accompanied by Intracerebral Treatment with AAVrh10-hFXN-HA Vector Friedreich's Ataxia (FA) is caused by an intronic GAA expansion in the frataxin gene leading to significantly decreased expression of frataxin (FXN), a protein involved in mitochondrial function. Patients initially develop difficulty in walking and loss of balance due to the degeneration of large proprioceptive neurons in the peripheral dorsal root ganglia (DRG). Subsequently trunk and arm function decline because of increasing spino-cerebellar neuronal impairment. Patients become wheelchair bound and incapacitated, leading to a reduced average life span of about 40 years of age. To model the selective nature of neuronal loss in FA, a transgenic mouse was created in which FXN expression is abolished via the Cre Lox system in parvalbumin expressing cells (Pvalb FXN cKO mice; Piguet et al. (2018) Rapid and complete reversal of sensory ataxia by gene therapy in a novel model of Friedreich ataxia *Molecular Therapy*, the contents of which are herein incorporated by reference in their entirety), including large sensory proprioceptive neurons in the DRGs and cerebellar neurons. The mice showed loss of proprioceptive sensory function and progressive ataxia within weeks after birth. After symptom onset at 7.5 weeks of age, we intravenously delivered a novel adeno-associated virus capsid (AAVvoy) carrying a transgene for cynomolgus (primate) frataxin (UniProt: A0A2K5VX49, as shown in Table 1). Three dose levels were evaluated for efficacy on sensory and motor function by electromyogram, notched bar walking, rotarod and string hanging assays. In all tests, AAVVoy rapidly reduced disease progression in a dose-dependent manner compared to cKO mice. Our studies support the use of intravenous frataxin gene therapy with novel AAV capsids for central and peripheral neurological causes of FA.

A novel adeno-associated viral capsid (AAVvoy) carrying a transgene for cynomolgus (primate) frataxin with an HA-tag was engineered for intravenous treatment and widespread gene transfer. A single-stranded viral genome comprising a portion of AAV2 wild-type Inverted Terminal Repeats (ITRs), a synthetic promoter composed of CMV enhancer, a truncated CMV promoter, and a synthetic intron, *Macaca fascicularis* (cynomolgus monkey) frataxin (cFXN) with an HA-tag (HA), three tandem copies of miRNA-122 target sites (miR-122TS), and a human growth hormone polyadenylation sequence (hGHpA) was used to generate AAV particles, having a capsid serotype of AAVvoy, by triple transfection into HEK293T cells. The ITR to ITR sequence of the viral genome is provided as SEQ ID NO: 1.

A novel single-stranded AAV vector (AAVrh10) carrying a transgene for human frataxin with an HA-tag was engineered for intracerebral treatment and gene transfer.

Mice carrying the conditional allele for the frataxin gene ($Fxn^{L3/L3}$) as described previously (Puccio et al., *Nature Genetics*, 27: pages 181-186 (2001, the contents of which are herein incorporated by reference in their entirety)) were mated with B6; 129Pvalb$^{tm1(Cre)Arbr/J}$ (jax.org/strain/008069, Jackson Laboratory, Maine, USA) in order to generate $Fxn^{L3/L-}$; Pvalb$^{tm1(Cre)Arbr/J}$ (named "Pvalb cKO" thereafter) and the $Fxn^{+/L3}$ mice (named "WT" thereafter) used as controls. Animals were maintained in a temperature and humidity-controlled animal facility with a 12 h light-dark cycle and free access to water and a standard rodent chow (D03, SAFE, Villemoisson-sur-Orge, France) and supplement after 7.5 weeks of age with jellified food (gel diet A03 SAFE or Dietgel 76A clear H20). All animal procedures were approved by the local ethical committee (C2EA-17, agreements 604 and 2852) and were performed in accordance with the Guide for the Care and the Use of Laboratory Animals (US National Institutes of Health).

To evaluate the therapeutic benefit of co-administration of AAVvoy via intravenous (IV) delivery and AAVrh10 via intracerebral (IC) delivery, we first tested the rescue of proprioceptive deficit in Pvalb cKO mice.

The single-stranded AAVvoy particles were purified and formulated in 180 mM sodium chloride and 10 mM sodium phosphate with 0.001% pluronic acid, and then administered to adult Pvalb cKO mice at 7.5 weeks of age via retro-orbital injection at $6.32 \times 10^{12}$ VG/kg. Intracerebral AAVrh10 particles were injected bilaterally in the striatum and cerebral white matter at $1 \times 10^{10}$ VG/site (3 sites). A control group was treated with single-stranded AAV9-CAG-hFXN-HA at $7.0 \times 10^{12}$ VG/Kg (named "AAV9" thereafter) and intracerebral AAVrh10 particles at $1 \times 10^{10}$ VG/site (3 sites).

Electromyogram analyses were performed using the Natus UltraProS100 apparatus (Mag2Health, France). Pvalb cKO mice were anesthetized using IP injection with ketamine/xylazine (130/13 mg/kg). Animals were maintained at 37° C. throughout the electrophysiological assessment. Latency and amplitude of the spinal somatosensory evoked response (H wave) were recorded in the plantar hind paw muscle after sciatic nerve stimulation (0.1 ms and 8 mA intensity). Measurements were performed every week, two weeks or three weeks, depending on age of the mice, starting at 6.5 weeks of age.

As shown in FIG. 1, electromyographic measurements in Pvalb cKO animals treated either with AAVvoy-cFXN-HA IV ("AAVvoy IV")+AAVrh10-hFXN-HA IC ("rh10 IC") or with AAV9-hFXN-HA IV ("AAV9 IV")+AAVrh10-hFXN-HA IC ("rh10 IC") show partial restoration of the spinal somatosensory evoked response (H wave) one week after treatment indicating rapid functional recovery of large myelinated proprioceptive sensory neurons.

Example 3. Behavioral Analysis in Pvalb cKO Mice Following Intravenous Treatment with AAVvoy-cFXN-HA Vector Accompanied by Intracerebral Treatment with AAVrh10-hFXN-HA Vector To test the rescue of motor and muscular function in Pvalb cKO animals treated with post-symptomatic intravenous AAVvoy-cFXN-HA and intracerebral AAVrh10-hFXN-HA, the AAVvoy-cFXN-HA particles were administered by IV injection to adult (7.5 weeks of age) Pvalb cKO mice as described in Example 2 at $6.32 \times 10^{12}$ VG/kg, and AAVrh10-hFXN-HA particles were injected bilaterally in the striatum and cerebral white matter at $1 \times 10^{10}$ VG/site (3 sites). A control group was treated with intravenous AAV9 at $7.0 \times 10^{12}$ VG/kg and intracerebral AAVrh10-hFXN-HA particles at $1 \times 10^{10}$ VG/site (3 sites).

Behavioral experiments were conducted to evaluate motor and muscular function. Coordination was evaluated using the notched-bar test (scored number of slips of the upper or lower limbs—'falls') and the wire hanging test (measured time needed by animal to attach their hindlimbs when suspended by forelimbs) as previously described (Piguet el al. (2018) Rapid and complete reversal of sensory ataxia by gene therapy in a novel model of Friedreich ataxia Molecular Therapy; Arbogast et al. (2015). Deletion of the App-Runx1 region in mice models human partial monosomy 21. Dis. Model. Mech. 8: 623-634., the contents of each of which are herein incorporated in their entirety) but without training. General motor capacities were tested using the accelerating rotarod LE8200 (Bioseb, France) as previously described (mousephenotype.org/). Animals were scored weekly in the following order: wire-hanging test, notched-bar test, and rotarod.

Figure 2B:
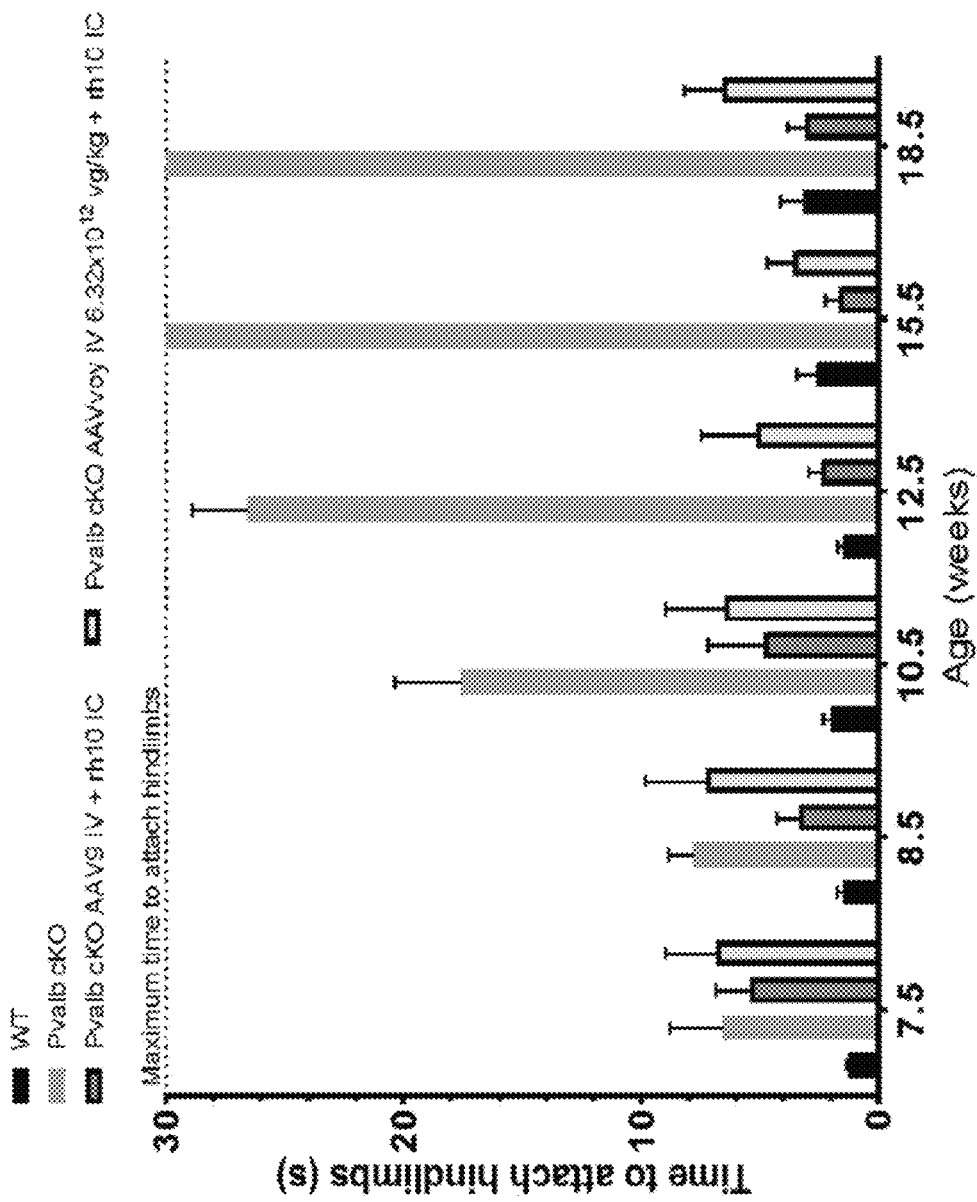
FIG. 2B shows behavioral analysis through the wire hanging test in Pvalb cKO mice treated either with AAVvoy-cFXN-HA IV (AAVvoy IV)+AAVrh10-hFXN-HA IC (rh10 IC) or with AAV9-hFXN-HA IV (AAV9 IV)+AAVrh10-hFXN-HA IC (rh10 IC), compared with Pvalb cKO mice and wild-type (WT) mice.
Figure 2C:
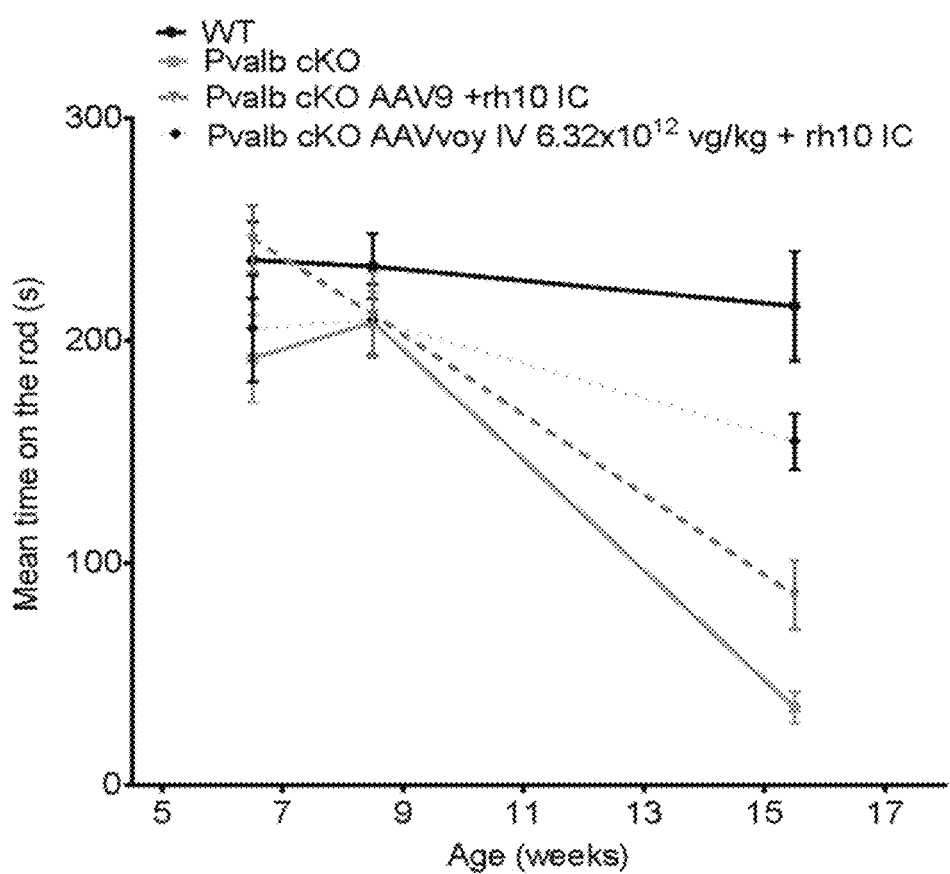
FIG. 2C shows behavioral analysis through the rotarod test in Pvalb cKO mice treated either with AAVvoy-cFXN-HA IV (AAVvoy IV)+AAVrh10-hFXN-HA IC (rh10 IC) or with AAV9-hFXN-HA IV (AAV9 IV)+AAVrh10-hFXN-HA IC (rh10 IC), compared with Pvalb cKO mice and wild-type (WT) mice.

In all tests, IV AAVvoy-cFXN-HA co-administered with IC AAVrh10-hFXN-HA rapidly reduced disease progression compared to Pvalb cKO mice. Effects of AAVvoy-cFXN-HA lasted throughout the study. As shown in FIG. 2A, FIG. 2B and FIG. 2C, post-symptomatic IV AAVvoy-cFXN-HA co-administered with IC AAVrh10-hFXN-HA rescued the notched-bar test deficit, wire hanging test deficit, and rotarod deficit, respectively. Unlike AAV9, AAVvoy-cFXN-HA leads to an almost complete rescue of the cerebellar phenotype assessed by notched-bar walking and rotarod tests.

Example 4. In Vivo Mouse Biodistribution and Expression Levels of Vector Genome Following Intravenous Treatment with AAVvoy-cFXN-HA Vector Accompanied by Intracerebral Treatment with AAVrh10-hFXN-HA Vector To test in vivo biodistribution of vector genomes and expression levels of frataxin transgenes in Pvalb cKO animals treated post-symptomatically with intravenous AAVvoy-cFXN-HA and intracerebral AAVrh10-hFXN-HA, the AAVvoy-cFXN-HA particles were administered by IV injection to adult (7.5 weeks of age) Pvalb cKO mice as described in Example 2 at $6.32 \times 10^{12}$ VG/kg, and AAVrh10-hFXN-HA particles were injected in the striatum and cerebral white matter at $1 \times 10^{10}$ VG/site (3 sites). A control group was treated with intravenous AAV9 at $7.0 \times 10^{12}$ VG/kg and intracerebral AAVrh10-hFXN-HA particles at $1 \times 10^{10}$ VG/site (3 sites).

Eleven weeks following administration, mice were euthanized by IP injection of ketamine-xylazine (300 mg/kg; 30 mg/kg), and perfused with 10 ml phosphate buffered saline, and samples for molecular analyses were immediately frozen in isopentane chilled on dry ice. Vector genome (VG) copy number was measured by quantitative digital PCR on extracted genomic DNA from pooled thoracic DRGs, heart and liver using Taqman assays targeting either the CMV promoter or the transgene. The results (vector genome copy number per diploid cell, VG/DC) were expressed as n-fold differences in the transgene sequence copy number relative to the If rC gene copy as internal standard (number of viral genome copy for 2N genome). cFXN protein levels were measured by ELISA and reported in ng cFXN/mg of total protein. Results are shown in FIGS. 3A and 3B for VG/DC and Frataxin-HA protein levels, respectively.

Figure 3A:
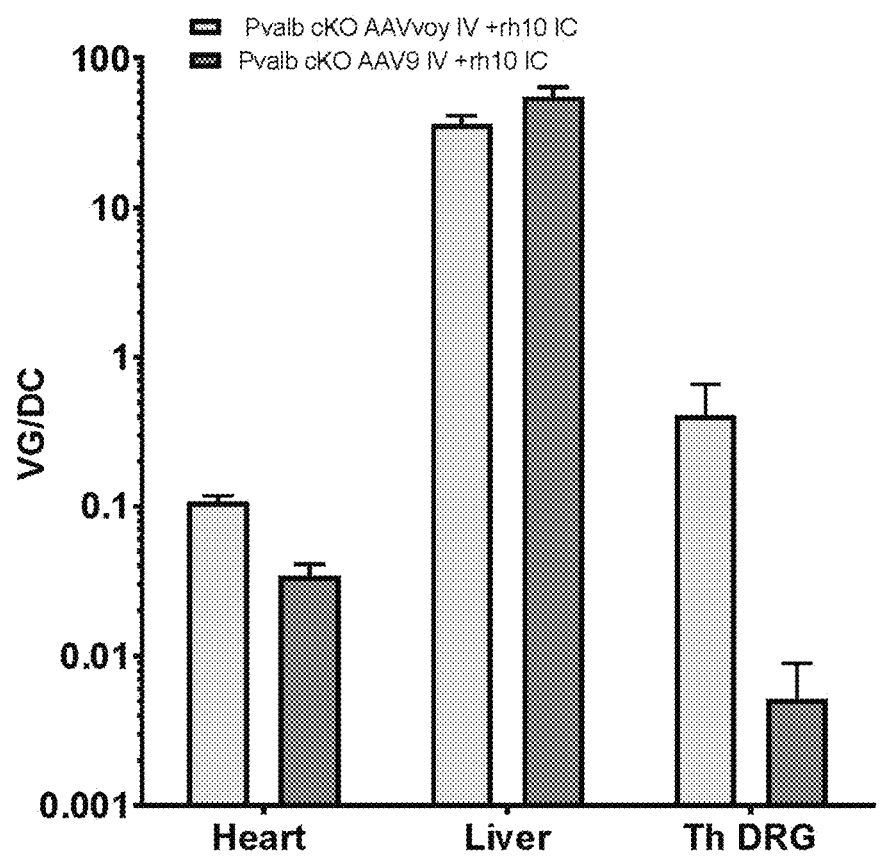
FIG. 3A shows vector genome distribution (vector genomes per diploid cell, VG/DC) in Pvalb cKO animals treated post-symptomatically with intravenous AAVvoy-cFXN-HA (AAVvoy IV) and intracerebral AAVrh10-hFXN-HA (rh10 IC), compared with intravenous AAV9-hFXN-HA (AAV9 IV) and intracerebral AAVrh10-hFXN-HA (rh10 IC) in mouse thoracic DRG (Th DRG), heart and liver.

As shown in FIG. 3A, more abundant vector genome distribution of AAVvoy-cFXN-HA compared with AAV9 was observed in mouse DRGs and heart. AAVvoy-cFXN-HA displays almost two orders of magnitude greater biodistribution to DRG, and approximately 3-fold greater distribution to heart than AAV9. Vector genome copy numbers were comparable in the liver for AAVvoy-cFXN-HA and AAV9.

Figure 3B:
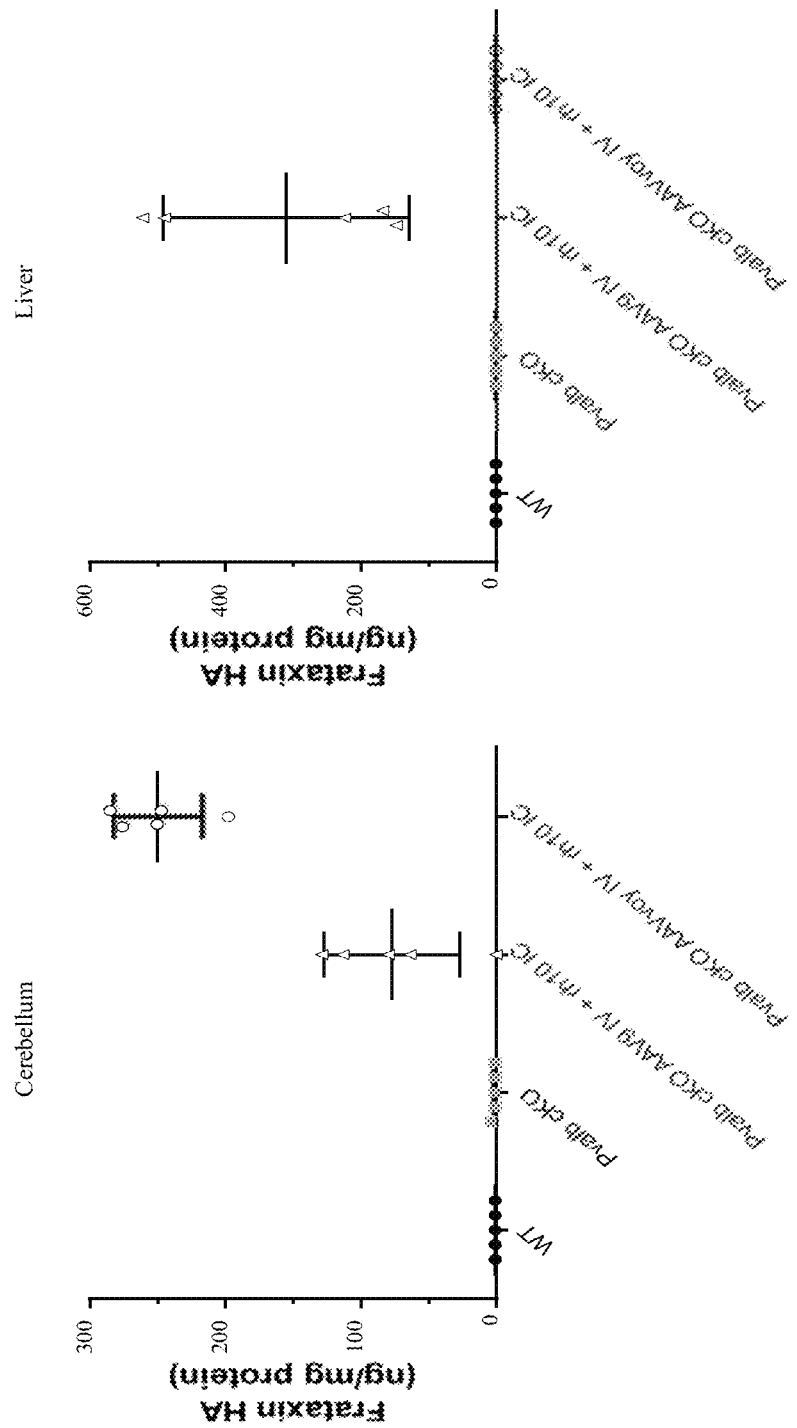
FIG. 3B shows levels of Frataxin-HA protein in cerebellum and liver of Pvalb cKO animals treated post-symptomatically with intravenous AAVvoy-cFXN-HA (AAVvoy IV) and intracerebral AAVrh10-hFXN-HA (rh10 IC) or with AAV9-hFXN-HA (AAV9 IV) and intracerebral AAVrh10-hFXN-HA (rh10 IC), compared with Pvalb cKO mice and wild-type (WT) mice.

As shown in FIG. 3B, IV AAVvoy-cFXN-HA co-administered with IC AAVrh10-hFXN-HA resulted in more than 3-fold higher cFXN protein expression in the cerebellum than IV AAV9 co-administered with IC AAVrh10-hFXN-HA. Liver was successfully de-targeted by AAVvoy-cFXN-HA, which contains three tandem copies of miRNA-122 target sites (miR-122TS), unlike AAV9-hFXN-HA.

Example 5. In Vivo Histological Analysis in Pvalb cKO Mice Following Intravenous Treatment with AAVvoy-cFXN-HA Vector Accompanied by Intracerebral Treatment with AAVrh10-hFXN-HA Vector For histological analyses, treated mice were euthanized at an age of 18.5 weeks by IP injection of ketamine-xylazine (300/13 mg/kg) and perfused with 10 mL of Phosphate Buffer Saline (PBS). Various tissues were dissected, and either fixed in PFA and embedded in paraffin, or directly embedded in Shandon Cryomatrix embedding resin (ThermoFisher Scientific) and snap-frozen in isopentane chilled on dry ice. For DRG analysis, prior to the paraffin embedding, the column was decalcified in ethylene-diamine-tetra acetic 0.34M, pH 7.4 (EDTA) for 14 days.

HA immunodetection was performed on paraffin sections using Vectastain ABC kit followed diaminobenazdine (DAB) enhancement according to the manufacturer's protocol (Vector Labs), with slight modification including epitope unmasking in 10 mM Tris, 1 mM EDTA, 0.1% tween20 at pH 8.75 for 45 min at 95° C. Images were acquired on a Hamamatsu NanoZoomer 2.0 slide scanner. All experiments were performed blinded.

Figure 4:
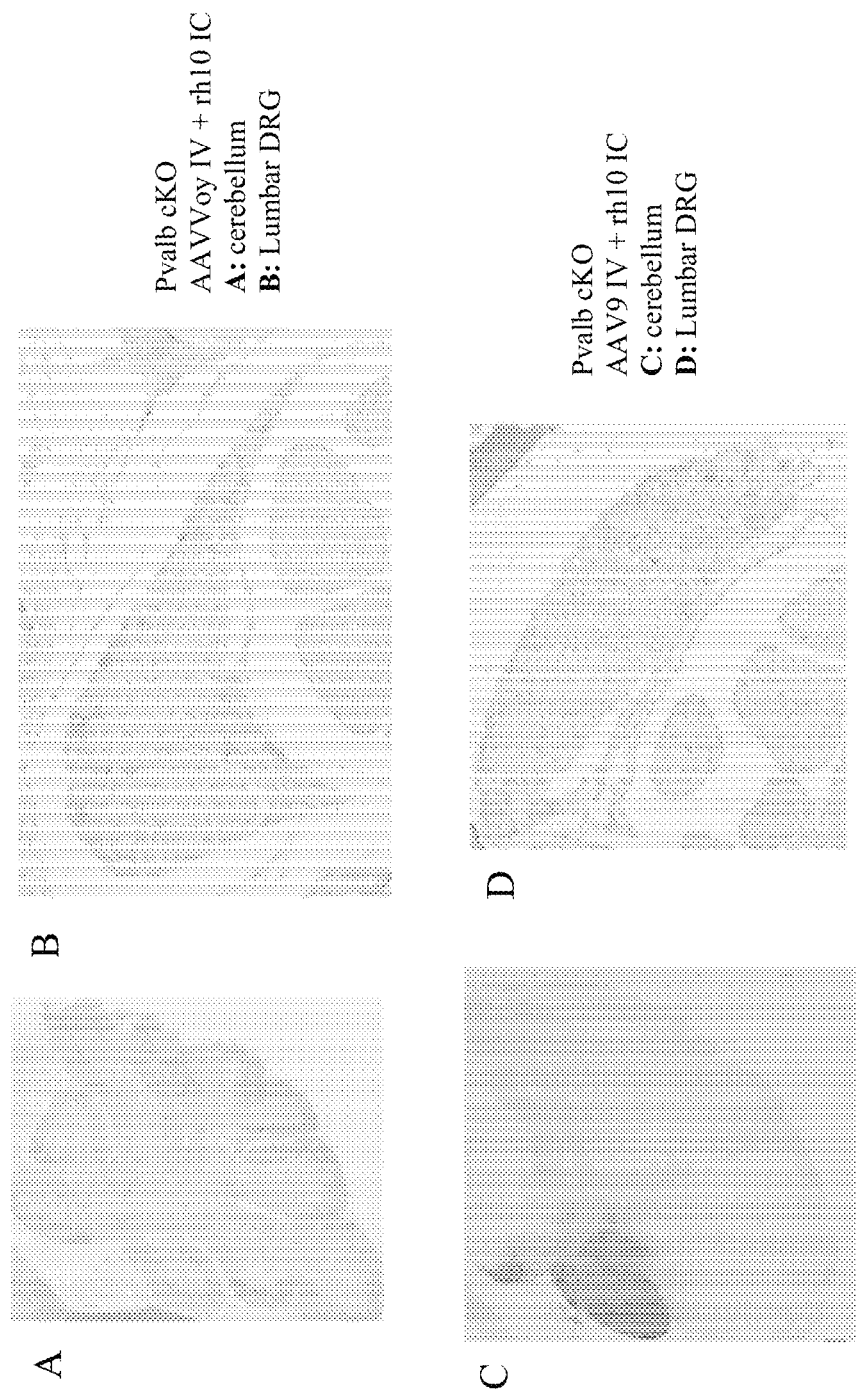
FIG. 4 shows immunohistological analysis of transgene (HA) expression in cerebellum (FIGS. 4A and 4C) and lumbar DRG (FIGS. 4B and 4D) of Pvalb cKO animals treated post-symptomatically with intravenous AAVvoy-cFXN-HA (AAVvoy IV) and intracerebral AAVrh10-hFXN-HA (rh10 IC) compared with intravenous AAV9-hFXN-HA (AAV9 IV) and intracerebral AAVrh10-hFXN-HA (rh10 IC).

As shown in FIG. 4, staining for the HA-tag showed that in combination with IC treatment with AAVrh10-hFXN-HA, IV AAVvoy-cFXN-HA treatment resulted in greater expression of transgene in cerebellum and DRG neurons than IV AAV9.

Example 6. Prevention of Sensory Neuronal Loss in Pvalb cKO Mice Following Intravenous Treatment with AAVvoy-cFXN-HA Vector Accompanied by Intracerebral Treatment with AAVrh10-hFXN-HA Vector For histological analyses, lumbar DRG tissue samples were prepared as described in Example 5. The Hematoxylin and Eosin stain was performed, and the number of sensory neurons was manually counted in a fixed area. This process was repeated until more than 1200 sensory neurons were counted for each animal. The results are presented as mean number of neurons per area.

Figure 5:
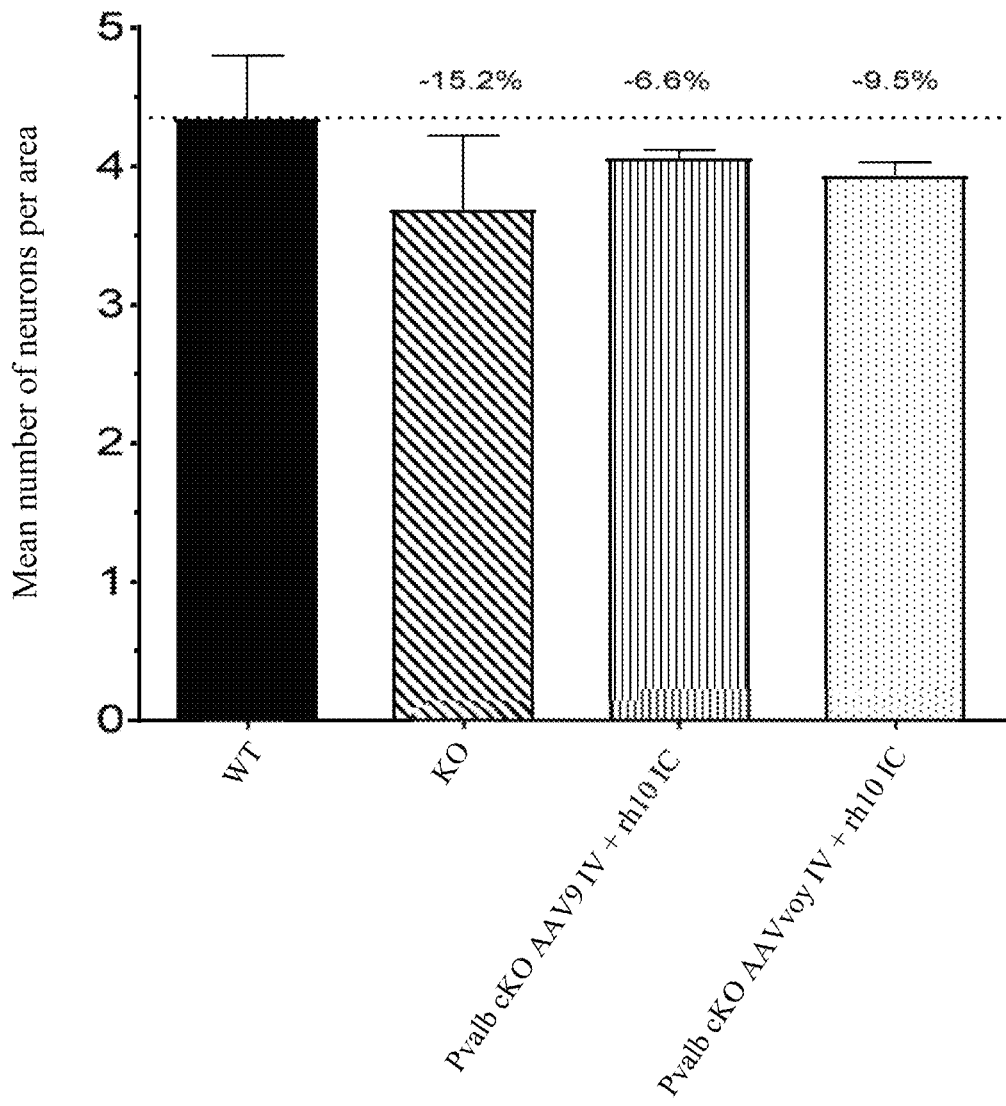
FIG. 5 shows mean number of sensory neurons in lumbar DRG tissue samples of Pvalb cKO animals treated post-symptomatically with intravenous AAVvoy-cFXN-HA (AAVvoy IV) and intracerebral AAVrh10-hFXN-HA (rh10 IC) or with intravenous AAV9-hFXN-HA (AAV9 IV) and intracerebral AAVrh10-hFXN-HA (rh10 IC), compared with Pvalb cKO mice and wild-type (WT) mice.

As shown in FIG. 5, post-symptomatic IV treatment with AAVvoy-cFXN-HA vector, in combination with IC treatment with AAVrh10-hFXN-HA, reduced neuronal loss within lumbar DRG (non-significant, n=3) from 15.2% loss in Pvalb cKO mice to 6.6% loss or 9.5% loss in AAV9 or AAVvoy-cFXN-HA — treated Pvalb cKO mice, respectively. The effects of IV AAVvoy-cFXN-HA vector treatment and IV AAV9 treatment on reducing neuronal loss in lumbar DRG are comparable.

Example 7. Dose-Dependent Behavioral Rescue and FXN-HA Expression from Intravenous Treatment with AAVvoy-cFXN-HA Vector Accompanied by Intracerebral Treatment with AAVrh10-hFXN-HA Vector of Pvalb cKO Mice To test the dose response to post-symptomatic IV AAVvoy-cFXN-HA, various IV doses of AAVvoy-cFXN-HA particles in combination with a fixed dose of IC AAVrh10-hFXN-HA were administered to adult (7.5 weeks of age) Pvalb cKO mice as described in Example 2. The IV doses of AAVvoy-cFXN-HA tested were $2.00 \times 10^{12}$ VG/kg, $6.32 \times 10^{12}$ VG/kg, and $2.00 \times 10^{13}$ VG/kg. AAVrh10-hFXN-HA particles were injected in the striatum and cerebral white matter at $1 \times 10^{10}$ VG/site (3 sites). A control group was treated with IV AAV9 particles at $7.0 \times 10^{12}$ VG/kg in combination with IC AAVrh10-hFXN-HA at $1 \times 10^{10}$ VG/site (3 sites).

Figure 6A:
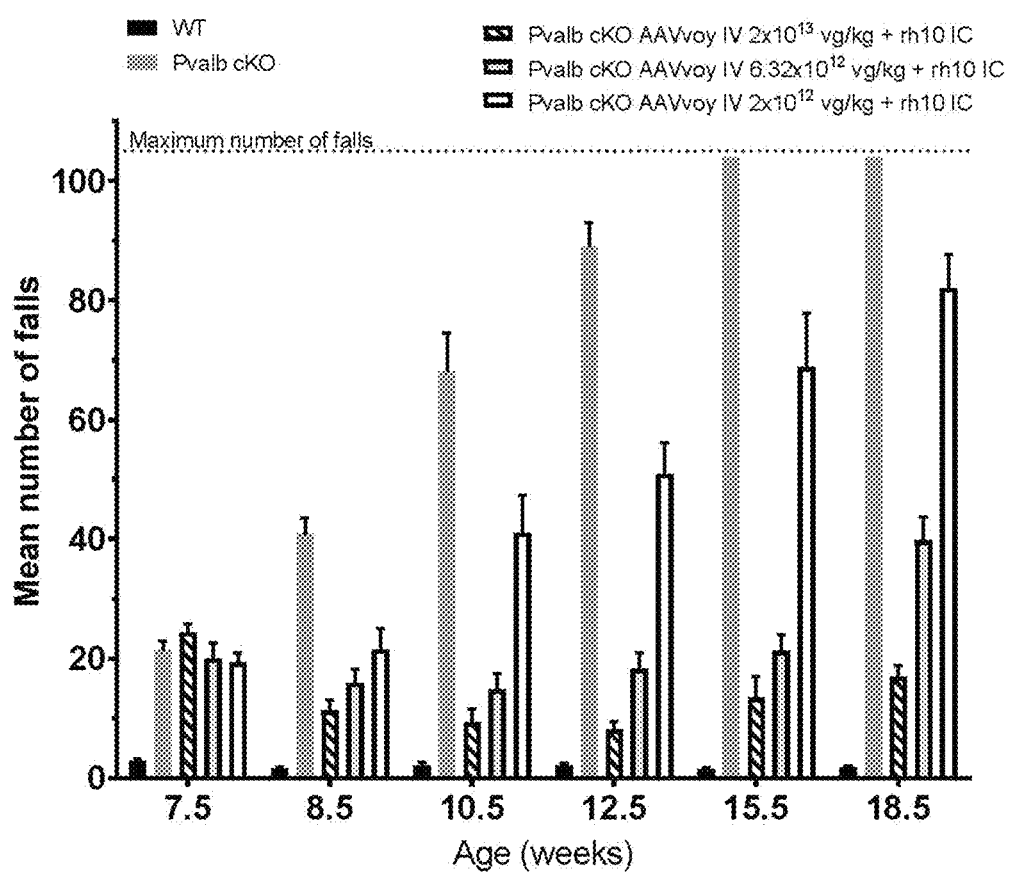
FIG. 6A shows dose-dependent behavioral rescue in the notched-bar test in Pvalb cKO mice treated post-symptomatically with $2.00\times10^{12}$ VG/kg, $6.32\times10^{12}$ VG/kg, or $2.00\times10^{13}$ VG/kg of AAVvoy-cFXN-HA IV (AAVvoy IV)+AAVrh10-hFXN-HAIC (rh10 IC), compared with Pvalb cKO mice and wild-type (WT) mice.
Figure 6B:
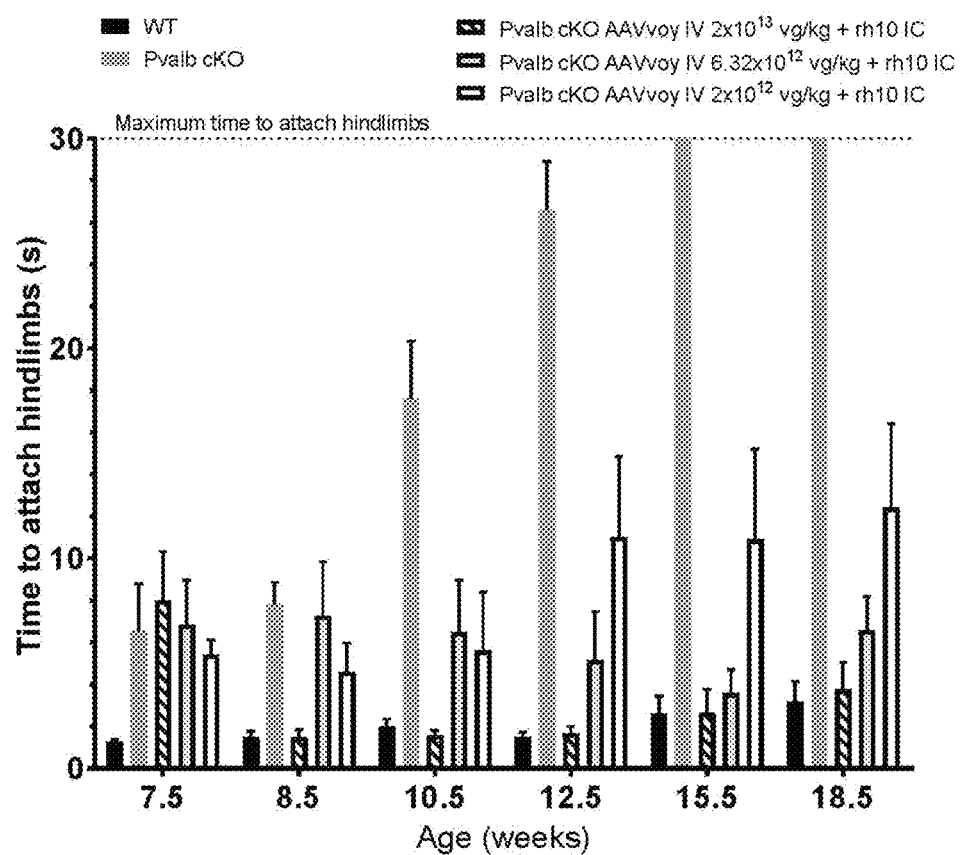
FIG. 6B shows dose-dependent behavioral rescue in the wire hanging test in Pvalb cKO mice treated post-symptomatically with $2.00\times10^{12}$ VG/kg, $6.32\times10^{12}$ VG/kg, or $2.00\times10^{13}$VG/kg of AAVvoy-cFXN-HA IV (AAVvoy IV)+AAVrh10-hFXN-HA IC (rh10 IC), compared with Pvalb cKO mice and wild-type (WT) mice.
Figure 6C:
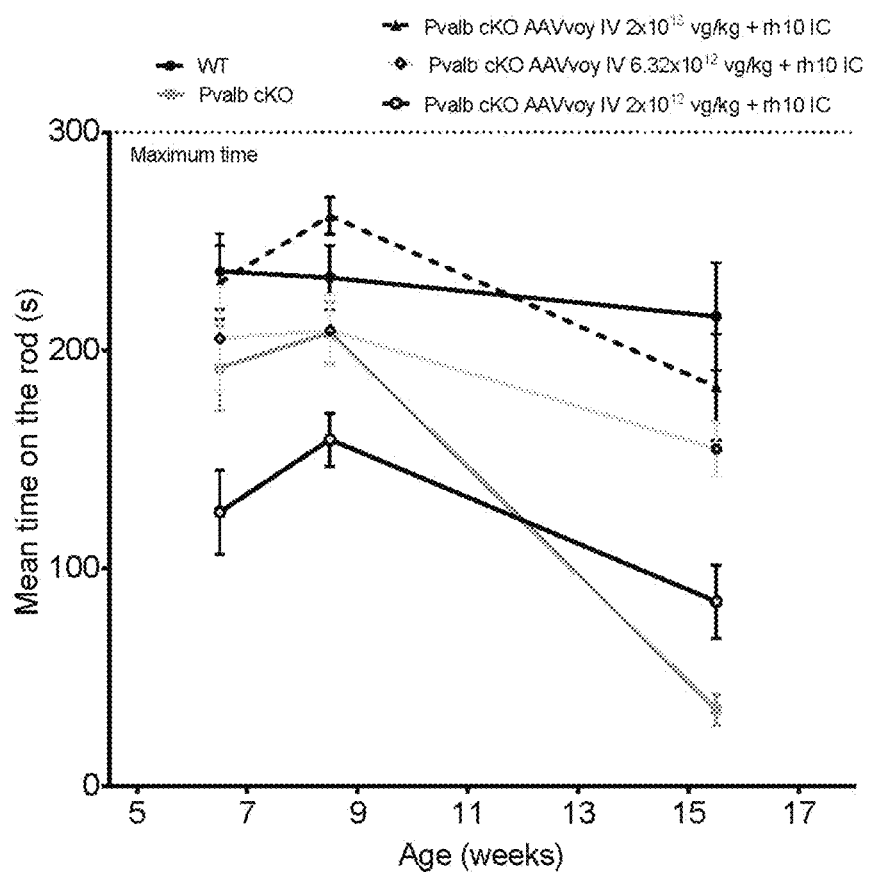
FIG. 6C shows dose-dependent behavioral rescue in the rotarod test in Pvalb cKO mice treated post-symptomatically with $2.00\times10^{12}$ VG/kg, $6.32\times10^{12}$ VG/kg, and $2.00\times10^{13}$VG/kg of AAVvoy-cFXN-HA IV (AAVvoy IV)+AAVrh10-hFXN-HA IC (rh10 IC), compared with Pvalb cKO mice and wild-type (WT) mice.

The same behavioural experimental protocols were used as in Example 3. In all tests, IV AAVvoy-cFXN-HA co-administered with IC AAVrh10-hFXN-HA rapidly reduced disease progression in a dose-dependent manner compared to Pvalb cKO mice. As shown in FIG. 6A, post-symptomatic IV AAVvoy-cFXN-HA co-administered with IC AAVrh10-hFXN-HA rescued the notched-bar test deficit. Complete protection of the ataxic phenotype from further progression was observed with AAVvoy-cFXN-HA at $2.00 \times 10^{13}$ VG/Kg IV, whereas partial protection against further progression was observed at lower doses ($2.00 \times 10^{12}$ VG/kg, $6.32 \times 10^{12}$ VG/kg) in the notched-bar test. As shown in FIG. 6B, post-symptomatic IV AAVvoy-cFXN-HA co-administered with IC AAVrh10-hFXN-HA rescued the wire hanging test deficit. Dose-dependent rescue of the phenotype was observed. Complete protection of the wire hanging test deficit was observed with AAVvoy-cFXN-HA at $2.00 \times 10^{13}$ VG/Kg IV with no difference from wild-type mice from 1 week to 11 weeks post-treatment. Complete protection against further progression was observed at the intermediate dose of $6.32 \times 10^{12}$ VG/kg, whereas partial protection against further progression was observed at the lowest tested dose of $2.00 \times 10^{12}$ VG/kg. As shown in FIG. 6C, post-symptomatic IV AAVvoy-cFXN-HA co-administered with IC AAVrh10-hFXN-HA rescued the rotarod deficit as well. Complete rescue of the locomotor phenotype was observed with AAVvoy-cFXN-HA at $2.00 \times 10^{13}$ VG/Kg IV, whereas partial dose-dependent rescue was observed at lower doses in the rotarod test. Thus, IV AAVvoy-cFXN-HA at $2.00 \times 10^{13}$ VG/Kg rapidly prevented central and peripheral disease pregression from 7.5 weeks onward.

Figure 6D:
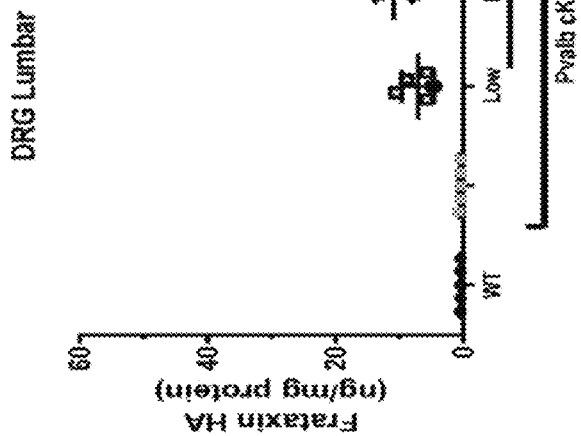
FIG. 6D shows dose-dependent expression levels of Frataxin-HA protein in cerebellum and DRGs of Pvalb cKO animals treated post-symptomatically with $2.00\times10^{12}$ VG/kg, $6.32\times10^{12}$ VG/kg, or $2.00\times10^{13}$VG/kg of AAVvoy-cFXN-HA IV (AAVvoy IV)+AAVrh10-hFXN-HA IC (rh10 IC), compared with Pvalb cKO mice and wild-type (WT) mice.
Figure 6D:
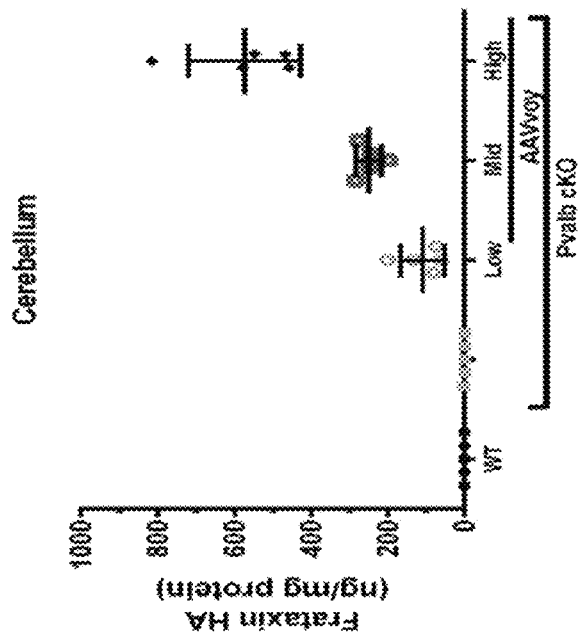

Protein levels of cFXN were measured by ELISA as described in Example 4. As shown in FIG. 6D, AAVvoy-cFXN-HA resulted in dose-dependent FXN-HA expression in cerebellum and DRGs, over the dose range tested ($2.00 \times 10^{12}$ VG/kg, $6.32 \times 10^{12}$ VG/kg, and $2.00 \times 10^{13}$ VG/kg).

Example 8. Electromyogram Analyses in Pvalb cKO Mice Following Intravenous Treatment with AAVvoy-cFXN-HA Vector A subsequent study was designed to evaluate if intravenous administration of AAVvoy-cFXN-HA solely is sufficient for behavioral benefits in post-symptomatic Pvalb FXN cKO mice. Three dose levels were evaluated for efficacy on sensory and motor function by electromyogram, notched bar walking, rotarod and string hanging assays. In all tests, AAVvoy-cFXN-HA rapidly reduced disease progression in a dose-dependent manner compared to Pvalb FXN cKO mice. We also determined whether intravenous AAVvoy-cFXN-HA could produce a sustained benefit. In contrast to Pvalb FXN cKO mice which exhibit premature death around 20 weeks of age, we demonstrated that AAV-voy-cFXN-HA provided long-lasting correction of the neurological phenotype up to 10 months after administration. Our results support use of intravenous frataxin gene therapy with novel AAV capsids that can provide long-term rescue of central and peripheral neurological phenotypes in a mouse model of Friedreich's Ataxia.

To test the dose-dependence of rescue of sensory physiology deficit in Pvalb cKO mice treated with post-symptomatic IV AAVvoy-cFXN-HA, the AAVvoy-cFXN-HA particles were administered to adult (7.5 weeks of age) Pvalb cKO mice as described in Example 2. The IV doses of AAVvoy-cFXN-HA tested were $2.00 \times 10^{12}$ VG/kg, $6.32 \times 10^{12}$ VG/kg, and $2.00 \times 10^{13}$ VG/kg.

Electromyogram analyses were performed using the Natus UltraProS100 apparatus (Mag2Health, France). Pvalb cKO mice were anesthetized using IP injection with ketamine/xylazine (130/13 mg/kg). Animals were maintained at 37° C. throughout the electrophysiological assessment. Amplitudes of H waves were recorded in the plantar hind paw muscle after sciatic nerve stimulation (0.1 ms and 8 mA intensity). Measurements were performed at 6.5, 8.5 and 15.5 weeks of age.

Figure 7:
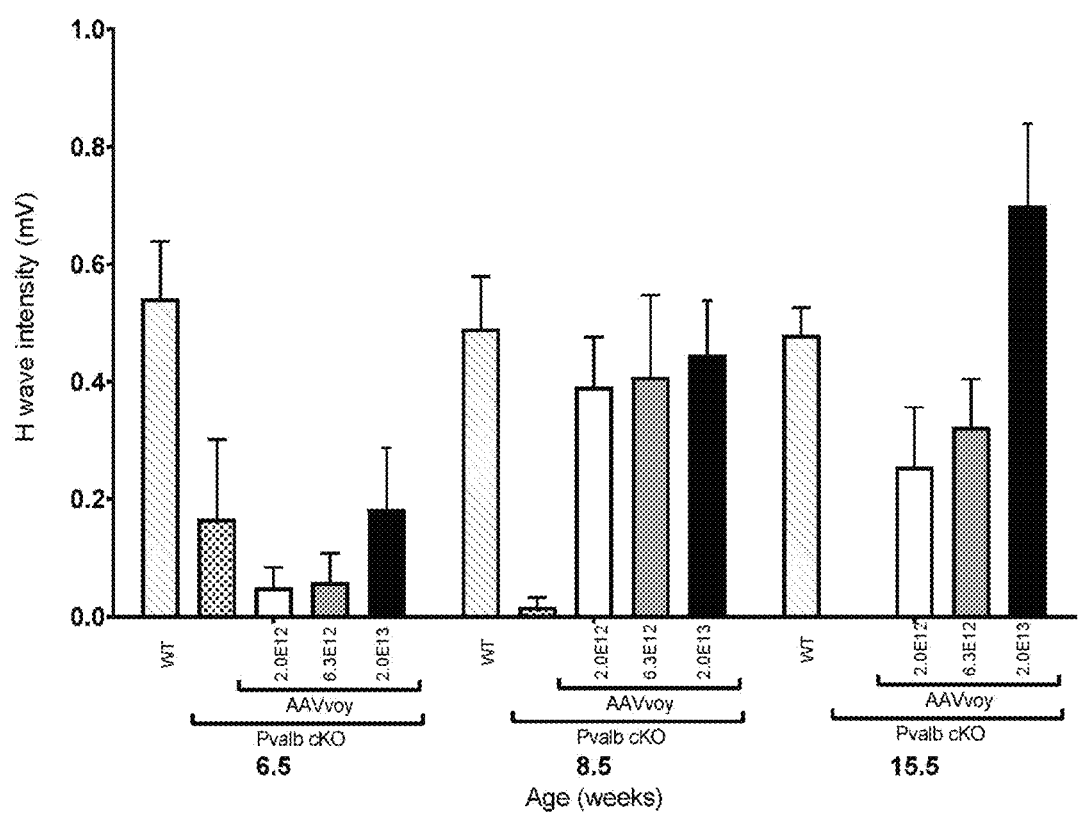
FIG. 7 shows electromyographic measurements in Pvalb cKO animals treated post-symptomatically with intravenous AAVvoy-cFXN-HA (AAVvoy) at $2.00\times10^{12}$ VG/kg, $6.32\times10^{12}$ VG/kg, or $2.00\times10^{13}$ VG/kg, compared with Pvalb cKO mice and wild-type (WT) mice.

As shown in FIG. 7, electromyographic measurements in Pvalb cKO animals treated with AAVvoy-cFXN-HA IV (all 3 doses) show restoration of the spinal somatosensory evoked response (H wave) at 1 week and 8 weeks following treatment at 7.5 weeks of age, indicating functional recovery of large myelinated proprioceptive sensory neurons at all doses tested. H wave amplitudes decreased in Pvalb cKO mice from 6.5 to 8.5 weeks of age and were no longer measurable at 15.5 weeks of age. In contrast, in Pvalb cKO mice that received IV AAVvoy-cFXN-HA, H wave amplitudes were nearly completely restored to wild-type amplitudes by 1 week post-treatment, for all 3 doses ($2.00 \times 10^{12}$ VG/kg, $6.32 \times 10^{12}$ VG/kg, and $2.00 \times 10^{13}$ VG/kg). By 15.5 weeks of age (8 weeks post-treatment), H wave amplitudes in Pvalb cKO mice were largely restored compared with wild-type amplitudes for low ($2.00 \times 10^{12}$ VG/kg) and mid ($6.32 \times 10^{12}$ VG/kg) dose levels of IV AAVvoy-cFXN-HA. However, at this timepoint (8 weeks post-treatment), there was significantly more restoration of H wave amplitude in Pvalb cKO mice that received high dose ($2.00 \times 10^{13}$ VG/kg) IV AAVvoy-cFXN-HA, compared with those that received lower doses of IV AAVvoy-cFXN-HA.

These results desmonstrate a dose dependent effect of IV AAVvoy-cFXN-HA on spinal somatosensory evoked response, especially with an increase in IV dose from $6.32 \times 10^{12}$ VG/kg to $2.00 \times 10^{13}$ VG/kg.

Example 9. Behavioral Analysis in Pvalb cKO Mice Following Intravenous Treatment with AAVvoy-cFXN-HA Vector To test the rescue of motor and muscular function in Pvalb cKO animals treated with post-symptomatic IV AAVvoy-cFXN-HA, the AAVvoy-cFXN-HA particles were administered to adult (7.5 weeks of age) Pvalb cKO mice as described in Example 2. The IV doses of AAVvoy-cFXN-HA tested were $2.00 \times 10^{12}$ VG/kg, $6.32 \times 10^{12}$ VG/kg, and $2.00 \times 10^{13}$ VG/kg.

Behavioral experiments were conducted to evaluate motor and muscular function. Coordination was evaluated using the notched-bar test (scored number of slips of the upper or lower limbs; 'falls') and the wire hanging test (measured time needed by animal to attach their hindlimbs when suspended by forelimbs) as previously described (Piguet el al. (2018) Rapid and complete reversal of sensory ataxia by gene therapy in a novel model of Friedreich ataxia Molecular Therapy; Arbogast et al. (2015). Deletion of the App-Runx1 region in mice models human partial monosomy 21. Dis. Model. Mech. 8: 623-634.) but without training. General motor capacities were tested using the accelerating rotarod LE8200 (Bioseb, France) as previously described (mousephenotype.org/). Animals were scored weekly in the following order: wire-hanging test, notched-bar test, and rotarod.

Figure 8A:
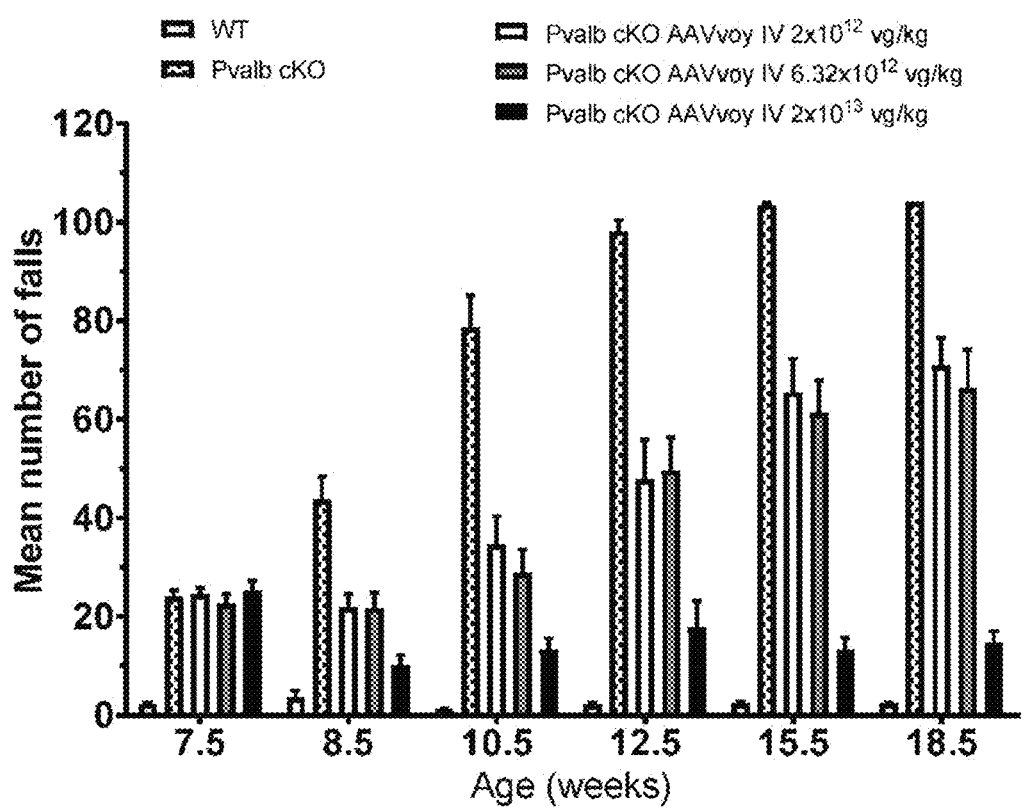
FIG. 8A shows dose-dependent behavioral rescue in the notched-bar test in Pvalb cKO mice treated post-symptomatically with intravenous AAVvoy-cFXN-HA (AAVvoy IV) at $2.00\times10^{12}$ VG/kg, $6.32\times10^{12}$ VG/kg, or $2.00\times10^{13}$ VG/kg, compared with Pvalb cKO mice and wild-type (WT) mice.
Figure 8B:
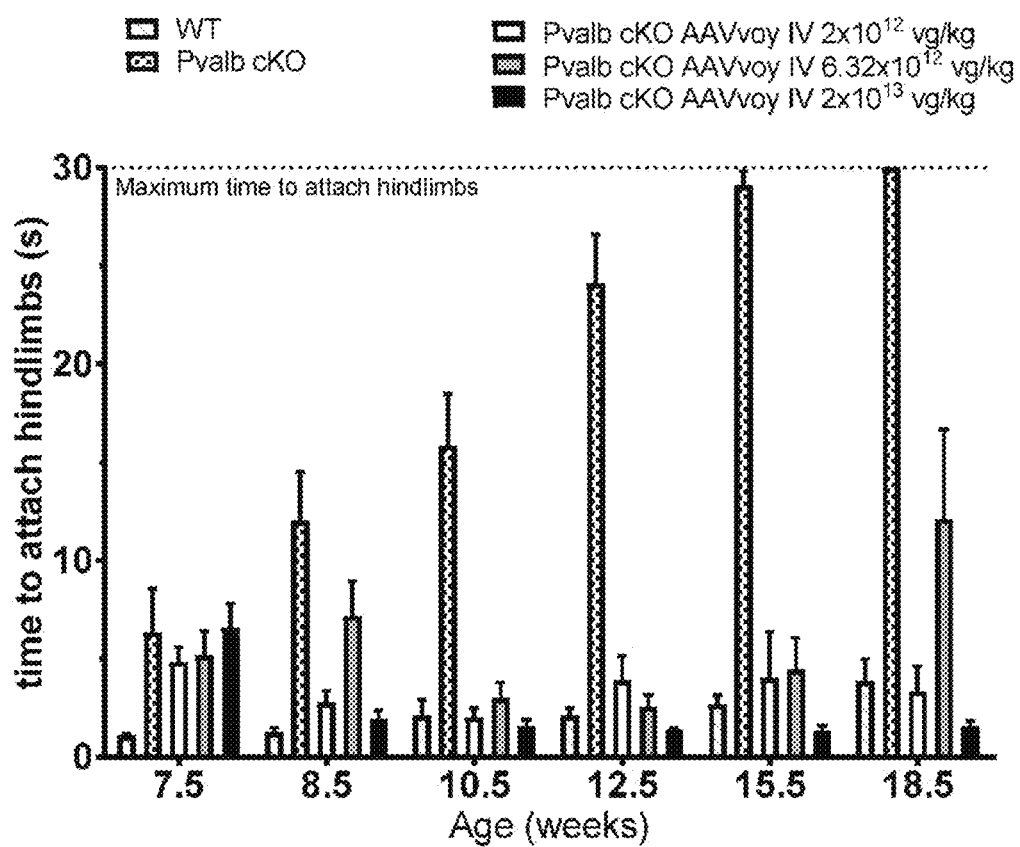
FIG. 8B shows dose-dependent behavioral rescue in the wire hanging test in Pvalb cKO mice treated post-symptomatically with intravenous AAVvoy-cFXN-HA (AAVvoy IV) at $2.00\times10^{12}$ VG/kg, $6.32\times10^{12}$ VG/kg, or $2.00\times10^{13}$ VG/kg, compared with Pvalb cKO mice and wild-type (WT) mice.
Figure 8C:
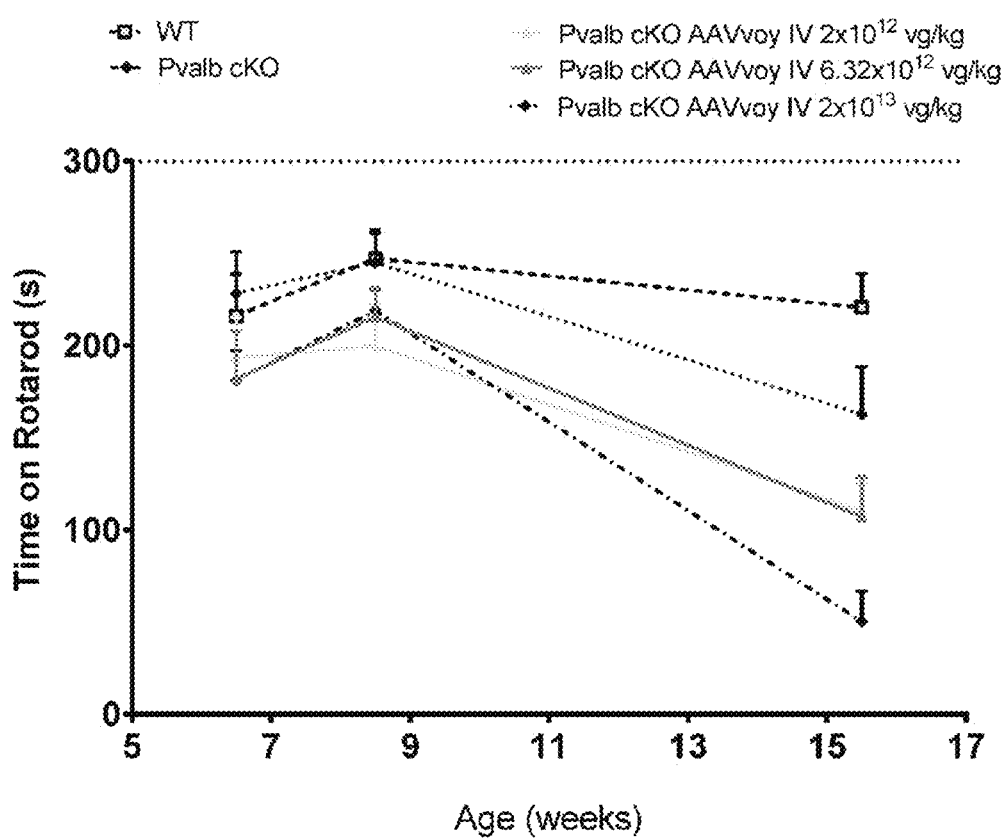
FIG. 8C shows dose-dependent behavioral rescue by the rotarod test in Pvalb cKO mice treated post-symptomatically with intravenous AAVvoy-cFXN-HA (AAVvoy IV) at $2.00\times10^{12}$ VG/kg, $6.32\times10^{12}$ VG/kg, or $2.00\times10^{13}$ VG/kg, compared with Pvalb cKO mice and wild-type (WT) mice.

In all tests, AAVvoy-cFXN-HA rapidly reduced disease progression in a dose-dependent manner compared to Pvalb cKO mice. As shown in FIG. 8A, post-symptomatic IV AAVvoy-cFXN-HA rescued the notched-bar test deficit. Complete protection against progression and partial reversal of the ataxic phenotype was observed with AAVvoy-cFXN-HA at $2.00 \times 10^{13}$ VG/Kg IV, whereas partial protection against progression was observed at lower doses ($6.32 \times 10^{12}$ VG/kg, and $2.00 \times 10^{12}$ VG/kg) in the notched-bar test. As shown in FIG. 8B, post-symptomatic intravenous AAVvoy-cFXN-HA rescued the wire hanging test deficit. Complete rescue including complete reversal of the ataxic phenotype was observed with AAVvoy-cFXN-HA at $2.00 \times 10^{13}$ VG/Kg IV as early as 8.5 weeks of age (1 week post-treatment), whereas intermediate and partial rescue were observed at lower doses ($6.32 \times 10^{12}$ VG/kg, and $2.00 \times 10^{12}$ VG/kg) in the wire hanging test. As shown in FIG. 8C, post-symptomatic intravenous AAVvoy-cFXN-HA rescued the rotarod deficit as well. Nearly complete rescue of the locomotor phenotype was observed at 15.5 weeks of age (8 weeks post-treatment) with AAVvoy-cFXN-HA at $2.00 \times 10^{13}$ VG/Kg IV, whereas partial rescue was observed at lower doses ($6.32 \times 10^{12}$ VG/kg, and $2.00 \times 10^{12}$ VG/kg) in the rotarod test.

Example 10. Histological Analysis of DRG and Cerebellum in Pvalb cKO Mice Following Intravenous Treatment with AAVvoy-cFXN-HA Vector For histological analyses, mice were euthanized by IP injection of ketamine-xylazine (300/13 mg/kg) and perfused with 10 mL of Phosphate Buffer Saline (PBS) 11 weeks after treatment. Various tissues were dissected, and either fixed in PFA and embedded in paraffin, or directly embedded in Shandon Cryomatrix embedding resin (ThermoFisher Scientific) and snap-frozen in isopentane chilled on dry ice. For DRG analysis, prior to the paraffin embedding, the column was decalcified in ethylene-diamine-tetra acetic 0.34M, pH 7.4 (EDTA) for 14 days.

HA immunodetection was performed on paraffin sections using Vectastain ABC kit followed DAB enhancement according to manufacturer protocol (Vector Labs), with slight modification including epitope unmasking in 10 mM Tris, 1 mM EDTA, 0.1% tween20 at pH 8.75 for 45 min at 95° C., and images acquired on a Hamamatsu NanoZoomer 2.0 slide scanner. All experiments were performed blindly.

Figure 9:
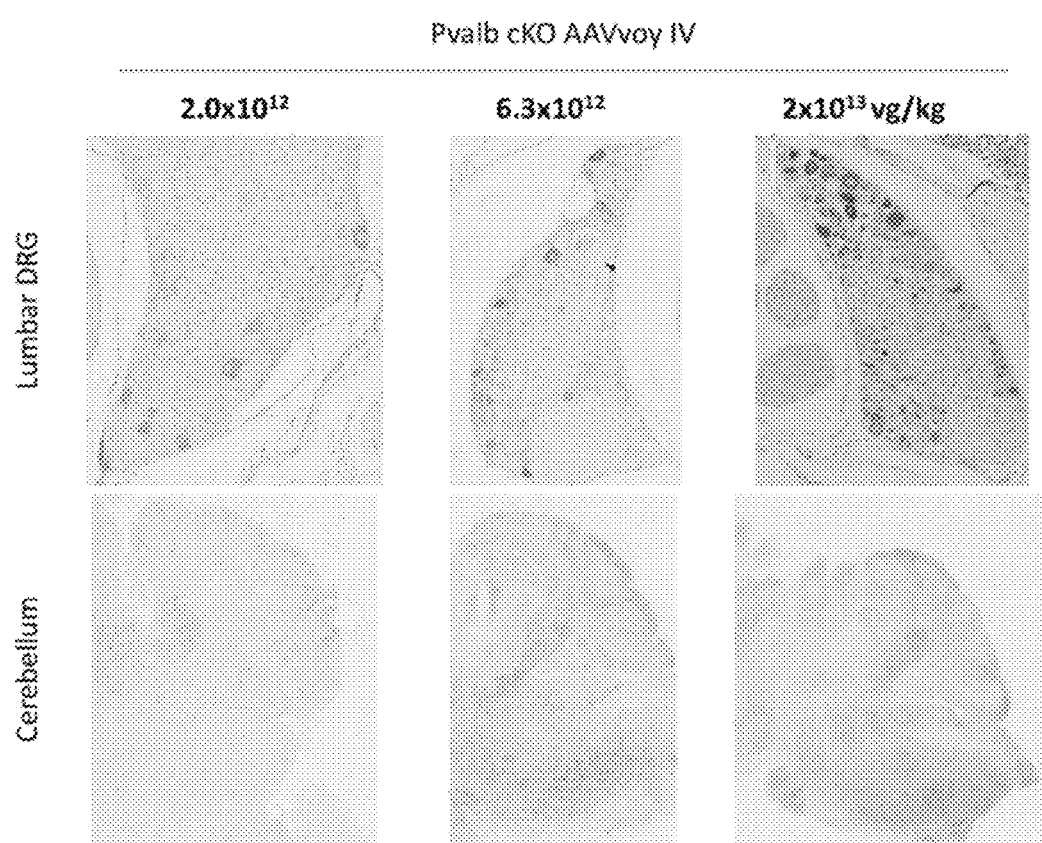
FIG. 9 shows immunohistological analysis of transgene (HA) expression in lumbar DRG and cerebellum of Pvalb cKO animals treated post-symptomatically with intravenous AAVvoy-cFXN-HA (AAVvoy IV) at $2.00\times10^{12}$ VG/kg, $6.32\times10^{12}$ VG/kg, or $2.00\times10^{13}$ VG/kg.

As shown in FIG. 9, IV treatment with AAVvoy-cFXN-HA resulted in dose-dependent transgene expression in lumbar DRG neurons and cerebellar neurons.

Example 11. Long-Lasting Correction of Proprioceptive, Ataxic and Neurological Phenotype in Pvalb cKO Mice Following Intravenous Treatment with AAVvoy-cFXN-HA Vector To evaluate the long-term correction of proprioceptive and behavioral deficits by treatment with IV AAVvoy-cFXN-HA, the same electromyogram analysis and behavioural experiment protocols were used as in Examples 8 and 9, respectively, except that measurements were taken following administration of AAVvoy-cFXN-HA at the single IV dose of $2.00 \times 10^{13}$ VG/kg to Pvalb cKO mice 7.5 weeks of age, until the animals reached 50.5 weeks of age. Performance were compared to untreated Pvalb cKO mice, which were euthanized at 18.5 weeks of age and to wild-type mice until 52 weeks of age.

As shown in FIG. 10A, electromyographic measurements in Pvalb cKO treated animals show complete restoration of the spinal somatosensory evoked response (H wave) more than 10 months after dosing, indicating long term functional recovery of large myelinated proprioceptive sensory neurons.

Figure 10B:
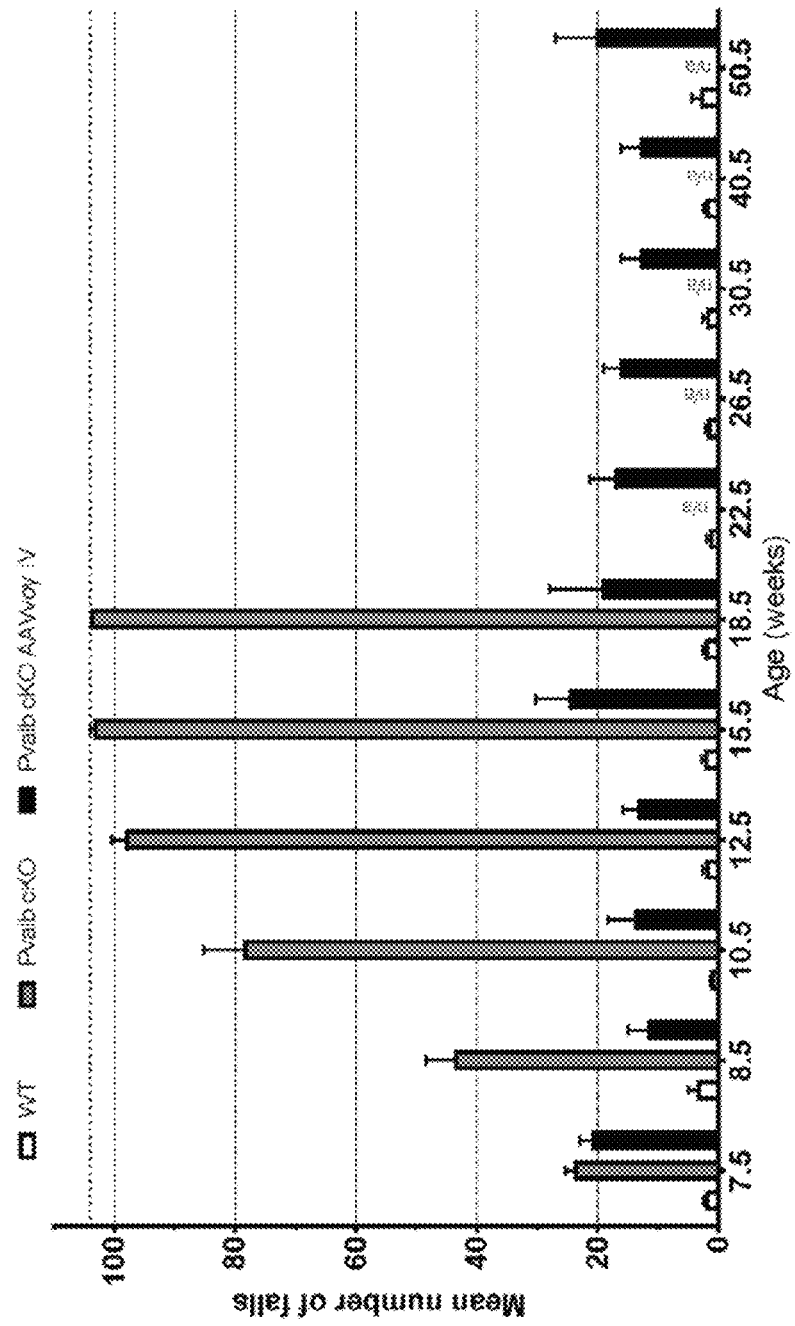
FIG. 10B shows long-term behavioral rescue in the notched-bar test in Pvalb cKO mice treated post-symptomatically with intravenous AAVvoy-cFXN-HA (AAVvoy IV) at $2.00\times10^{13}$ VG/kg, compared with Pvalb cKO mice and wild-type (WT) mice until the animals reached 50.5 weeks of age.
Figure 10C:
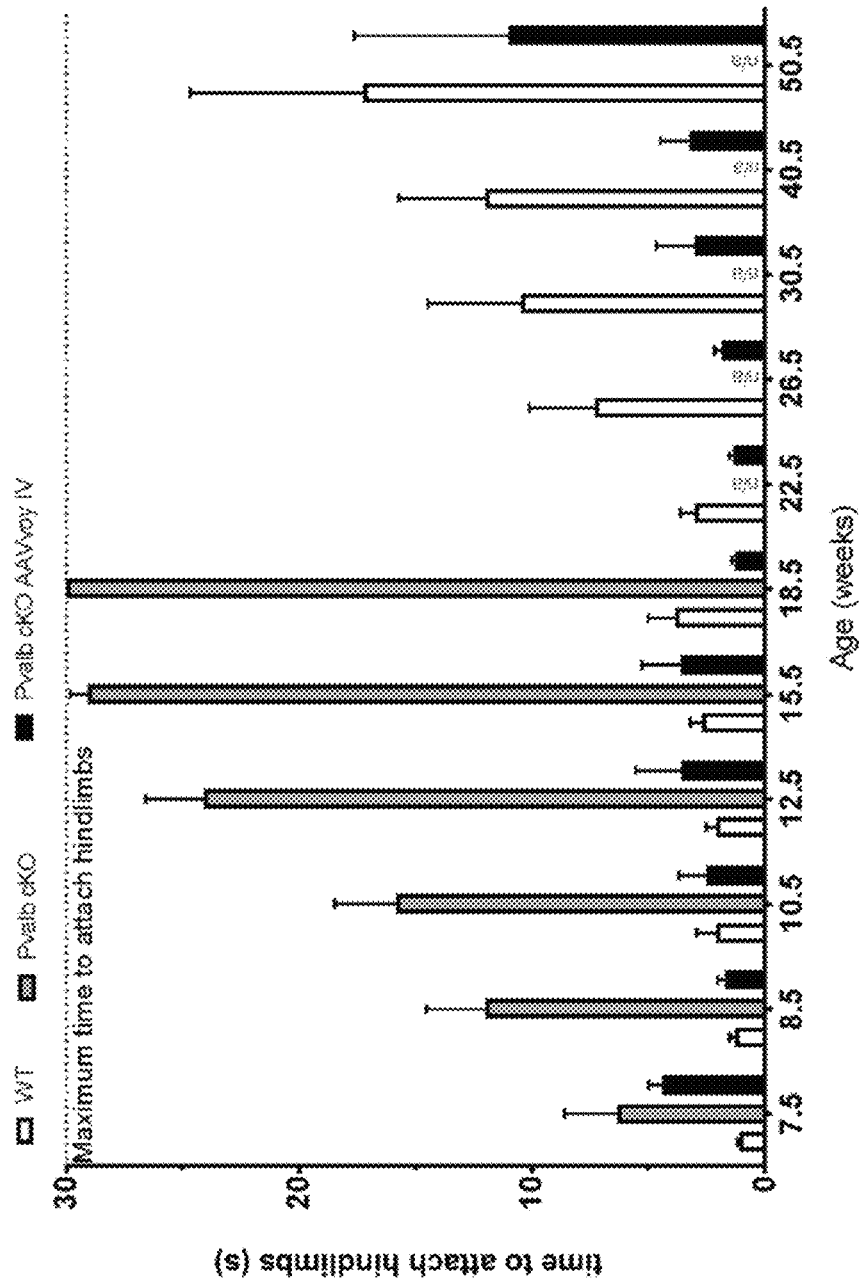
FIG. 10C shows long-term behavioral rescue in the wire hanging test in Pvalb cKO mice treated post-symptomatically with intravenous AAVvoy-cFXN-HA (AAVvoy IV) at $2.00\times10^{13}$ VG/kg, compared with Pvalb cKO mice and wild-type (WT) mice until the animals reached 50.5 weeks of age.
Figure 10D:
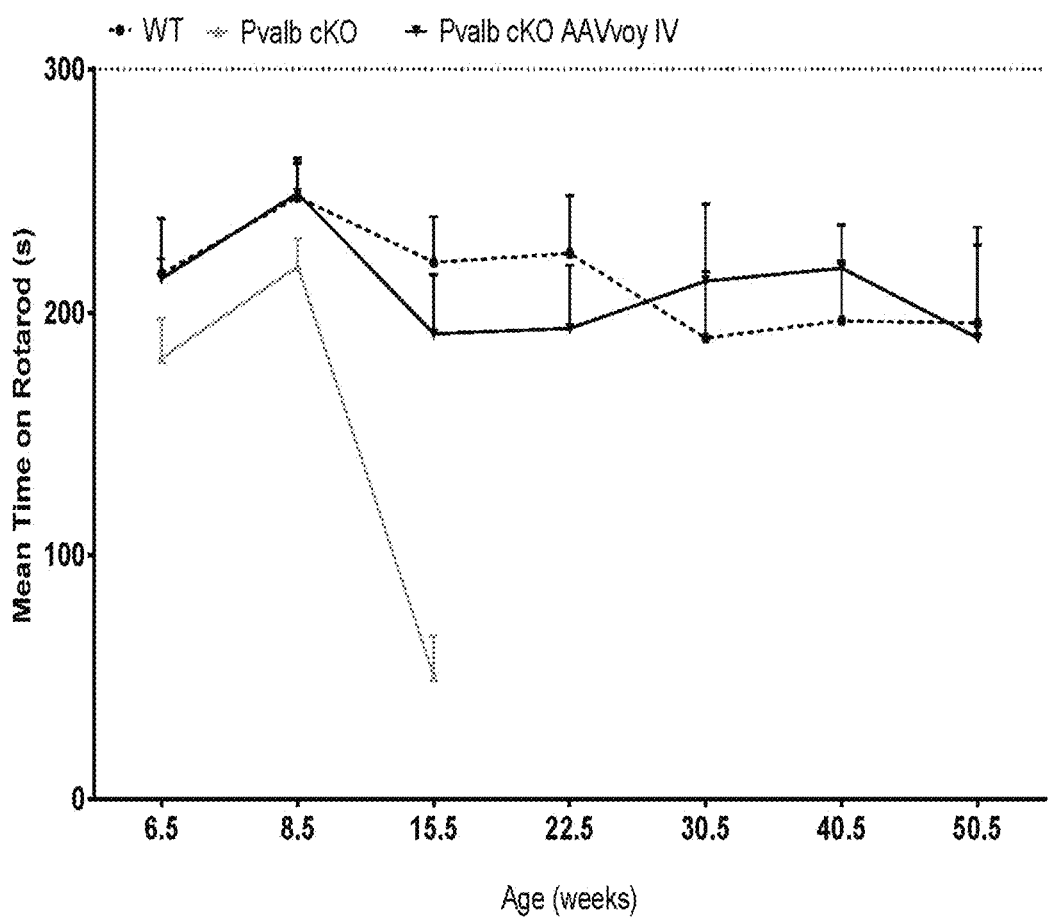
FIG. 10D shows long-term behavioral rescue in the rotarod test in Pvalb cKO mice treated post-symptomatically with intravenous AAVvoy-cFXN-HA (AAVvoy IV) at $2.00\times10^{13}$ VG/kg, compared with Pvalb cKO mice and wild-type (WT) mice until the animals reached 50.5 weeks of age.

FIG. 10B shows that the progression of the notched-bar walking ataxic phenotype was halted in Pvalb cKO treated animals for more than 10 months following IV administration of AAVvoy-FXN-HA at $2.00 \times 10^{13}$ VG/Kg, whereas untreated Pvalb cKO conditional mutants became progressively more ataxic from 7.5 to 18.5 weeks of age. Typically, untreated Pvalb cKO conditional mutants die around 20 weeks of age (euthanized at 18.5 weeks of age in current study). As shown in FIG. 10C, the deficit in the wire hanging test was delayed by AAVvoy-cFXN-HA for approximately 8 months after treatment. Performance of wild-type mice worsens with age after 22.5 weeks of age, whereas AAVvoy-cFXN-HA treated animals maintained good performance until 50.5 weeks of age. FIG. 10D shows that Pvalb cKO mice treated by IV administration with AAVvoy-cFXN-HA at $2.00 \times 10^{13}$ VG/Kg maintained performance comparable to wild-type mice in the rotarod test through 50.5 weeks of age, 43 weeks post-treatment, in contrast to Pvalb cKO mice which exhibit a dramatic decline in rotarod performance by 15.5 weeks of age.

In conclusion, these results demonstrate that in contrast to Pvalb cKO mice which exhibit premature death around 20 weeks of age and profound proprioceptive and behavioral deficits, an IV administration of AAVvoy-cFXN-HA at $2.00 \times 10^{13}$ VG/Kg provides long-lasting correction of the proprioceptive, ataxic and neurological phenotype, and survival until at least 50.5 weeks of age, more than 10 months after post-symptomatic administration of AAVvoy-cFXN-HA.

VII. EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCE LISTING

```
Sequence total quantity: 12
SEQ ID NO: 1            moltype = DNA   length = 2772
FEATURE                 Location/Qualifiers
misc_feature            1..2772
                        note = Description of Artificial Sequence: Synthetic
                        Polynucleotide
source                  1..2772
                        mol_type = other DNA
                        organism = synthetic construct
SEQUENCE: 1
cctgcaggca gctgcgcgct cgctcgctca ctgaggccgc ccgggcaaag cccggcgtc    60
gggcgacctt tggtcgcccg gcctcagtga gcgagcgagc gcgcagagag ggagtggcca   120
actccatcac taggggttcc ttgtagttaa tgattaaccc gccatgctac ttatctacgt   180
agccatgcgt cgacataacg cgtcgttaca taacttacgg taaatggccc gcctggctga   240
ccgcccaacg acccccgccc attgacgtca ataatgacgt atgttcccat agtaacgcca   300
ataggggactt tccattgacg tcaatgggtg gagtatttac ggtaaactgc ccacttggca   360
gtacatcaag tgtatcatat gccaagtacg ccccctattg acgtcaatga cggtaaatgg   420
cccgcctggc attatgccca gtacatgacc ttatgggact ttcctacttg gcagtacatc   480
tacgtattag tcatcgctat taccatggtg atgcggtttt ggcagtacat caatgggcgt   540
ggatagcggt ttgactcacg gggatttcca agtctccacc ccattgacgt caatgggagt   600
ttgttttggc accaaaatca acgggacttt ccaaaatgtc gtaacaactc cgccccattg   660
acgcaaatgg gcggtaggcg tgtacggtgg gaggtctata taagcagagc tcgggagcaa   720
gcttcgttta gtgaaccgtc agatcgcctg gagacgccat ccacgctgtt ttgacctcca   780
tagaagacac cgggaccgat ccagcctccg cggattcgaa tcccggccgg gaacggtgca   840
ttggaacgcg gattccccgt gccaagagtg acgtaagtac cgcctataga gtctataggc   900
ccacaaaaaa tgctttcttc ttttaatata ctttttttgt tatcttattt ctaatacttt   960
ccctaatctc tttctttcag ggcaataatg atacaatgta tcatgcctct ttgcaccatt  1020
ctaaagaata acagtgataa tttctgggtt aaggcaatag caatatttct gcatataaat  1080
atttctgcat ataaattgta actgatgtaa gaggtttcat attgctaata gcagctacaa  1140
tccagctacc attctgcttt tattttatgg ttgggataag gctggattat tctgagtcca  1200
agctaggccc ttttgctaat catgttcata cctcttatct tcctcccaca gctcctgggc  1260
aacgtgctgg tctgtgtgct ggcccatcac ttttggcaaag aatttgggatt cgaaccggta  1320
tgtggacttt cgggcgccgc gcagttgccg gcctcctggc gtccccgagc ccggcccagg  1380
cccagaccct cacccgggcc ccgcggctgg cagagttggc ccagctctgc agccgccggg  1440
gcctgcgcac cggcatcaat gcgacctgca caacccacca caccagttcg aacctccgtg  1500
gcctcaacca gattcggaat gtcaaaaggc agagtgtcta cttgatgaat ttgaggaaat  1560
cgggaacttt gggccaccca ggctctctag atgacaccac ctatgaaaga ctagcagagg  1620
aaacgctgga ctctttagca gagttttttg aagaccttgc agacaagcca tacacctttg  1680
aggactaga tgtttccttt gggagtggtg tcttaactgt taaactgggt ggagatctga  1740
gaacctacgt gatcaacaag cagacgccaa acaagcaaat ctggttatct tctccatcca  1800
gtggaccaa gcgttatgac tggactggga aaaactgggt gtattccac gacggcgttt  1860
ccctccatga gctgctgggc gcagagctca ctaaagcctt aaaaaccaaa ctggacttgt  1920
cttccttggc ctattccgga aaagacgctt atccttatga cgtgcctgac tatgcctgat  1980
gactcgagcc attgactagt acaaacacca ttgtcacact ccacacaaac accattgtca  2040
cactccacac aaacaccatt gtcacactcc actgcagtca ggtctatcct gaggatgggt  2100
ggcatccctg tgacccctcc ccagtgcctc tcctggccct ggaagttgcc actccagtgc  2160
ccaccagcct tgtcctaata aaattaagtt gcatcattt gtctgactag gtgtccttct  2220
ataatattat ggggtggagg gggtggtat ggagcaaggg gcaagttggg aagacaacct  2280
gtagggcctg cggggtctat tgggaaccaa gctgagtgc agtggcacaa tcttggctca  2340
ctgcaatctc cgcctcctgg gttcaagcga ttctcctgcc tcagcctccc gagttgttgg  2400
gattccaggc atgcatgacc aggctcagct aattttttgtt ttttggtag agacggggtt  2460
tcaccatatt ggccaggctg gtctccaact cctaatctca ggtgatctac ccaccttggc  2520
ctcccaaatt gctgggatta caggcgtgaa ccactgctcc cttccctgtc cttggcctag  2580
```

```
gtatcgatgc tacgtagata agtagcatgg cgggttaatc attaactaca gaggaacccc  2640
tagtgatgga gttggccact ccctctctgc gcgctcgctc gctcactgag gccgggcgac  2700
caaaggtcgc ccgacgcccg ggctttgccc gggcggcctc agtgagcgag cgagcgcgca  2760
gctgcctgca gg                                                      2772

SEQ ID NO: 2           moltype = AA   length = 743
FEATURE                Location/Qualifiers
REGION                 1..743
                       note = Description of Artificial Sequence: Synthetic
                       Polypeptide
source                 1..743
                       mol_type = protein
                       organism = synthetic construct
SEQUENCE: 2
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                          743

SEQ ID NO: 3           moltype = DNA   length = 2232
FEATURE                Location/Qualifiers
misc_feature           1..2232
                       note = Description of Artificial Sequence: Synthetic
                       Polynucleotide
source                 1..2232
                       mol_type = other DNA
                       organism = synthetic construct
SEQUENCE: 3
atggctgccg atggttatct tccagattgg ctcgaggaca accttagtga aggaattcgc   60
gagtggtggg cttgaaacc tggagcccct caacccaagg caaatcaaca acatcaagac  120
aacgctcgag gtcttgtgct tccgggttac aaataccttg acccggcaa cggactcgac  180
aaggggagc cggtcaacgc agcagacgcg gcggccctcg agcacgacaa ggcctacgac  240
cagcagctca aggccggaga caacccgtac ctcaagtaca ccacgccga cgccgagttc  300
caggagcgc tcaaagaaga tacgtctttt ggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctcgc gggtattggc  480
aaatcggtg cacagcccgc taaaagaga ctcaatttcg gtcagactgg cgacacagag  540
tcagtcccag acccctcaacc aatcggagaa cctcccgcag ccccctcagg tgtgggatct  600
cttacaatgg cttcaggtgg tggcgcacca gtgcagaca ataacgaagg tgccgatgga  660
gtgggtagtt cctcgggaaa ttggcattgc gattccaat ggctggggga cagagtcatc  720
accaccagca cccgaacctg ggccctgcc cctacaaca tcacctcta caagcaaatc  780
tccaacagca catctggagg atcttcaaat gacaacgcct acttcggcta cagcacccc  840
tgggggtatt ttgacttcaa cagattccac tgccacttct caccacgtga ctggcagcga  900
ctcatcaaca caactggggg attccggcct aagcgactca acttcaagct cttcaacatt  960
caggtcaaag aggttacgga caacaatgga gtcaagacca tcgccaataa ccttaccagc 1020
acggtcaagg tcttcacgga ctcagactat cagctccgtg acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctgacc gactaatgaa tccactcatc 1320
gaccaatact tgtactatct ctccaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaacaa caacagcgaa 1500
tttgcttggc ctggagcttc ttcttgggct ctcaatggac gtaatagctt gatgaatcct 1560
ggacctgcta tggccagcca caagaagga ggagacgtt tctttcctt gtctggatct 1620
ttaatttttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc ccaaactttg cggtgccttt taaggcaca ggcgcagacc 1800
ggctgggtc aaaaccaagg aatcttccg ggtatggttt ggcaggacag agatgtgtac 1860
ctgcaaggac ccatttgggc caaattcct cacacgacg gcaacttcca ccctctccag 1920
ctgatgggag ggtttggaat gaagcacccg cctcctcaga tcctcatcaa aaacacacct 1980
gtacctgcgg atcctccaac ggccttcaac aaggacaagc tgaactcttt catcacccag 2040
tattctactg gccaagtcag cgtggagatc gagtgggagc tgcagaagga aaacagcaag 2100
cgctggaacc cggagatcca gtacacttcc aactattaca gtctaataa tgttgaattt 2160
gctgttaata ctgaaggtgt atatagtgaa ccccgcccca ttggcaccag atacctgact 2220
cgtaatctgt aa                                                    2232

SEQ ID NO: 4           moltype = AA   length = 210
FEATURE                Location/Qualifiers
source                 1..210
```

```
                              mol_type = protein
                              organism = Homo sapiens
SEQUENCE: 4
MWTLGRRAVA GLLASPSPAQ AQTLTRVPRP AELAPLCGRR GLRTDIDATC TPRRASSNQR    60
GLNQIWNVKK QSVYLMNLRK SGTLGHPGSL DETTYERLAE ETLDSLAEFF EDLADKPYTF   120
EDYDVSFGSG VLTVKLGGDL GTYVINKQTP NKQIWLSSPS SGPKRYDWTG KNWVYSHDGV   180
SLHELLAAEL TKALKTKLDL SSLAYSGKDA                                   210

SEQ ID NO: 5              moltype = AA    length = 196
FEATURE                   Location/Qualifiers
source                    1..196
                          mol_type = protein
                          organism = Homo sapiens
SEQUENCE: 5
MWTLGRRAVA GLLASPSPAQ AQTLTRVPRP AELAPLCGRR GLRTDIDATC TPRRASSNQR    60
GLNQIWNVKK QSVYLMNLRK SGTLGHPGSL DETTYERLAE ETLDSLAEFF EDLADKPYTF   120
EDYDVSFGSG VLTVKLGGDL GTYVINKQTP NKQIWLSSPS RYVVDLSVMT GLGKTGCTPT   180
TACPSMSCWP QSSLKP                                                  196

SEQ ID NO: 6              moltype = AA    length = 171
FEATURE                   Location/Qualifiers
source                    1..171
                          mol_type = protein
                          organism = Homo sapiens
SEQUENCE: 6
MWTLGRRAVA GLLASPSPAQ AQTLTRVPRP AELAPLCGRR GLRTDIDATC TPRRASSNQR    60
GLNQIWNVKK QSVYLMNLRK SGTLGHPGSL DETTYERLAE ETLDSLAEFF EDLADKPYTF   120
EDYDVSFGSG VLTVKLGGDL GTYVINKQTP NKQIWLSSPS RLTWLLWLFH P            171

SEQ ID NO: 7              moltype = DNA   length = 7168
FEATURE                   Location/Qualifiers
source                    1..7168
                          mol_type = other DNA
                          organism = Homo sapiens
SEQUENCE: 7
agtctccctt gggtcagggg tcctggttgc actccgtgct ttgcacaaag caggctctcc    60
attttgtta aatgcacgaa tagtgctaag ctgggaagtt cttcctgagg tctaacctct   120
agctgctccc ccacagaaga gtgcctgcgg ccagtggcca ccaggggtcg ccgcagcacc   180
cagcgctgga gggcggagcg ggcggcagac ccggagcagc atgtggactc tcgggcgccg   240
cgcagtagcc ggcctcctgg cgtcacccag cccagcccag ccccagaccc tcacccgggt   300
cccgcggccg gcagagttgg ccccactctg cggccgccgt ggcctgcgca ccgacatcga   360
tgcgacctgc acgccccgcc gcgcaagttc gaaccaacgt ggcctcaacc agatttggaa   420
tgtcaaaaag cagagtgtct atttgatgaa tttgaggaaa tctggaactt tgggccaccc   480
aggctctcta gatgagacca cctatgaaag actagcagag gaaacgctgg actctttagc   540
agagttttt gaagaccttg cagacaagcc atacacgttt gaggactatg atgtctcctt   600
tgggagtggt gtcttaactg tcaaactggg tggagatcta ggaacctatg tgatcaacaa   660
gcagccgcca aacaagcaaa tctggctatc ttctccatcc agtggaccta agcgttatga   720
ctggactggg aaaaactggg tgtactccca cgacggcgtg tccctccatg agctgctggc   780
cgcagagctc actaaagcct taaaaaccaa actggacttg tcttcttggg cctattccgg   840
aaaagatgct tgatgcccag ccccgtttta aggacattaa aagctatcag gccaagaccc   900
cagcttcatt atgcagctga ggtctgtttt tgttgttgtt tgttgtttat tttttttatt   960
cctgcttttg aggacagttg ggctatgtgt cacagctctg tagaaagaat gtgttgcctc  1020
ctaccttgcc cccaagttct gatttttaat ttctatggaa gatttttggg attgtcggat  1080
ttcctccctc acatgatacc ccttatcttt tataatgtct tatgcctata cctgaatata  1140
acaacctta aaaaagcaaa ataataagaa ggaaaaattc caggagggaa aatgaattgt  1200
cttcactctt cattctttga aggatttact gcaagaagta catgaagagc agctggtcaa  1260
cctgctcact gttctatctc caaatgagac acattaaagg gtagcctaca aatgttttca  1320
ggcttctttc aaagtgtaag cacttctgag ctctttagca ttgaagtgtc gaaagcaact  1380
cacacgggaa gatcatttct tatttgtgct ctgtgactgc caaggtgtgg cctgcactgg  1440
gttgtccagg gagacctagt gctgtttctc ccacatattc acatacgtgt ctgtgtgtat  1500
atatattttt tcaatttaaa ggttagtatg gaatcagctg ctacaagaat gcaaaaaatc  1560
ttccaaagac aagaaaagag gaaaaaaagc cgttttcatg agctgagtga tgtagcgtaa  1620
caaacaaat catggagctg aggaggtgcc ttgtaaacat gaaggggcag ataaaggaag  1680
gagatactca tgttgataaa gagagccctg gtcctagca tagttcagcc acaaagtagt  1740
tgtcccttg tggacaagtt tcccaaattc cctggacctc tgcttcccca tctgttaaat  1800
gagagaaatag agtatggttg attcccagca ttcagtggtc ctgtcaagca acctaacagg  1860
ctagttctaa ttccctattg ggtagatgag gggatgacaa agaacagttt ttaagctata  1920
taggaaacat tgttattggt gttgccctat cgtgatttca gttgaattca tgtgaaaata  1980
atagccatcc ttggcctggc gcggtggctc acacctgtaa tcccagcact tttggaggcc  2040
aaggtgggtg gatcacctga ggtcaggagt tcaagaccag cctggccaac atgatgaaac  2100
cccgtctcta ctaaaaatac aaaaaattag ccgggcatga tggcaggtgc ctgtaatccc  2160
agctacttgg gaggctgaag cggaagaatc gcttgaaccc agaggtggag gttgcagtga  2220
gccgagatcg tgccattgca ctgtaacctg ggtgactgag caaactctg tctcaaaata  2280
ataataacaa tataataata ataatagcca tcctttattg taccccttact gggttaatcg  2340
tattatacca cattacctca tttttaatttt tactgacctg cacttttatac aaagcaacaa  2400
gcctccagga cattaaaatt catgcaaagt tatgctcatg ttatattatt ttcttactta  2460
aagaaggatt tattagtggc tgggcatggt ggcgtgcacc tgtaatccca ggtactcagg  2520
aggctgagac gggagaattg cttgacccca ggcggaggag gttacagtga gtcgagatcg  2580
tacctgagcg acagagcgag actccgtctc aaaaaaaaaa aaaggaggg tttattaatg  2640
```

```
agaagtttgt attaatatgt agcaaaggct tttccaatgg gtgaataaaa acacattcca 2700
ttaagtcaag ctgggagcag tggcatatac ctatagtccc agctgcacag gaggctgaga 2760
caggaggatt gcttgaagcc aggaattgga gatcagcctg ggcaacacag caagatccta 2820
tctcttaaaa aaagaaaaaa aaacctatta ataataaaac agtataaaca aaagctaaat 2880
aggtaaaata ttttttctga aataaaatta tttttgagt ctgatggaaa tgtttaagtg 2940
cagtaggcca gtgccagtga gaaataaat aacatcatac atgtttgtat gtgtttgcat 3000
cttgcttcta ctgaaagttt cagtgcaccc cacttactta gaactcggtg acatgatgta 3060
ctcctttatc tgggacacag cacaaaagag gtatgcagtg gggctgctct gacatgaaag 3120
tggaagttaa ggaatctggg ctcttatggg gtccttgtgg gccagccctt caggcctatt 3180
ttactttcat tttacatata gctctaattg gtttgattat ctcgttccca aggcagtggg 3240
agatccccat ttaaggaaag aaaaggggcc tggcacagtg gctcatgcct gtaatcccag 3300
cactttggga ggctgaggca agtgtatcac ctgaggtcag gagttcaaga ccagcctggc 3360
caacatggca aaatcccgtc tctactaaaa atattaaaaa attggctggg cgtggtggtt 3420
cgtgcctata atttcagcta ctcaggaggc tgaggcagga gaatcgctgt aacctggggg 3480
gtggaggttg cagtgagacg agatcatgcc acttcactcc agcctggcca acagagccat 3540
actccgtctc aaataaataa ataaataaat aaagggactt caaacacatg aacagcagcc 3600
aggggaagaa tcaaaatcat attctgtcaa gcaaactgga aaagtaccac tgtgtgtacc 3660
aatagcctcc ccaccacaga ccctgggagc atcgcctcat ttatggtgtg gtccagtcat 3720
ccatgtgaag gatgagtttc caggaaaagg ttattaaata ttcactgtaa catactggag 3780
gaggtgagga attgcataat acaatcttag aaaacttttt tttccccttt ctattttttg 3840
agacaggatc tcacttggc actcaggctg aggacagtg gtacaatcaa agctcatggc 3900
agcctcgacc tccctgggct tgggcaatcc tcccacaggt gtgcacctcc atagctggct 3960
aatttgtgta tttttttgtag agatgggggtt tcaccatgtt gcccaggctg gtctctaaca 4020
cttaggctca agtgatccac ctgcctcgtc ctcccaagat gctgggatta caggtgtgtg 4080
ccacaggtgt tcatcagaaa gcttttttcta ttattttttac cttcttgagt gggtagaacc 4140
tcagccacat agaaaataaa atgttctggc atgacttatt tagctctctg gaattacaaa 4200
gaaggaatga ggtgtgtaaa agagaacctg ggttttttgaa tcacaaattt agaattaat 4260
cgaaactctg cctcttactt gtttgtagac actgacagtg gcctcatgtt tttttttttt 4320
ttaatctata aaatggagat atctaacatg ttgagcctgg gcccacaggc aaagcacaat 4380
cctgatgtga gaagtactca gttcatgaca actgttgttc tcacatgcat agcataattt 4440
catattcaca ttggaggact tctcccaaaa tatggatgac gttccctact caaccttgaa 4500
cttaatcaaa atactcagtt tacttaactt cgtattagat tctgattccc tggaaccatt 4560
tatcgtgtgc cttaccatgc ttatatttta cttgatcttt tgcatacctt ctaaaactat 4620
tttagccaat ttaaaatttg acagtttgca ttaaattata ggttacaat atgctttatc 4680
cagctatacc tgccccaaat tctgacagat gcttttgcca cctctaaagg aagacccatg 4740
ttcatagtga tggagtttgt gtggactaac catgcaaggt tgccaaggaa aaatcgcttt 4800
acgcttccaa ggtacacact aagatgaaag taattttagt ccgtgtccag ttggattctt 4860
ggcacatagt tatcttctgc tagaacaaac taaaacagct acatgccagc aagggagaaa 4920
ggggaaggag gggcaaagtt ttgaaattttc atgtaaattt atgctgttca aaacgacgag 4980
ttcatgactt tgtgtataga gtaagaaatg ccttttcttt tttgagacag agtcttgctc 5040
tgtcacccag gctggagtgc agtggcacga tctgggctca ctacaacctc cgcctcctgg 5100
gttcaagcaa ttctctgcct cagcctcccg agtagctggg attacaggtg cctgccacca 5160
cacccggcta atttttgtat ttttagtaga gacgggggttt caccatggt gccaggctgg 5220
tcttgaactc ctgacctagt aatccacctg cctccgcctc ccaaagtgct gggattacag 5280
gcgtgagcca ctgcacccag ccagaaatgc cttctaatct ttggtttatc ttaattagcc 5340
aggacacttg gagtgcatcc cgaagtacct gatcagtggc cctttggaa tgtgtaaaac 5400
tcagctcact tatatccctg catccgctac agagacagaa tccaagctca tatgttccat 5460
cttctctggc tgtatagttt aaggaatgga aggcaccaga acagatttat tgaaatgttt 5520
attagctgaa gatttatttta gacagttgag gaaaacatca gcaccagca gtaaaattgg 5580
ctctcaaaga ttttcttctc ctgtggaaag tcagacctct gaggccccat ccaggtagaa 5640
gtactagtgc aagaagggcc tctgctgtcc actttgtgtt ctgtgatctg tgggaacatt 5700
gttaacgcca catcttgacc tcaaattgtt tagctcctgg ccagacacgg tggctcacac 5760
ctgtaatccc agcactttga gaggctgagg caggtggatc acctgaggtt aggagttcga 5820
ggccagcctg gtcaacatgg taaaaccccg cctctactaa aaatacaaaa attagctggc 5880
cgtagtggcg cacgcctgtt atcccagcta ctcgggaggc tgaggcagga gaattgcttg 5940
aacctgggtg gtggaggttg cagtgagccg agattacacc actgcactcc agcctgggtg 6000
acaagaggga aactccatta aaaaaatgta attcccgtgt ctgccatctt aagtgtaaag 6060
gtggctaaat tatatagaaa aataagacaa tatcatttcc caattacatt cctttcctac 6120
cgcactctat gatgctagct gagattttttc caaaagaaaa tggcttaaat aaaaccctaa 6180
gagaaagaaa aactttaaat ccctccaaag ctcaaaagta atagaaacag atgagtttgg 6240
agtcaggatt tctctgtaag attgcctagg ctgtgtactg cacatctcca ggtgccactg 6300
ttgacagaga ttataactac aatgtgaagt gaatggtgcc actgacagtt atgcaaaccg 6360
tccagagcat agccacctga tcctgctggg attcctcttg ccagtccatc agcagttccc 6420
cttgaaagtt tcaccaaaca tccctttaaat ctgccctctc ctgcccgtcc cagtggagg 6480
tcctcatcat ttttcacctg catttttgca ggagctttct tatatccacc ttcctccttt 6540
tctctcagcc catcatctag ctacacagtc tccagggtaa gctttcagaa aggcaatctc 6600
ttgtctgtaa aacctaagca ggaccaaggc caagtttctt agcctgaaaa atgtgctttt 6660
ctgactgaac tgttcaggca ctgactctac atataattat gcttttctac ccctcacac 6720
tcaacacttt gactccagca atcccaaatc cccagatctc taagtgtgct gtgctatttt 6780
cacgtggctc tcagacttgg ccagtgctgt ttccattttg gtctttattc cccacatctc 6840
tgcctggggg gtagattcta ccctgaaaaa tgttcttggc acagccttgc aaaactcctcc 6900
tccactcagc ctctgcctgg atgcccttga ttgttccatg tcctcagcat accatgtttg 6960
tcttttcccag cactgaccta ccatgtgtca ccctgcttg gctgtacctt ccatgaggct 7020
aggactatgt gtctcctttg ttgactgctg ttgcccctagc atcttgcaca gttccttgca 7080
cacaattaga gctctataaa tgtcaaatga atgtgttata attatatgtt taagatagtt 7140
gttcaaataa actctaaata acccccaac                                     7168

SEQ ID NO: 8             moltype = DNA   length = 7176
FEATURE                  Location/Qualifiers
```

| source | 1..7176 |
| | mol_type = other DNA |
| | organism = Homo sapiens |

SEQUENCE: 8

```
agtctccctt gggtcagggg tcctggttgc actccgtgct ttgcacaaag caggctctcc    60
attttttgtta aatgcacgaa tagtgctaag ctgggaagtt cttcctgagg tctaacctct   120
agctgctccc ccacagaaga gtgcctgcgg ccagtggcca ccaggggtcg ccgcagcacc   180
cagcgctgga gggcggagcg ggcggcagac ccggagcagc atgtggactc tcgggcgccg   240
cgcagtagcc ggcctcctgg cgtcacccag cccagcccag gcccagaccc tcacccgggt   300
cccgcggccg gcagagttgg ccccactctg cggccgccgt ggcctgcgca ccgacatcga   360
tgcgacctgc acgccccgcc gcgcaagttc gaaccaacgt ggcctcaacc agatttggaa   420
tgtcaaaaag cagagtgtct atttgatgaa tttgaggaaa tctggaactt tgggccaccc   480
aggctctcta gatgagacca cctatgaaag actagcagag gaaacgctgg actctttagc   540
agagttttt gaagacccttg cagacaagcc atacacgttt gaggactatg atgtctcctt   600
tgggagtggt gtcttaactg tcaaactggg tggagatcta ggaacctatg tgatcaacaa   660
gcagacgcca aacaagcaaa tctggctatc ttctccatcc aggtatgtag tggacctaag   720
cgttatgact ggactgggaa aaactgggtg tactcccacg acggcgtgtc cctccatgag   780
ctgctggccg cagagctcac taaagcctta aaaaccaaac tggacttgtc ttccttggcc   840
tattccggaa aagatgcttg atgcccagcc ccgttttaag gacattaaaa gctatcaggc   900
caagacccca gcttcattat gcagctgagg tctgtttttt gttgttgttg ttgtttattt   960
tttttattcc tgcttttgag gacagttggg ctatgtgtca cagctctgta gaaagaatgt  1020
gttgcctcct accttgcccc caagtgtctga ttttttaattt ctatggaaga tttttttggat 1080
tgtcggattt cctccctcac atgatacccc ttatctttta taatgtctta tgcctatacc  1140
tgaatataac aacctttaaa aaagcaaaat aataagaagg aaaaattcca ggagggaaaa  1200
tgaattgtct tcactcttca ttctttgaag gatttactgc aagaagtaca tgaagagcag  1260
ctggtcaacc tgctcactgt tctatctcca aatgagacac attaaaggt agcctacaaa  1320
tgttttcagg cttctttcaa agtgtaagca cttctgagct cttttagcatt gaagtgtcga  1380
aagcaactca cacgggaaga tcatttctta tttgtgctct gtgactgcca aggtgtggcc  1440
tgcactgggt tgtccaggga gacctagtgc tgtttctccc acatattcac atacgtgtct  1500
gtgtgtatat atatttttc aatttaaagg ttagtatgga atcagctgct acaagaatgc  1560
aaaaaatctt ccaaagacaa gaaaagagga aaaaaagccg ttttcatgag ctgagtgatg  1620
tagcgtaaca aacaaaatca tggagctgag gaggtgcctt gtaaacatga aggggcagat  1680
aaaggaagga gatactcatg ttgataaaga gagccctggt cctagacata gttcagccac  1740
aaagtagttg tcccttttgtg gacaagtttc ccaaattgcc tggacctctg cttccccata  1800
tgttaatga gagaatagag tatggttgat tcccagcatt cagtggtcct gtcaagcaac  1860
ctaacaggct agttctaatt ccctattggg tagatgaggg gatgacaaag aacagttttt  1920
aagctatata ggaaacattg ttattggtgt tgccctatcg tgatttcagt tgaattcatg  1980
tgaaaataat agccatcctt ggcctggcgc ggtggctcac acctgtaatc ccagcactct  2040
tggaggccaa ggtgggtgga tcacctgagg tcaggagttc aagaccagcc tggccaacat  2100
gatgaaaccc cgtctctact aaaaatacaa aaaattagcc gggcatgatg gcaggtgcct  2160
gtaatcccag ctacttggga ggctgaagcg aagaatcgc ttgaacccag aggtggaggt  2220
tgcagtgagc cgagatcgtg ccattgcact gtaacctggg tgactgagca aaactctgtc  2280
tcaaaataat aataacaata taataataat aatagccatc cttttattgta ccccttactgg  2340
gttaatcgta ttataccaca ttcctcatt ttaatttttta ctgacctgca ctttatacaa  2400
agcaacaagc ctccaggaca ttaaaattca tgcaaagtta tgctcatgtt atattatttt  2460
cttacttaaa gaaggattta ttagtggctg ggcatggtgg cgtgcacctg taatcccagc  2520
tactcaggag gctgagacgg gagaattgct tgacccccag gcgaggaggt tacagtgagt  2580
cgagatcgta cctgagcgac agagcgagac tccgtctcaa aaaaaaaaaa aaggagggtt  2640
tattaatgag aagtttgtat taatatgtag caaaggcttt tccaatgggt gaataaaaac  2700
acattccatt aagtcaagct gggagcagtg gcatatacct atagtcccag ctgcacagga  2760
ggctgagaca ggaggattgc ttgaagccaa gaattggaca tcagcctggg caacacagca  2820
agatcctatc tcttaaaaaa agaaaaaaaa acctattaat aataaaacag tataaacaaa  2880
agctaaatag gtaaaatatt ttttctgaaa taaaattatt ttttgagtct gatgaaatg   2940
tttaagtgca gtaggccagt gccagtgaga aaataaataa catcatacat gtttgtatgt  3000
gtttgcatct tgcttctact gaaagtttca gtgcaccccca cttacttaga actcggtgac  3060
atgatgtact cctttatctg ggacacagca caaagaggt atgcagtggg gctgctctga  3120
catgaaagtg gaagttaagg aatctggggct cttatggggt ccttgtgggc cagcccttca  3180
ggcctatttt acttttcattt tacatatagc tctaattggt tgattatct cgttcccaag   3240
gcagtgggag atcccccattt aaggaaagaa aaggggcctg gcacagtggc tcatgcctgt   3300
aatcccagca ctttgggagg ctgaggcaag tgtatcacct gaggtcagga gttcaagacc   3360
agcctggcca acatggcaaa atcccgtctc tactaaaaaat attaaaaaat tggctgggcg  3420
tggtggttcg tgcctataat ttcagctact caggaggctg aggcaggaga atcgctgtaa  3480
cctgggggtg gaggttgca gtgagacgag atcatgccac ttcactccag cctggccaac  3540
agagccatac tccgtctcaa ataaataaat aaataaataa agggacttca aacacatgaa  3600
cagcagccag gggaagaatc aaaatcatat tctgtcaagc aaactggaaa agtaccactg  3660
tgtgtaccaa tagcctcccc accacagacc ctgggagcat cgcctcattt atggtgtggt  3720
ccagtcatcc atgtgaagga tgagtttcca ggaaaaggtt attaaatatt cactgtaaca  3780
tactggagga ggtgaggaat tgcataatac aatcttagaa aacttttttt tccccttct   3840
attttttgag acaggatctc actttggcac tcaggctgga ggacagtggt acaatcaaag  3900
ctcatggcag cctcgacctc cctgggcttg gcaatcctc ccacaggtgt gcacctccat  3960
agctggctaa tttgtgtatt ttttgtagag atggggtttc accatgttgc ccaggctggt  4020
ctctaacact taggctcaag tgatccacct gcctcgtcct cccaagatgc tgggattaca  4080
ggtgtgtgcc acaggtgttc atcagaaagc ttttctatt attttttacct tcttgagtgg  4140
gtagaacctc agccacatag aaaataaat gttctggcat gacttattta gctctctgga  4200
attacaaaga aggaatgagg tgtcaaaaag agaaacctggg ttttttgaatc acaaatttag  4260
aatttaatcg aaactctgcc tcttacttgt ttgtagacaac tgcagtggc ctcatgtttt  4320
tttttttttt aatctataaa atggagatat ctaacatgtt gagcctgggc ccacaggcaa  4380
agcacaatcc tgatgtgaga agtactcagt tcatgacaac tgttgttctc acatgcatag  4440
cataatttca tattcacatt ggaggacttc tcccaaaata tggatgacgt tccctactca  4500
```

```
acccttgaact taatcaaaat actcagtttta cttaacttcg tattagattc tgattcccctg    4560
gaaccattta tcgtgtgcct taccatgctt atattttact tgatcttttg catacccttct    4620
aaaactattt tagccaattt aaaatttgac agtttgcatt aaattatagg tttacaatat    4680
gctttatcca gctatacctg ccccaaattc tgacagatgc ttttgccacc tctaaaggaa    4740
gacccatgtt catagtgatg gagttgtgt ggactaacca tgcaaggttg ccaaggaaaa    4800
atcgctttac gcttccaagg tacacactaa gatgaaagta attttagtcc gtgtccagtt    4860
ggattcttgg cacatagtta tcttctgcta gaacaaacta aaacagctac atgccagcaa    4920
gggagaaagg ggaaggaggg gcaaagtttt gaaatttcat gtaaatttat gctgttcaaa    4980
acgacgagtt catgactttg tgtatagagt aagaaatgcc ttttctttt tgagacagag    5040
tcttgctctg tcacccaggc tggagtgcag tggcacgatc tgggctcact acaacctccg    5100
cctcctgggt tcaagcaatt ctctgcctca gcctcccgag tagctgggat tacaggtgcc    5160
tgccaccaca cccggctaat ttttgtattt ttagtagaga cggggtttca ccatcatggc    5220
caggctggtc ttgaactcct gacctagtaa tccacctgcc tccgcctccc aaagtgctgg    5280
gattacaggc gtgagccact gcacccagcc agaaatgcct tctaatcttt ggttatctt    5340
aattagccag gacacttgga gtgcatcccg aagtacctga tcagtggcccc ctttggaatg    5400
tgtaaaactc agctcactta tatccctgca tccgctacag agacagaatc caagctcata    5460
tgttccatct tctctggctg tatagtttaa ggaatggaag gcaccagaac agatttattg    5520
aaatgtttat tagctgaaga tttatttaga cagttgagga aaacatcagc acccagcagt    5580
aaaattggct ctcaaagatt ttcttctcct gtggaaagtc agacctctga ggccccatcc    5640
aggtagaagt actagtgcaa gaagggcctc tgctgtccac ttgtgtttct gtgatctgtg    5700
ggaacattgt taacgccaca tcttgacctc aaattgttta gctcctggcc agacacggtg    5760
gctcacacct gtaatcccag cactttgaga ggctgaggca ggtggatcac ctgaggttag    5820
gagttcgagg ccagcctggt caacatggta aaacccgcc tctactaaaa atacaaaaat    5880
tagctggccg tagtggcgca cgcctgttat cccagctact cgggaggctg aggcaggaga    5940
attgcttgaa cctgggtggt ggaggttgca gtgagccgag attaccac tgcactccag    6000
cctgggtgac aagagggaaa ctccattaaa aaaatgtaat tcccgtgtct gccatcttaa    6060
gtgtaaaggt ggctaaatta tatagaaaaa taagacaata tcatttccca attacattcc    6120
tttcctaccg cactctatga tgctagctga gatttttcca aaagaaaatg gcttaaataa    6180
aacccctaaga gaaagaaaaa ctttaaatcc ctccaaagct caaagtaat agaaacagat    6240
gagtttggag tcaggatttc tctgtaagat tgcctagcc gtgtactgca catctccagg    6300
tgccactgtt gacagagatt ataactacaa tgtgaagtga atggtgccac tgacagtttat    6360
gcaaaccgtc cagagcatag ccacctgatc ctgctgggat tcctcttgcc agtccatcag    6420
cagttcccct tgaaagtttc accaaacatc ccttaaatct gccctctcct gcccgtcccc    6480
agtggaggtc ctcatcattt tcacctgca ttttttgcagg agctttctta tatccacctt    6540
cctccttttc tctcagccca tcatctagct acacagtctc cagggtaagc tttcagaaag    6600
gcaatctctt gtctgtaaaa cctaagcagg accaaggcca agtttcttag cctgaaaaat    6660
gtgctttttct gactgaactg ttcaggcact gactctacat ataattatgc ttttctaccc    6720
cctcacactc aaacactttga ctccagcaat cccaaatccc cagatcccta agtgtgctgt    6780
gctattttca cgtggctctc agacttggcc agtgctgttt ccattttggt ctttattccc    6840
cacatctctg cctggggggt agattctacc ctgaaaaatg ttcttggcac agccttgcaa    6900
actcctcctc cactcagcct ctgcctggat gcccttgatt gttccatgtc ctcagcatac    6960
catgtttgtc tttcccagca ctgacctacc atgtgtcacc cctgcttggc tgtacccttcc    7020
atgaggctag gactatgtgt ctccttttgtt gactgctgtt gccctagcat cttgcacagt    7080
tccttgcaca caattagagc tctataaatg tcaaataaat gtgttataat tatatgttta    7140
agatagttgt tcaaataaac tctaaataac cccaac                              7176
```

SEQ ID NO: 9          moltype = DNA  length = 980
FEATURE               Location/Qualifiers
source                1..980
                      mol_type = other DNA
                      organism = Homo sapiens
SEQUENCE: 9
```
agtctcccctt gggtcagggg tcctggttgc actccgtgct ttgcacaaag caggctctcc      60
attttttgtta aatgcacgaa tagtgctaag ctgggaagtt cttcctgagg tctaacctct    120
agctgctccc ccacagaaga gtgcctgcgg ccagtgggtcg ccgcagcacc                180
cagcgctgga gggcggagcg ggcggcagac ccggagcagc atgtggactc tcgggcgccg    240
cgcagtagcc ggcctcctgg cgtcacccag cccagcccag gccagaccc tcacccgggt    300
ccccgcggccg gcagagttgg ccccactctg cggccgccgt ggcctgcgca ccgacatcga    360
tgcgacctgc acgccccgcc gcgcaagttc gaaccaacgt ggcctcaacc agatttggaa    420
tgtcaaaaag cagagtgtct atttgatgaa tttgaggaaa tctgaacttt tgggccaccc    480
aggctctcta gatgagacca cctatgaaaa actagcagag gaaacgctgg actctttagc    540
agagtttttt gaagaccttg cagacaagcc atacacgttt gaggactatg atgtctcctt    600
tgggagtggt gtcttaactg tcaaactggg tggagatcta ggaacctatg tgatcaacaa    660
gcagacgcca aacaagcaaa tctggctatc ttctccatcc agtggtccca agcgttatga    720
gctgttccat ccctgaggaa aagtgaggac catgctctcc aaacaggcca tgtgctggac    780
tacctctgtt tctgtctcct gggattccaa tcagcaagtg agcaacgaag caacccagcc    840
agtgtggttc ataggatggc tgggtaagtg gctgtttgtt ttttccttac tgtggatatg    900
tatcagtgaa ggaatctgta gaacattctt gatgggaaca tttagtcata tcaagtcaat    960
aaattaatgt ttaggctggg                                                980
```

SEQ ID NO: 10         moltype = AA  length = 210
FEATURE               Location/Qualifiers
source                1..210
                      mol_type = protein
                      organism = Macaca fascicularis
SEQUENCE: 10
```
MWTFGRRAVA GLLASPSPAQ AQTLTRAPRL AELAQLCSRR GLRTGINATC TTHHTSSNLR      60
GLNQIRNVKR QSVYLMNLRK SGTLGHPGSL DDTTYERLAE ETLDSLAEFF EDLADKPYTF    120
EDYDVSFGSG VLTVKLGGDL GTYVINKQTP NKQIWLSSPS SGPKRYDWTG KNWVYSHDGV    180
```

```
SLHELLGAEL TKALKTKLDL SSLAYSGKDA                                   210

SEQ ID NO: 11           moltype = AA  length = 210
FEATURE                 Location/Qualifiers
source                  1..210
                        mol_type = protein
                        organism = Macaca fascicularis
SEQUENCE: 11
MWTFGRRAVA GLLASPSPAQ AQTLTRAPRL AELAQLCSRR GLRTGINATR TTHHTSSNLR   60
GLNQIRNVKR QSVYLMNLRK SGTLGHPGSL DDTTYERLAE ETLDSLAEFF EDLADKPYTF  120
EDYDVSFGSG VLTVKLGGDL GTYVINKQTP NKQIWLSSPS SGPKRYDRTG KNWVYSHDGV  180
SLHELLGAEL TKALKTKLDL SSLAYSGKDA                                   210

SEQ ID NO: 12           moltype = AA  length = 210
FEATURE                 Location/Qualifiers
source                  1..210
                        mol_type = protein
                        organism = Macaca mulatta
SEQUENCE: 12
MWTFGRRAVA GLLASPSPAQ AQTLTRAPRL AELAQLCSRR GLRTGINATC TTHHTSSNLR   60
GLNQIRNVKR QSVYLMNLRK SGTLGHPGSL DDTTYERLAE ETLDSLAEFF EDLADKPYTF  120
EDYDVSFGSG VLTVKLGGDL GTYVINKQTP NKQIWLSSPS SGPKRYDWTG KNWVYSHDGV  180
SLHELLGAEL TKALKTKLDL SSLAYSGKDA                                   210
```

We claim:

1. A method of delivering a payload to a tissue of the central nervous system (CNS) in a mammalian subject, wherein the method comprises: administering a first adeno-associated virus (AAV) particle to the subject by intravenous (IV) administration at a dose of at least $2.00 \times 10^{13}$ vg/kg; wherein the first AAV particle comprises:
   (i) an AAV capsid comprising the amino acid sequence of SEQ ID NO: 2; and
   (ii) a viral genome comprising at least one inverted terminal repeat (ITR) and a polynucleotide sequence encoding the payload.

2. The method of claim 1, wherein the method comprises treating, ameliorating, or preventing a neurological disease in the subject.

3. The method of claim 1, wherein the viral genome of the first AAV particle comprises a polynucleotide sequence encoding one or more microRNA binding sites.

4. The method of claim 3, wherein the one or more microRNA binding sites comprise one or more miRNA-122 binding sites.

5. The method of claim 1, wherein the viral genome comprises one, two, or three copies of a miRNA-122 binding site.

6. The method of claim 1, wherein the first AAV particle transduces the cerebellum or dorsal root ganglia (DRG) of the subject following administration.

7. The method of claim 1, wherein the method produces a clinical phenotypic result which lasts longer than 6 months.

8. The method of claim 1 wherein the method produces a clinical phenotypic result which lasts longer than 10 months.

9. The method of claim 1, wherein the method comprises administering a second AAV particle to the subject by intracerebral (IC) administration, wherein the second AAV particle comprises:
   (i) an AAV capsid; and
   (ii) a viral genome comprising at least one inverted terminal repeat (ITR) and a polynucleotide sequence encoding the payload.

10. The method of claim 9, wherein the second AAV particle comprises an AAVrh10 capsid.

11. The method of claim 9, wherein the method comprises treating, ameliorating, or preventing a neurological disease in the subject.

12. The method of claim 9, wherein the viral genome of the second AAV particle comprises a polynucleotide sequence encoding one or more microRNA binding sites.

13. The method of claim 12, wherein the one or more microRNA binding sites comprise one or more miRNA-122 binding sites.

14. The method of claim 9, wherein the viral genome of the second AAV particle comprises one, two, or three copies of a miRNA-122 binding site.

15. The method of claim 9, wherein both the first AAV particle and the second AAV particle transduce the cerebellum or dorsal root ganglia (DRG) of the subject following administration.

16. The method of claim 9, wherein the method produces a clinical phenotypic result which lasts longer than 6 months.

17. The method of claim 9, wherein the method produces a clinical phenotypic result which lasts longer than 10 months.

18. The method of claim 1, wherein the payload comprises a frataxin protein.

19. An adeno-associated virus (AAV) particle comprising an AAV capsid and viral genome, wherein the AAV capsid comprises the amino acid sequence of SEQ ID NO: 2, and wherein the viral genome comprises at least one inverted terminal repeat (ITR) and a polynucleotide sequence encoding a payload.

20. The AAV particle of claim 19, wherein the payload comprises a frataxin protein.

* * * * *